US006825185B2

(12) United States Patent
Khanapure et al.

(10) Patent No.: US 6,825,185 B2
(45) Date of Patent: Nov. 30, 2004

(54) SUBSTITUTED ARYL COMPOUNDS AS NOVEL CYCLOOXYGENASE-2 SELECTIVE INHIBITORS, COMPOSITIONS AND METHODS OF USE

(75) Inventors: Subhash P. Khanapure, Clinton, MA (US); David S. Garvey, Dover, MA (US); Richard A. Earl, Westford, MA (US); Maiko Ezawa, Acton, MA (US); Xinqin Fang, Lexington, MA (US); Ricky D. Gaston, Malden, MA (US)

(73) Assignee: NitroMed, Inc., Lexington, MA (US)

( * ) Notice: Subject to any disclaimer, the term of this patent is extended or adjusted under 35 U.S.C. 154(b) by 0 days.

(21) Appl. No.: 10/730,979

(22) Filed: Dec. 10, 2003

(65) Prior Publication Data

US 2004/0116431 A1 Jun. 17, 2004

Related U.S. Application Data

(62) Division of application No. 10/024,046, filed on Dec. 21, 2001, now Pat. No. 6,706,724.
(60) Provisional application No. 60/256,932, filed on Dec. 21, 2000.

(51) Int. Cl.$^7$ ....................... A61K 31/33; A61K 31/505; A61K 31/435; C07D 237/00; C07D 239/00

(52) U.S. Cl. ................... 514/183; 514/277; 514/252.05; 514/256; 514/365; 514/367; 514/374; 514/375; 514/461; 514/469; 544/224; 544/242; 546/1

(58) Field of Search ................................ 514/183, 277, 514/252.01, 256, 365, 367, 374, 375, 461, 469; 546/1; 544/224, 242

(56) References Cited

U.S. PATENT DOCUMENTS

| 5,281,613 A | 1/1994 | Bradbury et al. |
| 5,387,592 A | 2/1995 | Bradbury et al. |

(List continued on next page.)

FOREIGN PATENT DOCUMENTS

| EP | 1 052 238 A1 | 11/2000 |
| JP | 6-107646 | 4/1994 |

(List continued on next page.)

OTHER PUBLICATIONS

Nathan"NO as a secretory product of mammalian cells", FASEB J.6,3052–3064(1992).*
Schlosser et al, "COX–2 is Overexpressed . . . ", PubMed:12131767;Pancreas,25/1,26–30(2002).*
Slominany et al,"Activn . . . COX and NOS during . . . ulcer healing",PuBMed;J.Physiol.Pharmacol,53/2, 159–69(2002).*
Rajnakova et al,"Expression of NOS,COx–2 and p53 . . . gastric cancer",PubMed:11566494;Cancer Lett,172/2, 177–85(2001).*
Devaux et al,"Lipopolysaccharide–induced . . . E2 mediated . . . NOS activn . . . Cox2 . . . ";PuBMed;J.Immun., 167/7,3962(2001).*
McCarthy et al,"Prev. and Treatment of gastroint. and complicn. due to NSAIDs",PuBMed:11566039;Best Pract. res. Clin Gast., 15/5,755(2001).*
Ahmad et al,"Renal failure . . . celecoxib and refecoxib", PuBMed:12093311;Drug Saf,25/7,537–44(2002).*
Dicjens et al,"COX–2 Expres. in Padiatric Sarcomas", PuBMed:12024286;Pediatr Dev Pathol,5/4(2002).*
Cutsem et al,"The treatm . . . adv.colorectal cancer . . . ", puBMed:11969241;Best Pract.res Clin Gastr.,16/2, 319(2002).*
Khanna et al,"Selective COX–2 inhibitors: heteroaryl modif . . . diarylimidazoles are potent, orally active antinflam . . . ", PuBMed:10956225;J.Med.Chem. 43/16, 3168(2000).*
Oct. 27, 2003. International Search Report from International Application No. PCT/US01/48823.

*Primary Examiner*—Richard L. Raymond
*Assistant Examiner*—Sudhaker B. Patel
(74) *Attorney, Agent, or Firm*—Wilmer Cutler Pickering Hale and Dorr LLP

(57) ABSTRACT

The invention describes novel substituted aryl compounds that are cyclooxygenase 2 (COX-2) selective inhibitors and novel compositions comprising at least one cyclooxygenase 2 (COX-2) selective inhibitor, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or, optionally, at least one therapeutic agent, such as, steroids, nonsterodal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or nonsedating anti-histamines, inducible nitric oxide synthase inhibitors, opioids, analgesics, *Helicobacter pylori* inhibitors, proton pump inhibitors, isoprostane inhibitors, and mixtures thereof. The invention also provides novel kits comprising at least one COX-2 selective inhibitor, and, optionally, at least one nitric oxide donor, and/or, optionally, at least one therapeutic agent. The novel cyclooxygenase 2 selective inhibitors of the invention can be optionally nitrosated and/or nitrosylated. The invention also provides methods for treating inflammation, pain and fever; for treating and/or improving the gastrointestinal properties of COX-2 selective inhibitors; for facilitating wound healing; for treating and/or preventing renal toxicity or other toxicities; for treating and/or preventing other disorders resulting from elevated levels of cyclooxygenase-2; and for improving the cardiovascular profile of COX-2 selective inhibitors.

54 Claims, No Drawings

U.S. PATENT DOCUMENTS

| | | | |
|---|---|---|---|
| 5,463,135 | A | 10/1995 | Kanschik-Conradsen et al. |
| 5,474,995 | A | 12/1995 | Ducharme et al. |
| 5,567,711 | A | 10/1996 | Sheppard et al. |
| 5,593,994 | A | 1/1997 | Batt et al. |
| 5,621,000 | A | 4/1997 | Arena et al. |
| 5,643,922 | A | 7/1997 | Sheppard et al. |
| 5,654,305 | A | 8/1997 | Sheppard et al. |
| 5,700,947 | A | 12/1997 | Soldato |
| 5,703,073 | A | 12/1997 | Garvey et al. |
| 5,710,159 | A | 1/1998 | Voss et al. |
| 5,719,164 | A | 2/1998 | Weidmann et al. |
| 5,726,305 | A | 3/1998 | Weidmann et al. |
| 5,780,495 | A | 7/1998 | Del Soldato |
| 5,861,426 | A | 1/1999 | Del Soldato et al. |
| 5,932,586 | A | 8/1999 | Batt et al. |
| 5,990,148 | A | 11/1999 | Isakson et al. |
| 6,010,981 | A | 1/2000 | Siddall et al. |
| 6,040,341 | A | 3/2000 | Del Soldato et al. |
| 6,043,232 | A | 3/2000 | Garvey et al. |
| 6,043,233 | A | 3/2000 | Garvey et al. |
| 6,046,217 | A | 4/2000 | Friesen et al. |
| 6,048,858 | A | 4/2000 | Garvey et al. |
| 6,051,588 | A | 4/2000 | Garvey et al. |
| 6,057,347 | A | 5/2000 | Garvey et al. |
| 6,083,515 | A | 7/2000 | Garvey et al. |
| 6,143,734 | A | 11/2000 | Garvey et al. |
| 6,232,315 | B1 | 5/2001 | Shafer et al. |
| 6,245,797 | B1 | 6/2001 | Winokur |
| 6,248,745 | B1 | 6/2001 | Hamley et al. |
| 6,297,260 | B1 | 10/2001 | Bandarage et al. |
| 6,323,234 | B1 | 11/2001 | Garvey et al. |
| 6,436,967 | B1 | 8/2002 | Talley et al. |

FOREIGN PATENT DOCUMENTS

| | | | |
|---|---|---|---|
| WO | WO 94/04484 | | 3/1994 |
| WO | WO 94/12463 | | 6/1994 |
| WO | WO 95/01426 | | 1/1995 |
| WO | WO 95/09831 | | 4/1995 |
| WO | WO 95/30641 | | 11/1995 |
| WO | 9610012 | * | 4/1996 |
| WO | WO 96/10012 | | 4/1996 |
| WO | WO 96/16934 | | 6/1996 |
| WO | WO 96/26921 | | 9/1996 |
| WO | 9626921 | * | 9/1996 |
| WO | WO 96/32946 | | 10/1996 |
| WO | WO 97/31654 | | 9/1997 |
| WO | WO 98/09948 | | 3/1998 |
| WO | WO 98/26127 | | 6/1998 |
| WO | WO 98/56899 | | 12/1998 |
| WO | WO 98/57633 | | 12/1998 |
| WO | WO 99/14194 | | 3/1999 |
| WO | WO 99/14195 | | 3/1999 |
| WO | WO 99/15487 | | 4/1999 |
| WO | WO 99/20110 | | 4/1999 |
| WO | WO 99/21859 | | 5/1999 |
| WO | WO 99/34054 | | 7/1999 |
| WO | WO 99/44595 | | 9/1999 |
| WO | WO 99/45004 | | 9/1999 |
| WO | WO 99/45913 | | 9/1999 |
| WO | WO 99/58635 | | 11/1999 |
| WO | WO 00/05225 | | 2/2000 |
| WO | WO 00/06585 | | 2/2000 |
| WO | WO 00/18352 | | 4/2000 |
| WO | WO 00/25776 | | 5/2000 |
| WO | WO 00/44705 | | 8/2000 |
| WO | WO 00/51988 | | 8/2000 |
| WO | WO 00/61537 | | 10/2000 |
| WO | WO 00/61541 | | 10/2000 |
| WO | WO 00/61549 | | 10/2000 |
| WO | WO 00/61604 | | 10/2000 |
| WO | WO 00/72838 A1 | | 12/2000 |
| WO | WO 00/73278 A2 | | 12/2000 |
| WO | WO 01/00563 A1 | | 1/2001 |
| WO | WO 01/04082 A1 | | 1/2001 |
| WO | WO 01/10814 A1 | | 2/2001 |
| WO | WO 01/12584 A2 | | 2/2001 |
| WO | WO 01/54688 A1 | | 8/2001 |
| WO | WO 01/54691 A1 | | 8/2001 |
| WO | WO 01/56573 A1 | | 8/2001 |
| WO | WO 01/87353 A2 | | 11/2001 |
| WO | WO 02/00166 A2 | | 1/2002 |

* cited by examiner

SUBSTITUTED ARYL COMPOUNDS AS NOVEL CYCLOOXYGENASE-2 SELECTIVE INHIBITORS, COMPOSITIONS AND METHODS OF USE

RELATED APPLICATIONS

This application is a divisional of U.S. application Ser. No. 10/024,046 filed Dec. 21, 2001, now U.S Pat. No. 6,706,724, which claims priority to U.S. Provisional Application No. 60/256,932 filed Dec. 21, 2000.

FIELD OF THE INVENTION

The invention describes novel substituted aryl compounds that are cyclooxygenase 2 (COX-2) selective inhibitors and novel compositions comprising at least one cyclooxygenase 2 (COX-2) selective inhibitor, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or, optionally, at least one therapeutic agent. The invention also provides novel kits comprising at least one COX-2 selective inhibitor, and, optionally, at least one nitric oxide donor, and/or, optionally, at least one therapeutic agent. The novel cyclooxygenase 2 selective inhibitors of the invention can be optionally nitrosated and/or nitrosylated. The invention also provides methods for treating inflammation, pain and fever; for treating and/or improving the gastrointestinal properties of COX-2 selective inhibitors; for facilitating wound healing; for treating and/or preventing renal toxicity or other toxicities; for treating and/or preventing other disorders resulting from elevated levels of cyclooxygenase-2; and for improving the cardiovascular profile of COX-2 selective inhibitors.

BACKGROUND OF THE INVENTION

Nonsteroidal anti-inflammatory compounds (NSAIDs) are widely used for the treatment of pain, inflammation, and acute and chronic inflammatory disorders such as osteoarthritis and rheumatoid arthritis. These compounds inhibit the activity of the enzyme cyclooxygenase (COX), also known as prostaglandin G/H synthase, which is the enzyme that converts arachidonic acid into prostanoids. The NSAIDs also inhibit the production of other prostaglandins, especially prostaglandin $G_2$, prostaglandin $H_2$ and prostaglandin $E_2$, thereby reducing the prostaglandin-induced pain and swelling associated with the inflammation process. The chronic use of NSAIDs has been associated with adverse effects, such as gastrointestinal ulceration and renal toxicity. The undesirable side effects are also due to the inhibition of prostaglandin in the affected organ.

Recently two isoforms of cyclooxygenase, encoded by two distinct genes (Kujubu et al, *J. Biol. Chem.*, 266, 12866–12872 (1991)), have been identified—a constitutive form, cyclooxygenase-1 (COX-1), and an inductive form, cyclooxygenase-2 (COX-2). It is thought that the antiinflammatory effects of NSAIDs are mediated by the inhibition of COX-2, whereas the side effects seem to be caused by the inhibition of COX-1. The NSAIDs currently on the market either inhibit both isoforms of COX with little selectivity for either isoform or are COX-1 selective. Recently compounds that are COX-2 selective inhibitors have been developed and marketed. These COX-2 selective inhibitors have the desired therapeutic profile of an antiinflammatory drug without the adverse effects commonly associated with the inhibition of COX-1. However, these compounds can result in dyspepsia and can cause gastropathy (Mohammed et al, *N. Engl. J. Med.*, 340(25) 2005 (1999)). Additionally the COX-2 selective inhibitors can increase the risk of cardiovascular events in a patient (Mukherjee et al., *JAMA* 286(8) 954–959 (2001)); Hennan et al., Circulation, 104:820–825 (2001)).

There is still a need in the art for novel COX-2 selective inhibitor compounds that have gastroprotective properties, facilitate wound healing, decreased renal toxicity and dyspepsia, improved cardiovascular profile and that can be used at low dosages. The invention is directed to these, as well as other, important ends.

SUMMARY OF THE INVENTION

The invention provides novel aryl substituted compounds that are COX-2 selective inhibitors. These compounds are potent analgesics, have antiinflammatory properties and have an unexpected potential for facilitating wound healing. The novel compounds also have unexpected properties in the treatment and/or prevention of renal toxicity and for improving the cardiovascular profile of COX-2 selective inhibitors. The invention also provides compositions comprising the novel compounds described herein in a pharmaceutically acceptable carrier.

The invention is also based on the discovery that administering at least one COX-2 selective inhibitor, and, optionally, at least one nitric oxide donor reduces the gastrointestinal distress induced by COX-2 selective inhibitors. A nitric oxide donor is a compound that contains a nitric oxide moiety and which releases or chemically transfers nitric oxide to another molecule. Nitric oxide donors include, for example, S-nitrosothiols, nitrites, nitrates, N-oxo-N-nitrosamines, SPM 3672, SPM 5185, SPM 5186 and analogues thereof, and substrates of the various isozymes of nitric oxide synthase. Thus, another aspect of the invention provides compositions comprising at least one COX-2 selective inhibitor, and at least one compound that donates, transfers or releases nitric oxide as a charged species, i.e., nitrosonium ($NO^+$) or nitroxyl ($NO-$), or as the neutral species, nitric oxide ($NO·$), and/or stimulates endogenous production of nitric oxide or EDRF in vivo and/or is a substrate for nitric oxide synthase.

Yet another aspect of the invention provides compositions comprising at least one COX-2 selective inhibitor that is substituted with at least one nitrogen monoxide group (NO), and/or at least one nitrogen dioxide group ($NO_2$) (i.e., nitrosylated and/or nitrosated). The COX-2 selective inhibitors can be nitrosated and/or nitrosylated through one or more sites such as oxygen (hydroxyl condensation), sulfur (sulfhydryl condensation) and/or nitrogen. The invention also provides compositions comprising a therapeutically effective amount of such compounds in a pharmaceutically acceptable carrier.

Another aspect of the invention provides compositions comprising a therapeutically effective amount of at least one COX-2 selective inhibitor that is substituted with at least one NO and/or $NO_2$ group (i.e., nitrosylated and/or nitrosated), and at least one compound that donates, transfers or releases nitrogen monoxide as a charged species, i.e., nitrosonium ($NO^+$) or nitroxyl ($NO-$), or as the neutral species, nitric oxide ($NO·$), and/or stimulates endogenous production of nitric oxide or EDRF in vivo and/or is a substrate for nitric oxide synthase. The invention also provides for such compositions in a pharmaceutically acceptable carrier.

Yet another aspect of the invention provides compositions comprising at least one COX-2 selective inhibitor, that is optionally substituted with at least one NO and/or $NO_2$ group (i.e., nitrosylated and/or nitrosated), and, optionally, at least one compound that donates, transfers or releases nitric oxide as a charged species, i.e., nitrosonium ($NO^+$) or nitroxyl ($NO-$), or as the neutral species, nitric oxide ($NO\cdot$), and/or stimulates endogenous production of nitric oxide or EDRF in vivo and/or is a substrate for nitric oxide synthase, and/or, optionally, at least one therapeutic agent, including but not limited to, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating antihistamines, inducible nitric oxide synthase inhibitors, opioids, analgesics, *Helicobacter pylori* inhibitors, proton pump inhibitors, isoprostane inhibitors, and the like.

Yet another aspect of the invention provides methods for treating and/or preventing inflammation, pain and fever; for treating and/or improving gastrointestinal properties of COX-2 selective inhibitors; for facilitating wound healing; for treating and/or preventing renal toxicity; and for treating and/or preventing COX-2 mediated disorders (i.e., disorders resulting from elevated levels of COX-2) in a patient in need thereof which comprises administering to the patient a therapeutically effective amount of at least one COX-2 selective inhibitor, that is optionally substituted with at least one NO and/or $NO_2$ group (i.e., nitrosylated and/or nitrosated), and, optionally, at least one compound that donates, transfers or releases nitric oxide as a charged species, i.e., nitrosonium ($NO^+$) or nitroxyl ($NO-$), or as the neutral species, nitric oxide ($NO\cdot$), and/or stimulates endogenous production of nitric oxide or EDRF in vivo and/or is a substrate for nitric oxide synthase and/or stimulates endogenous production of NO or EDRF in vivo and/or is a substrate for nitric oxide synthase (i.e. NO donor). The methods can optionally further comprise the administration of at least one therapeutic agent, such as, for example, steroids, nonsteroidal antiinflammatory compounds (NSAID), 5-lipoxygenase (5-LO) inhibitors, leukotriene $B_4$ ($LTB_4$) receptor antagonists, leukotriene $A_4$ (LTA) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and mixtures thereof. In this aspect of the invention, the methods can involve administering the COX-2 selective inhibitors, that are optionally nitrosated and/or nitrosylated, administering the COX-2 selective inhibitors, that are optionally nitrosated and/or nitrosylated, and NO donors, administering the COX-2 selective inhibitors, that are optionally nitrosated and/or nitrosylated, and therapeutic agents, or administering the COX-2 selective inhibitors, that are optionally nitrosated and/or nitrosylated, NO donors, and therapeutic agents.

Yet another aspect of the invention provides methods for improving the cardiovascular profile of COX-2 selective inhibitors in a patient in need thereof which comprises administering to the patient a therapeutically effective amount of at least one COX-2 selective inhibitor, substituted with at least one NO and/or $NO_2$ group (i.e., nitrosylated and/or nitrosated), and, optionally, at least one compound that donates, transfers or releases nitric oxide as a charged species, i.e., nitrosonium ($NO^+$) or nitroxyl ($NO-$), or as the neutral species, nitric oxide ($NO\cdot$), and/or stimulates endogenous production of nitric oxide or EDRF in vivo and/or is a substrate for nitric oxide synthase and/or stimulates endogenous production of NO or EDRF in vivo and/or is a substrate for nitric oxide synthase (i.e. NO donor). The methods can optionally further comprise the administration of at least one of 3-hydroxy-3-methylglutaryl coenzyme A (HMG-CoA) inhibitors, antiplatelet agents, thrombin inhibitors, thromboxane inhibitors, and mixtures thereof. In this aspect of the invention, the methods can involve administering the nitrosated and/or nitrosylated COX-2 selective inhibitors, administering the COX-2 selective inhibitors, that are optinally nitrosated and/or nitrosylated, and NO donors, administering the COX-2 selective inhibitors, that are optionally nitrosated and/or nitrosylated, and at least one of 3-hydroxy-3-methylglutaryl coenzyme A (HMG-CoA) inhibitors, antiplatelet agents, thrombin inhibitors or thromboxane inhibitors, or administering the COX-2 selective inhibitors, that are optinally nitrosated and/or nitrosylated, NO donors, and at least one of 3-hydroxy-3-methylglutaryl coenzyme A (HMG-CoA) inhibitors, antiplatelet agents, thrombin inhibitors or thromboxane inhibitors.

In yet another aspect the invention provides kits comprising at least one COX-2 selective inhibitor, that is optionally substituted with at least one NO and/or $NO_2$ group (i.e., nitrosylated and/or nitrosated), and, optionally, at least one compound that donates, transfers or releases nitric oxide as a charged species, i.e., nitrosonium ($NO^+$) or nitroxyl ($NO-$), or as the neutral species, nitric oxide ($NO\cdot$), and/or stimulates endogenous production of nitric oxide or EDRF in vivo and/or is a substrate for nitric oxide synthase. The kit can further comprise at least one therapeutic agent, such as, for example, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and mixtures thereof. The COX-2 selective inhibitor, the nitric oxide donor and/or therapeutic agent, can be separate components in the kit or can be in the form of a composition in one or more pharmaceutically acceptable carriers.

DETAILED DESCRIPTION OF THE INVENTION

As used throughout the disclosure, the following terms, unless otherwise indicated, shall be understood to have the following meanings.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

"Cyclooxygenase-2 (COX-2) selective inhibitor" refers to a compound that selectively inhibits the cyclooxygenase-2 enzyme over the cyclooxygenase-1 enzyme. In one embodiment, the compound has a cyclooxygenase-2 $IC_{50}$ of less than about 2 µM and a cyclooxygenase-1 $IC_{50}$ of greater than about 5 µM, in the human whole blood COX-2 assay (as described in Brideau et al., *Inflamm Res.*, 45: 68–74 (1996)) and also has a selectivity ratio of cyclooxygenase-2 inhibition over cyclooxygenase-1 inhibition of at least 10, and preferably of at least 40. In another embodiment, the compound has a cyclooxygenase-1 $IC_{50}$ of greater than about 1 µM, and preferably of greater than 20 µM. The compound can also inhibit the enzyme, lipoxygenase. Such selectivity may indicate an ability to reduce the incidence of common NSAID-induced side effects.

"Therapeutic agent" includes any therapeutic agent that can be used to treat or prevent the diseases described herein. "Therapeutic agents" include, for example, steroids, nonsteroidal antiinflammatory compounds, 5-lipoxygenase inhibitors, leukotriene $B_4$ receptor antagonists, leukotriene $A_4$ hydrolase inhibitors, 3-hydroxy-3-methylglutaryl coenzyme A inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like. Although NO donors have therapeutic activity, the term "therapeutic agent" does not include NO donors described herein, since NO donors are separately defined.

"Cardiovascular disease or disorder" refers to any cardiovascular disease or disorder known in the art, including, but not limited to, restenosis, atherosclerosis, atherogenesis, angina, (particularly chronic, stable angina pectoris), ischemic disease, congestive heart failure or pulmonary edema associated with acute myocardial infarction, thrombosis, controlling blood pressure in hypertension (especially hypertension associated with cardiovascular surgical procedures), thromboemboembolic events, platelet aggregation, platelet adhesion, smooth muscle cell proliferation, vascular complications associated with the use of medical devices, wounds associated with the use of medical devices, cerebrovascular ischemic events, and the like. Complications associated with the use of medical devices may occur as a result of increased platelet deposition, activation, thrombus formation or consumption of platelets and coagulation proteins. Such complications, which are within the definition of "cardiovascular disease or disorder," include, for example, myocardial infarction, ischemic stroke, transient ischemic stroke, thromboemboembolic events, pulmonary thromboembolism, cerebral thromboembolism, thrombophlebitis, thrombocytopenia, bleeding disorders and/or any other complications which occur either directly or indirectly as a result of the foregoing disorders.

"Restenosis" is a cardiovascular disease or disorder that refers to the closure of a peripheral or coronary artery following trauma to the artery caused by an injury such as, for example, angioplasty, balloon dilation, atherectomy, laser ablation treatment or stent insertion. For these angioplasty procedures, restenosis occurs at a rate of about 30–60% depending upon the vessel location, lesion length and a number of other variables. Restenosis can also occur following a number of invasive surgical techniques, such as, for example, transplant surgery, vein grafting, coronary artery bypass surgery, endarterectomy, heart transplantation, balloon angioplasty, atherectomy, laser ablation, endovascular stenting, and the like.

"Atherosclerosis" is a form of chronic vascular injury in which some of the normal vascular smooth muscle cells in the artery wall, which ordinarily control vascular tone regulating blood flow, change their nature and develop "cancer-like" behavior. These vascular smooth muscle cells become abnormally proliferative, secreting substances such as growth factors, tissue-degradation enzymes and other proteins, which enable them to invade and spread into the inner vessel lining, blocking blood flow and making that vessel abnormally susceptible to being completely blocked by local blood clotting, resulting in the death of the tissue served by that artery. Atherosclerotic cardiovascular disease, coronary heart disease (also known as coronary artery disease or ischemic heart disease), cerebrovascular disease and peripheral vessel disease are all common manifestations of atherosclerosis and are therefore encompassed by the terms "atherosclerosis" and "atherosclerotic disease".

"Improving the cardiovascular profile" refers to and includes reducing the risk of thromboembolic events, reducing the risk of developing atherosclerosis and atherosclerotic diseases, and inhibiting platelet aggregation.

"Thromboemboembolic events" includes, but is not limited to, ischemic stroke, transient ischemic stroke, myocardial infarction, angina pectoris, thrombosis, thromboembolism, thrombotic occlusion and reocclusion, acute vascular events, restenosis, transient ischemic attacks, and first and subsequent thrombotic stroke. Patients who are at risk of developing thromboembolic events, may include those with a familial history of, or genetically predisposed to, thromboembolic disorders, who have had ischemic stroke, transient ischemic stroke, myocardial infarction, and those with unstable angina pectoris or chronic stable angina pectoris and patients with altered prostacyclin/thromboxane $A_2$ homeostasis or higher than normal thromboxane $A_2$ levels leading to increase risk for thromboembolism, including patients with diabetes and rheumatoid arthritis.

"Thromboxane inhibitor" refers to any compound that reversibly or irreversibly inhibits thromboxane synthesis, and includes compounds which are the so-called thromboxane $A_2$ receptor antagonists, thromboxane $A_2$ antagonists, thromboxane $A_2$/prostaglandin endoperoxide antagonists, thromboxane receptor (TP) antagonists, thromboxane antagonists, thromboxane synthase inhibitors, and dual acting thromboxane synthase inhibitors and thromboxane receptor antagonists. The characteristics of the preferred thromboxane inhibitor should include the suppression of thromboxane $A_2$ formation (thromboxane synthase inhibitors) and/or blockade of thromboxane $A_2$ and prostaglandin $H_2$ platelet and vessel wall (thromboxane receptor antagonists). The effects should block platelet activation and therefore platelet function.

"Thromboxane $A_2$ receptor antagonist" refers to any compound that reversibly or irreversibly blocks the activation of any thromboxane $A_2$ receptor.

"Thromboxane synthase inhibitor" refers to any compound that reversibly or irreversibly inhibits the enzyme thromboxane synthesis thereby reducing the formation of thromboxane $A_2$. Thromboxane synthase inhibitors may also increase the synthesis of antiaggregatory prostaglandins including prostacyclin and prostaglandin $D_2$. Thromboxane $A_2$ receptor antagonists and thromboxane synthase inhibitors and can be identified using the assays described in Tai, Methods of Enzymology, Vol. 86, 110–113 (1982); Hall, *Medicinal Research Reviews*, 11:503–579 (1991) and Coleman et al., *Pharmacol Rev.*, 46: 205–229 (1994) and references therein, the disclosures of which are incorporated herein by reference in its entirety.

"Dual acting thromboxane receptor antagonist and thromboxane synthase inhibitor" refers to any compound that simultaneously acts as a thromboxane $A_2$ receptor antagonist and a thromboxane synthase inhibitor.

"Thrombin inhibitors" refers to and includes compounds that inhibit hydrolytic activity of thrombin, including the catalytic conversion of fibrinogen to fibrin, activation of Factor V to Va, Factor VIII to VIIIa, Factor XIII to XIIIa and platelet activation. Thrombin inhibitors may be identified using assays described in Lewis et at., Thrombosis Research. 70: 173–190 (1993).

"Platelet aggregation" refers to the binding of one or more platelets to each other. Platelet aggregation is commonly referred to in the context of generalized atherosclerosis, not with respect to platelet adhesion on vasculature damaged as a result of physical injury during a medical procedure. Platelet aggregation requires platelet activation which depends on the interaction between the ligand and its specific platelet surface receptor.

"Platelet activation" refers either to the change in conformation (shape) of a cell, expression of cell surface proteins (e.g., the IIb/IIIa receptor complex, loss of GPIb surface protein), and secretion of platelet derived factors (e.g., serotonin, growth factors).

"Patient" refers to animals, preferably mammals, most preferably humans, and includes males and females, and children and adults.

"Therapeutically effective amount" refers to the amount of the compound and/or composition that is effective to achieve its intended purpose.

"Treating" or "treatment" refers to and includes alleviating, ameliorating, relieving or otherwise reducing the signs and symptoms associated with a disease or disorder.

"Preventing" or "prevention" refers to and includes prophylaxis or delaying the onset or progression of a disease or disorders, or the signs and symptoms associated with such disease or disorder.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, $NO·$), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, $NO^-$, $NO·$), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, a hydroxyalkyl group, an alkenyl group, an alkynyl group, a bridged cycloalkyl group, a cycloalkyl group or a heterocyclic ring, as defined herein. An alkyl group may also comprise one or more radical species, such as, for example a cycloalkylalkyl group or a heterocyclicalkyl group.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Substituted lower alkyl" refers to a lower alkyl group, as defined herein, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$–$C_{10}$ hydrocarbon (preferably a $C_2$–$C_8$ hydrocarbon, more preferably a $C_2$–$C_6$ hydrocarbon) that can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Lower alkenyl" refers to a branched or straight chain $C_2$–$C_4$ hydrocarbon that can comprise one or two carbon-carbon double bonds.

"Substituted alkenyl" refers to a branched or straight chain $C_2$–$C_{10}$ hydrocarbon (preferably a $C_2$–$C_8$ hydrocarbon, more preferably a $C_2$–$C_6$ hydrocarbon) which can comprise one or more carbon-carbon double bonds, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Alkynyl" refers to an unsaturated acyclic $C_2$–$C_{10}$ hydrocarbon (preferably a $C_2$–$C_8$ hydrocarbon, more preferably a $C_2$–$C_6$ hydrocarbon) that can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0) octane, 7-oxabycyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamido and nitro. Exemplary heterocyclic groups include pyrrolyl, furyl, thienyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, pyrrolinyl, pyrrolindinyl, oxazolindinyl 1,3-dioxolanyl, imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3, 5-trithianyl, benzo(b)thiophenyl, benzimidazolyl, benzothiazolinyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Cycloalkenyl" refers to an unsaturated cyclic $C_2$–$C_{10}$ hydrocarbon (preferably a $C_2$–$C_8$ hydrocarbon, more preferably a $C_2$–$C_6$ hydrocarbon) which can comprise one or more carbon-carbon triple bonds.

"Arylalkyl" refers to an aryl radical, as defined herein, attached to an alkyl radical, as defined herein. Exemplary arylalkyl groups include benzyl, phenylethyl, 4-hydroxybenzyl, 3-fluorobenzyl, 2-fluorophenylethyl, and the like.

"Arylalkenyl" refers to an aryl radical, as defined herein, attached to an alkenyl radical, as defined herein. Exemplary arylalkenyl groups include styryl, propenylphenyl, and the like.

"Cycloalkylalkyl" refers to a cycloalkyl radical, as defined herein, attached to an alkyl radical, as defined herein.

"Cycloalkylalkoxy" refers to a cycloalkyl radical, as defined herein, attached to an alkoxy radical, as defined herein.

"Cycloalkylalkylthio" refers to a cycloalkyl radical, as defined herein, attached to an alkylthio radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkoxy" refers to $R_{50}O$—, wherein $R_{50}$ is an alkyl group, as defined herein (preferably a lower alkyl group or a haloalkyl group, as defined herein). Exemplary alkoxy groups include methoxy, ethoxy, t-butoxy, cyclopentyloxy, trifluoromethoxy, and the like.

"Lower alkoxy" refers to a lower alkyl group, as defined herein, appended to an oxygen atom.

"Aryloxy" refers to $R_{55}O$—, wherein $R_{55}$ is an aryl group, as defined herein. Exemplary arylkoxy groups include napthyloxy, quinolyloxy, isoquinolizinyloxy, and the like.

"Alkylthio" refers to $R_{50}S$—, wherein $R_{50}$ is an alkyl group, as defined herein.

"Lower alkylthio" refers to a lower alkyl group, as defined herein, appended to a thio group, as defined herein.

"Arylalkoxy" or "alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Cycloalkylthio" refers to $R_{54}S—$, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Haloalkoxy" refers to an alkoxy group, as defined herein, in which one or more of the hydrogen atoms on the alkoxy group are substituted with halogens, as defined herein. Exemplary haloalkoxy groups include 1,1,1-trichloroethoxy, 2-bromobutoxy, and the like.

"Hydroxy" refers to —OH.

"Oxo" refers to =O.

"Oxy" refers to $—O^-R_{77}^+$ wherein $R_{77}$ is an organic or inorganic cation.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, and the like.

"Hydroxyalkyl" refers to a hydroxy group, as defined herein, appended to an alkyl group, as defined herein.

"Nitrate" refers to —O—$NO_2$.

"Nitrite" refers to —O—NO.

"Thionitrate" refers to —S—$NO_2$.

"Thionitrite" and "nitrosothiol" refer to —S—NO.

"Nitro" refers to the group —$NO_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Amino" refers to —$NH_2$, an alkylamino group, a dialkylamino group, an arylamino group, a diarylamino group, an alkylarylamino group or a heterocyclic ring, as defined herein.

"Alkylamino" refers to $R_{50}NH—$, wherein $R_{50}$ is an alkyl group, as defined herein. Exemplary alkylamino groups include methylamino, ethylamino, butylamino, cyclohexylamino, and the like.

"Arylamino" refers to $R_{55}NH—$, wherein $R_{55}$ is an aryl group, as defined herein.

"Dialkylamino" refers to $R_{52}R_{53}N—$, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}N—$, wherein $R_{55}$ and $R_{60}$ are each independently an aryl group, as defined herein.

"Alkylarylamino or arylalkylamino" refers to $R_{52}R_{55}N—$, wherein $R_{52}$ is an alkyl group, as defined herein, and $R_{55}$ is an aryl group, as defined herein.

"Alkylarylalkylamino" refers to $R_{52}R_{79}N—$, wherein $R_{52}$ is an alkyl group, as defined herein, and $R_{79}$ is an arylalkyl group, as defined herein.

"Alkylcycloalkylamino" refers to $R_{52}R_{80}N—$, wherein $R_{52}$ is an alkyl group, as defined herein, and $R_{80}$ is an cycloalkyl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl, methylaminomethyl, and the like.

"Aminoaryl" refers to an aryl group to which is appended an alkylamino group, a arylamino group or an arylalkylamino group. Exemplary aminoaryl groups include anilino, N-methylanilino, N-benzylanilino, and the like.

"Thio" refers to —S—.

"Sulfinyl" refers to —S(O)—.

"Methanthial" refers to —C(S)—.

"Thial" refers to =S.

"Sulfonyl" refers to —$S(O)_2^-$.

"Sulfonic acid" refers to —$S(O)_2OR_{76}$, wherein $R_{76}$ is a hydrogen, an organic cation or an inorganic cation, as defined herein.

"Alkylsulfonic acid" refers to a sulfonic acid group, as defined herein, appended to an alkyl group, as defined herein.

"Arylsulfonic acid" refers to a sulfonic acid group, as defined herein, appended to an aryl group, as defined herein "Sulfonic ester" refers to —$S(O)_2OR_{58}$, wherein $R_{58}$ is an alkyl group, an aryl group, or an aryl heterocyclic ring, as defined herein.

"Sulfonamido" refers to —$S(O)_2$—$N(R_{51})(R_{57})$, wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}S—$, wherein $R_{50}$ is an alkyl group, as defined herein (preferably a lower alkyl group, as defined herein).

"Arylthio" refers to $R_{55}S—$, wherein $R_{55}$ is an aryl group, as defined herein.

"Arylalkylthio" refers to an aryl group, as defined herein, appended to an alkylthio group, as defined herein.

"Alkylsulfinyl" refers to $R_{50}$—S(O)—, wherein $R_{50}$ is an alkyl group, as defined herein.

"Alkylsulfonyl" refers to $R_{50}$—$S(O)_2$—, wherein $R_{50}$ is an alkyl group, as defined herein.

"Alkylsulfonyloxy" refers to $R_{50}$—$S(O)_2$—O—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—$S(O)_2$—, wherein $R_{55}$ is an aryl group, as defined herein.

"Arylsulfonyloxy" refers to $R_{55}$—$S(O)_2$—O—, wherein $R_{55}$ is an aryl group, as defined herein.

"Amidyl" refers to $R_{51}C(O)N(R_{57})$— wherein $R_{51}$ and $R_{57}$ are each independently a hydrogen atom, an alkyl group, an aryl group or an arylheterocyclic ring, as defined herein.

"Ester" refers to $R_{51}C(O)O$— wherein $R_{51}$ is a hydrogen atom, an alkyl group, an aryl group or an arylheterocyclic ring, as defined herein.

"Carbamoyl" refers to —O—C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to —C(O)O$R_{76}$, wherein $R_{76}$ is a hydrogen, an organic cation or an inorganic cation, as defined herein.

"Carbonyl" refers to —C(O)—.

"Alkylcarbonyl" refers to $R_{52}$—C(O)—, wherein $R_{52}$ is an alkyl group, as defined herein.

"Arylcarbonyl" refers to $R_{55}$—C(O)—, wherein $R_{55}$ is an aryl group, as defined herein.

"Arylalkylcarbonyl" refers to $R_{55}$—$R_{52}$—C(O)—, wherein $R_{55}$ is an aryl group, as defined herein, and $R_{52}$ is an alkyl group, as defined herein.

"Alkylarylcarbonyl" refers to $R_{52}$—$R_{55}$—C(O)—, wherein $R_{55}$ is an aryl group, as defined herein, and $R_{52}$ is an alkyl group, as defined herein.

"Heterocyclicalkylcarbonyl" refer to $R_{78}$C(O)— wherein $R_{78}$ is a heterocyclicalkyl group, as defined herein.

"Carboxylic ester" refers to —C(O)O$R_{58}$, wherein $R_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to —C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N($R_{59}$)—C(O)N($R_{51}$)($R_{57}$) wherein $R_{51}$, $R_{57}$, and $R_{59}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

The invention is based on the unexpected discovery that the novel aryl substituted compounds described herein are COX-2 selective inhibitors. These novel compounds can optionally be nitrosated and/or nitrosylated and can be used for the treatment or prevention of inflammation, pain and fever; treatment and/or improvement of the gastrointestinal properties of COX-2 selective inhibitors; facilitation of wound healing; for treatment and/or prevention of renal toxicity and cyclooxygenase-2 mediated disorders; and for the improvement of the cardiovascular profile of COX-2 selective inhibitors.

The COX-2 selective inhibitors, that are optionally nitrosated and/or nitrosylated, can be used alone or in conjunction with one or more compounds that donate, release or transfer nitric oxide and/or stimulate endogenous production of NO and/or EDRF in vivo and/or is a substrate for nitric oxide synthase, and/or with one or more therapeutic agents, such as for example, steroids, nonsterodal antiinflammatory compounds (NSAID), 5-lipoxygenase (5-LO) inhibitors, leukotriene $B_4$ (LTB$_4$) receptor antagonists, leukotriene $A_4$ (LTA$_4$) hydrolase inhibitors, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, analgesics, *Helicobacter pylori* inhibitors, proton pump inhibitors, isoprostane inhibitors, and mixtures thereof.

The invention describes novel COX-2 selective inhibitors that are compounds of Formula (I):

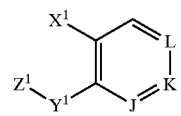

I wherein:
$X^1$ is:

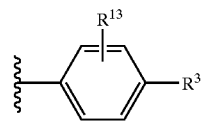

(a)

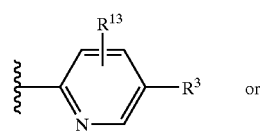

(b)

or

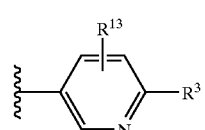

(c)

$Y^1$ is:
(a) —(CR$^1$R$^2$)$_a$—;
(b) —(CR$^1$R$^2$)$_b$—A$^1$—;
(c) —A$^1$—(CR$^1$R$^2$)$_b$—;
(d) —CR$^1$R$^2$—A$^1$—CR$^1$R$^2$—; or
(e) —CR$^1$=;

$Z^1$ is:
(a) mono-, di- or tri-substituted phenyl or 2-naphthyl, wherein the substituents are each independently:
(1) hydrogen;
(2) halo;
(3) lower alkyl;
(4) haloalkyl;
(5) alkylthio;
(6) —NR$^4$R$^5$;
(7) —C(O)-lower alkyl;
(8) —(CH$_2$)$_a$—C(O)O—R$^6$;
(9) —OR$^{11}$; or
(10) —(CR$_e$R$_f$)$_q$—U—V
(b) mono-, di- or tri-substituted cycloalkyl or heterocyclic ring, wherein the substituents are each independently:

(1) hydrogen;
(2) halo;
(3) lower alkyl;
(4) haloalkyl;
(5) alkylthio;
(6) —NR$^4$R$^5$;
(7) —C(O)-lower alkyl;
(8) —(CH$_2$)$_q$—C(O)O—R$^6$;
(9) —OR$^{11}$;
(10) —(CR$_e$R$_f$)$_q$—U—V;
(11) oxo; or
(12) thial;
(c) alkyl;
and the bond between Y$^1$ and Z$^1$ may be a single bond or a double bond such that the valencies are satisfied;

A$^1$ is:
(a) oxygen;
(b) thio;
(c) sulfinyl;
(d) sulfonyl; or
(e) —N(R$^{12}$)—;

—J=K—L= is:
(a) —CR$^7$=CR$^8$—N=;
(b) —CR$^7$=N—CR$^8$=;
(c) —N=CR$^7$—CR$^8$=;
(d) —CR$^8$=CR$^7$—N=;
(e) —CR$^8$=N—CR$^7$=;
(f) —N=CR$^8$—CR$^7$=;
(g) —N=N—CR$^7$=;
(h) —N=N—CR$^8$=;
(i) —CR$^7$=N—N=;
(j) —CR$^8$=N—N=;
(k) —N=CR$^7$—N=;
(l) —N=CR$^8$—N=;
(m) —CR$^7$=CR$^7$—CR$^8$=; or
(n) —CR$^7$=CR$^8$—CR$^{7'}$;

R$^1$ and R$^2$ are each independently:
(a) hydrogen;
(b) lower alkyl;
(c) substituted lower alkyl;
(d) lower alkoxy;
(e) lower haloalkyl; or
(f) halo; or R$^1$ and R$^2$ taken together are;
(a) oxo; or
(b) thial R$^3$ is:
(a) —S(O)$_2$—CH$_3$;
(b) —S(O)$_2$—NH$_2$;
(c) —S(O)$_2$—N(H)—C(O)—CF$_3$;
(d) —S(O)(NH)—NH$_2$;
(e) —S(O)(NH)—CH$_3$;
(f) —S(O)(NH)—N(H)—C(O)—CF$_3$;
(g) —S(O)$_2$-haloalkyl; or
(h) —CH$_2$—U—V R$^4$ is:
(a) hydrogen;
(b) substituted lower alkyl
(c) cycloalkyl;
(d) cycloalkylalkyl;
(e) lower alkenyl;
(f) lower alkoxy;
(g) alkylcarbonyl;
(h) carboxylic ester;
(i) carboxamido;
(j) arylcarbonyl;
(k) alkylsulfonyl;
(l) arylsufonyl;
(m) alkylarylsulfonyl; or
(n) arylalkylsulfonyl;

R$^5$ is:
(a) hydrogen; or
(b) lower alkyl; or

R$^4$ and R$^5$ taken together with the nitrogen to which they are attached form a heterocyclic ring;

R$^6$ is:
(a) lower alkyl; or
(b) arylalkyl;

R$^7$ is:
(a) hydrogen;
(b) halo;
(c) cyano;
(d) lower alkyl optionally substituted with:
   (1) halo;
   (2) alkoxy;
   (3) aryloxy;
   (4) cycloalkoxy;
   (5) ester;
   (6) carbamoyl;
   (7) —NR$^4$R$^5$;
   (8) phenyl optionally substituted with:
      (i) halo;
      (ii) hydroxy;
      (iii) lower alkyl; or
      (iv) alkoxy;
   (9) cyano;
   (10) —C(O)—H
   (11) alkylcarbonyl;
   (12) carboxylic ester;
   (13) carboxamido; or
   (14) heterocyclic ring;
(e) haloalkyl;
(f) lower alkenyl optionally substituted with:
   (1) cyano;
   (2) —C(O)—H
   (3) alkycarbonyl;
   (4) arylcarbonyl;
   (5) —C(O)-cycloalkyl;
   (6) —C(O)-heterocyclic ring;
   (7) carboxylic ester;
   (8) nitro; or
   (9) —NR$^4$R$^5$;
(g) nitro;
(h) —NR$^4$R$^5$;
(i) —S(O)$_o$R$^9$;
(j) —S(O)$_o$NR$^5$R$^{10}$;
(k) —C(O)—H;
(l) alkylcarbonyl;
(m) arylcarbonyl;
(n) —C(O)-cycloalkyl;
(o) —C(O)-heterocyclic ring;
(p) carboxylic ester;
(q) carboxamido;
(r) alkoxy;
(s) aryloxy;
(t) cycloalkoxy;
(u) ester;
(v) carbamoyl; or
(w) —D R$^{7'}$ is:
(a) hydrogen;
(b) halo; or (c) —D R$^8$ is:
  (a) hydrogen;
  (b) halo;
  (c) lower alkyl
  (d) lower alkoxy;
  (e) lower haloalkyl;
  (f) lower alkylthio; or
  (g) —D alternatively, R$^7$ and R$^8$ when substituents on adjacent carbon atoms may be taken together with the carbons to which they are attached to form an aromatic or non-aromatic 5–7 membered carbocyclic or heterocyclic ring system containing from 1–3 heteroatoms selected from nitrogen, oxygen or sulfur. All carbons in the 5–7 membered carbocyclic or heterocyclic ring system are substituted with sufficient R$^7$ or R$^8$ variables to satisfy the tetravalency of the ring carbon atoms.

R$^9$ is:
  (a) lower alkyl;
  (b) haloalkyl;
  (c) phenyl; or
  (d) benzyl;

R$^{10}$ is:
  (a) hydrogen;
  (b) lower alkyl;
  (c) aryl;
  (d) cycloalkyl;
  (e) cycloalkylalkyl;
  (f) lower alkenyl; or
  (g) lower alkoxy;

R$^{11}$ is:
  (a) lower alkyl;
  (b) lower haloalkyl;
  (c) alkoxyalkyl;
  (d) alkylcarbonyl;
  (e) arylalkylcarbonyl;
  (f) carboxamido; or
  (g) arylcarbonyl;

R$^{12}$ is:
  (a) lower alkyl;
  (b) hydrogen; or
  (c) —C(O)H;

R$^{13}$ is:
  (a) hydrogen;
  (b) halogen;
  (c) lower alkyl;
  (d) lower alkoxy; or
  (e) lower haloalkyl;

a is an integer equal to 1 or 3;

b is an integer equal to 2 or 3;

o is an integer from 0–2;

D is —W$_k$—E$_l$—(C(R$_e$)(R$_f$))$_p$—E$_c$—(C(R$_e$)(R$_f$))$_x$—W$_d$—(C(R$_e$)(R$_f$))$_y$—W$_i$—E$_j$—W$_g$—(C(R$_e$)(R$_f$))$_z$—U—V;

wherein c, d, g, i, j, k and l are each independently an integer from 0 to 3;

p, x, y and z are each independently an integer from 0 to 10;

W at each occurrence is independently:
  (a) —C(O)—;
  (b) —C(S)—;
  (c) —T—;
  (d) —(C(R$_e$)(R$_f$))$_h$—;
  (e) alkyl;
  (f) aryl;
  (g) heterocyclic ring;
  (h) arylheterocyclic ring, or
  (i) —(CH$_2$CH$_2$O)$_q$—;

E at each occurrence is independently:
  (a) —T—;
  (b) alkyl;
  (c) aryl;
  (d) —(C(R$_e$)(R$_f$))$_h$—;
  (e) heterocyclic ring;
  (f) arylheterocyclic ring; or
  (g) —(CH$_2$CH$_2$O)$_q$—;

h is an integer form 1 to 10;

q is an integer from 1 to 5;

R$_e$ and R$_f$ are each independently:
  (a) hydrogen;
  (b) alkyl;
  (c) cycloalkoxy;
  (d) halogen;
  (e) hydroxy;
  (f) hydroxyalkyl;
  (g) alkoxyalkyl;
  (h) arylheterocyclic ring;
  (i) alkylaryl;
  (j) cycloalkylalkyl;
  (k) heterocyclicalkyl;
  (l) alkoxy;
  (m) haloalkoxy;
  (n) amino;
  (o) alkylamino;
  (p) dialkylamino;
  (q) arylamino;
  (r) diarylamino;
  (s) alkylarylamino;
  (t) alkoxyhaloalkyl;
  (u) haloalkoxy;
  (v) sulfonic acid;
  (w) alkylsulfonic acid;
  (x) arylsulfonic acid;
  (y) arylalkoxy;
  (z) alkylthio;
  (aa) arylthio;
  (bb) cyano;
  (cc) aminoalkyl;
  (dd) aminoaryl;
  (ee) alkoxy;
  (ff) aryl;
  (gg) arylalkyl;
  (hh) alkylaryl;
  (ii) carboxamido;
  (jj) alkylcarboxamido;
  (kk) arylcarboxamido;
  (ll) amidyl;
  (mm) carboxyl;
  (nn) carbamoyl;
  (oo) alkylcarboxylic acid;
  (pp) arylcarboxylic acid;
  (qq) alkylcarbonyl;
  (rr) arylcarbonyl;
  (ss) ester;
  (tt) carboxylic ester;
  (uu) alkylcarboxylic ester;
  (vv) arylcarboxylic ester;
  (ww) haloalkoxy;
  (xx) sulfonamido;
  (yy) alkylsulfonamido;
  (zz) arylsulfonamido;

(aaa) sulfonic ester;
(bbb) carbamoyl;
(ccc) urea;
(ddd) nitro; or
(eee) —(C($R_e$)($R_f$))$_k$—U—V; or $R_e$ and $R_f$ taken together with the carbon to which they are attached are:
  (a) oxo;
  (b) thial;
  (c) aryl;
  (d) heterocyclic ring;
  (e) cycloalkyl group; or
  (f) bridged cycloalkyl group;

k is an integer from 1 to 2;

U is:
  (a) oxygen;
  (b) sulfur; or
  (c) —N($R_a$)$R_i$—;

V is:
  (a) —NO; or
  (b) —$NO_2$;

T at each occurrence is independently:
  (a) a covalent bond,
  (b) carbonyl,
  (c) an oxygen,
  (d) —S(O)$_o$—; or
  (e) —N($R_a$)$R_i$—;

$R_a$ is:
  (a) a lone pair of electron;
  (b) hydrogen; or
  (c) lower alkyl;

$R_i$ is:
  (a) hydrogen;
  (b) alkyl;
  (c) aryl;
  (d) alkylcarboxylic acid;
  (e) aryl carboxylic acid;
  (f) alkylcarboxylic ester;
  (g) arylcarboxylic ester;
  (h) alkylcarboxamido;
  (i) arylcarboxamido;
  (j) alkylaryl;
  (k) alkylsulfinyl;
  (l) alkylsulfonyl;
  (m) arylsulfinyl;
  (n) arylsulfonyl;
  (o) sulfonamido;
  (p) carboxamido;
  (q) carboxylic ester;
  (r) aminoalkyl;
  (s) aminoaryl;
  (t) —$CH_2$—C(U—V)($R_e$)($R_f$); or
  (u) —($N_2O_2$—)$^-$·$M^+$, wherein $M^+$ is an organic or inorganic cation.

In cases where $R^e$ and $R^f$ are a heterocyclic ring or $R_e$ and $R_f$ taken together with the carbon atoms to which they are attached are a heterocyclic ring, then $R_i$ can be a substituent on any disubstituted nitrogen contained within the radical where $R_i$ is as defined herein.

In cases where multiple designations of variables that are in sequence are selected as a "covalent bond" or the integer selected is 0, the intent is to denote a single covalent bond connecting one radical to another. For example, $E_0$ would denote a covalent bond, while $E_2$ denotes (E—E) and (C($R_e$)($R_f$))$_2$ denotes —C($R_e$)($R_f$)—C($R_e$)($R_f$)—.

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. The invention includes within its scope all such isomers and mixtures thereof.

Another aspect of the invention provides processes for making the novel compounds of the invention and to the intermediates useful in such processes. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known for protecting thiol and alcohol groups against undesirable reactions during a synthetic procedure and many such protecting groups are known and described by, for example, Greene and Wuts, *Protective Groups in Organic Synthesis*, Third Edition, John Wiley & Sons, New York (1999).

The chemical reactions described herein are generally disclosed in terms of their broadest application for the preparation of the compounds of this invention. The chemical reactions are described by, for example, Smith and March, *March's Advanced Organic Chemistry, Reactions, Mechanisms and Structure*, Fifth Edition, John Wiley & Sons, New York (2001) and by Larock, *Comprehensive Organic Transformations*, VCH Publishers, Inc. (1989). The compounds of the invention can be synthesized in a number of ways well known to one skilled in the art of organic synthesis. The compounds can be synthesized using the methods described herein, together with synthetic methods known in the art of synthetic organic chemistry, or by convention modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials. Methods for the preparation of the compounds, include, but are not limited to, those described below. All references cited herein are hereby incorporated herein by reference in their entirety.

Compounds of Formula (I) wherein $X^1$ is a 4-methylsulfonylphenyl, $Y^1$ is a methylene, hydroxymethylene or carbonyl, $Z^1$ is a substituted phenyl or 2-naphthyl, or heteroaryl and —J═K—L═ is as defined herein, can be prepared following the general method shown in Scheme 1.

Scheme 1

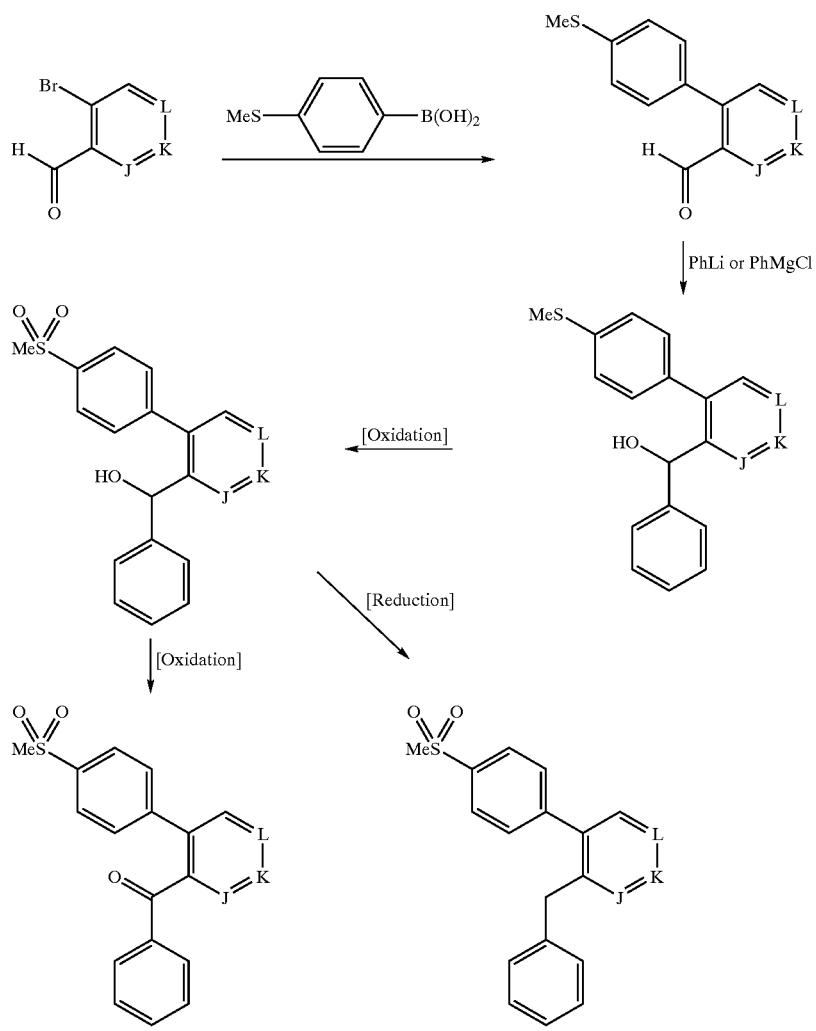

Coupling of a suitably substituted 4-methylthio-phenylboronic acid with an ortho-bromo, ortho-chloro or ortho-trifluoroacetyl aryl carbaldehyde using methodology introduced by Suzuki (Suzuki et al., *J. Am. Chem. Soc.*, 11:513 (1989), and Kalinin, *Russ. Chem. Rev.*, 60:173 (1991)) gives the phenyl substituted aryl carbaldehyde. Suitable solvents for this coupling include, but are not limited to, toluene, dimethylformamide, dioxane and ethanol. The reaction is carried out in the presence of a palladium catalyst, for example, tetrakis triphenylphosphine palladium or bis(triphenylphosphine)palladium dichloride. Reaction of the carbaldehyde with a substituted aryl lithium or aryl Grignard reagent gives the benzilic alcohol. Oxidation of the methylthio group to the corresponding methylsulfonyl group gives compounds of Formula (I). This oxidation can be accomplished using any reagent known in the art for the oxidation of mercaptans to sulfones. Examples of such reagents include, but are not limited to, OXONE® in methanol-water (Trost et. al., *Tet. Lett.*, 22:1287, (1981)), hydrogen peroxide, m-chloroperbenzoic acid, or magnesium salt of monoperoxyphthalic acid. Oxidation of the alcohol moiety gives additional compounds of Formula (I). This oxidation can be accomplished using any reagent known in the art for the oxidation of benzilic alcohols to benzilic ketones. Examples of such reagents include, but are not limited to, pyridinium chlorochromate or pyridinium dichromate in methylene chloride and sulfur trioxide-pyridine complex with dimethyl sulfoxide (Parikh-Doering Reagent: *J. Am. Chem. Soc.*, 89:5505 (1967)). Reduction of the alcohol moiety gives additional compounds of Formula (I). This reduction can be accomplished using any reagent known in the art for the reduction of benzilic alcohols. Examples of such reagents include, but are not limited to, hydrogen and a palladium catalyst such as palladium on charcoal, triethylsilane and trifluoroacetic acid or trifluoroacetic acid and sodium borohydride.

Compounds of Formula (I), wherein $X^1$ is a 4-methylsulfonylphenyl, $Y^1$ is a methylidene or a methylene, $Z^1$ is a cycloalkyl or alkyl group and q and —J═K—L═ are as defined herein, can be prepared following the general method shown in Scheme 2.

Scheme 2

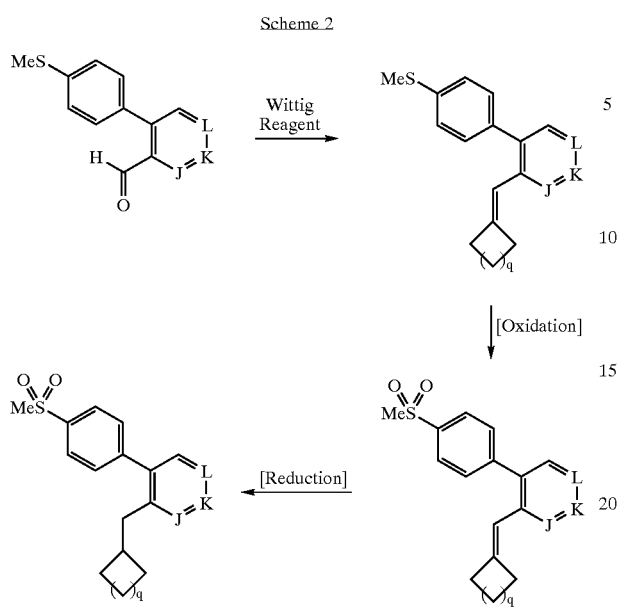

Wittig coupling of the phenyl substituted aryl carbaldehydes with a cycloalkyl phosphorane, an alkyl phosphorane or a phosphonate anion gives the substituted alkenes. Phosphoranes may be prepared from the corresponding phosphonium salts by treatment with a base. Examples of bases used to prepare phosphoranes from phosphonium salts include, but are not limited to, an alkyl lithium, sodium hydride, lithium diisopropyl amide, or sodium alkoxide. Phosphonium salts are prepared from a phosphine and a cycloalkyl or alkyl halide. Phosphonates may be prepared from a phosphite and a cycloalkyl or alkyl halide that may be converted to the phosphonate anion by treatment with a strong base, such as, for example, lithium diisopropyl amide or lithium hexamethyldisilazide. Oxidation of the methylthio group to the corresponding methylsulfonyl group as described herein gives compounds of Formula (I). Reduction of the double bond gives additional compounds of Formula (I). This reduction can be accomplished using any reagent known in the art for the reduction of alkenes. Examples of such reagents include, but are not limited to, hydrogen and a palladium catalyst such as palladium on charcoal.

Compounds of Formula (I) wherein $X^1$ is a 4-methylsulfonylphenyl, $Y^1$ is a methylene, hydroxymethylene or carbonyl, $Z^1$ is a substituted phenyl or 2-naphthyl, or heteroaryl and —J=K—L= is selected such that it forms a substituted 2H-benzo(d)1,3-dioxolene ring, can be prepared following the general method shown in Scheme 3.

Scheme 3

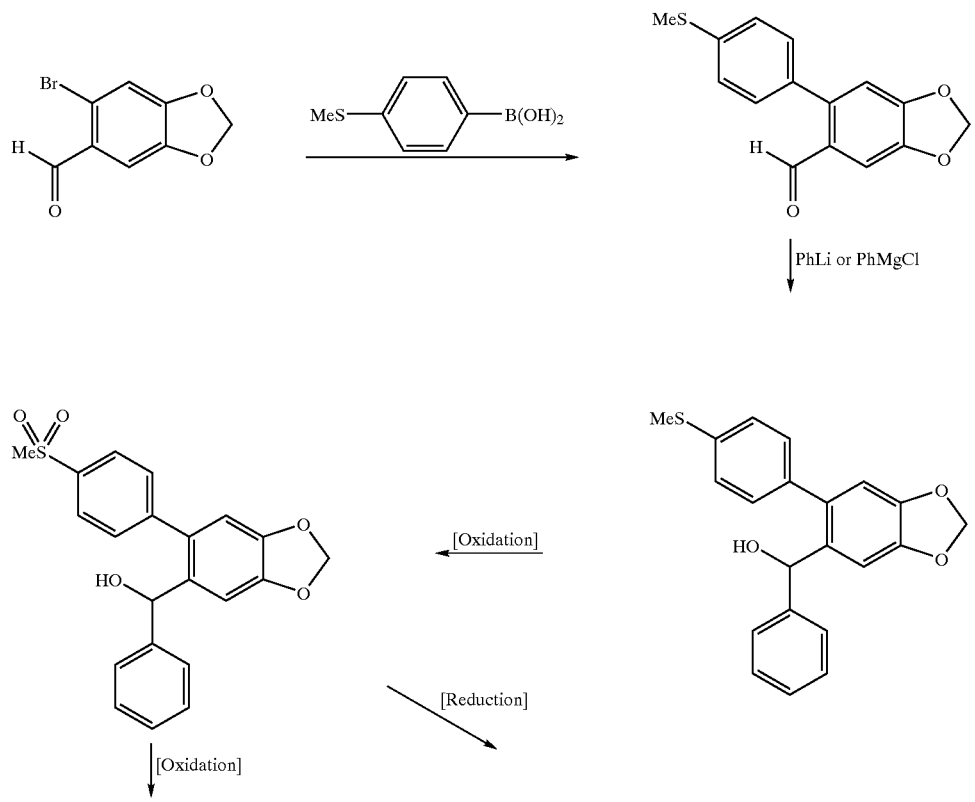

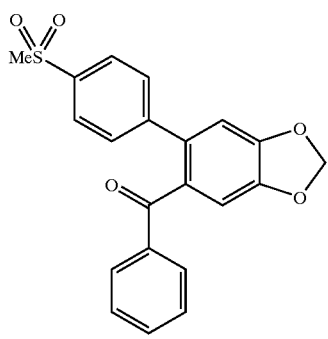
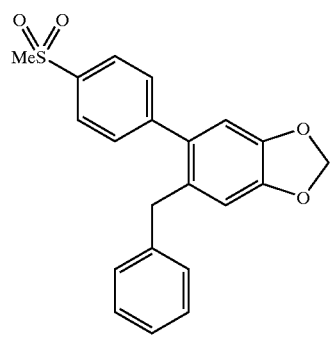

Suzuki coupling of 6-bromo-2H-benzo(d)1,3-dioxolene-5-carbaldehyde (Khanapure et. al., *J. Org. Chem.*, 55:1471 (1990)) with 4-methylthiophenylboronic acid using conditions described herein gives the biaryl product. Reaction of the carbaldehyde with a substituted aryl lithium or aryl Grignard reagent gives the benzilic alcohol. Oxidation of the methylthio group to the corresponding methylsulfonyl group using the conditions described herein gives compounds of Formula (I). Oxidation of the alcohol using the conditions described herein gives additional compounds of Formula (I). Reduction of the alcohol using the conditions described herein gives additional compounds of Formula (I).

Compounds of Formula (I), wherein $X^1$ is a 4-methylsulfonylphenyl, $Y^1$ is a methylidene or a methylene, $Z^1$ is a cycloalkyl or alkyl group, q is as defined herein and —J═K—L═ is selected such that it forms a substituted 2H-benzo(d)1,3-dioxolene ring, can be prepared following the general method shown in Scheme 4.

Wittig coupling of 6-(4-methylthiophenyl)-2H-benzo(d)1,3-dioxolene-5-carbaldehyde using the reagents and conditions described herein gives the substituted alkenes. Oxidation of the methylthio group to the corresponding methylsulfonyl group as described herein gives compounds of Formula (I). Reduction of the double bond as described herein gives additional compounds of Formula (I).

Compounds of Formula (I) wherein $X^1$ is a 4-methylsulfonylphenyl, $Y^1$ is a methylene, hydroxymethylene or carbonyl, $Z^1$ is a substituted phenyl or 2-naphthyl, or heteroaryl, R is a D group or a precursor to a D group, D is as defined herein and —J═K—L═ is selected such that it forms a substituted benzoxazole ring, can be prepared following the general method shown in Scheme 5.

Scheme 4

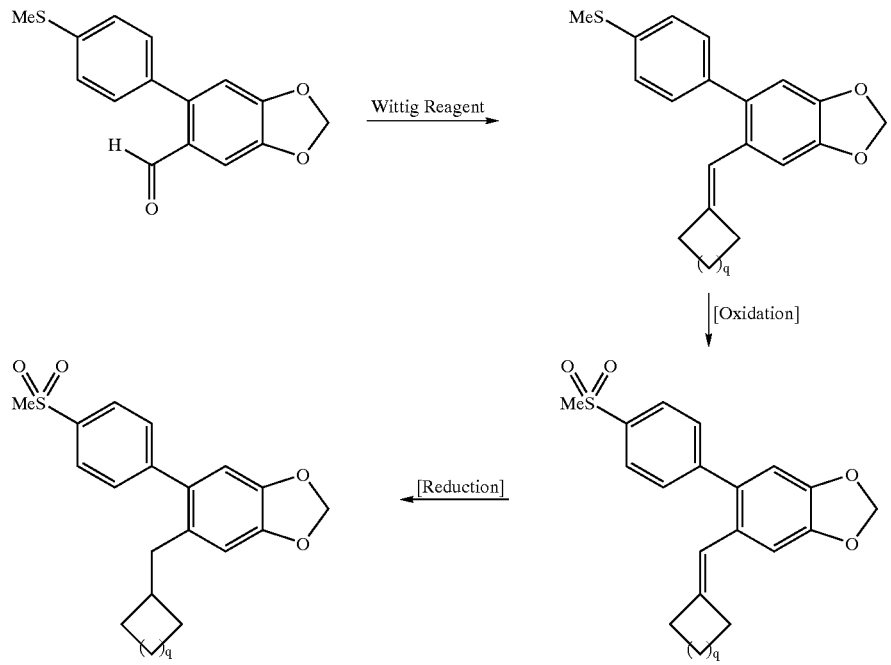

Scheme 5
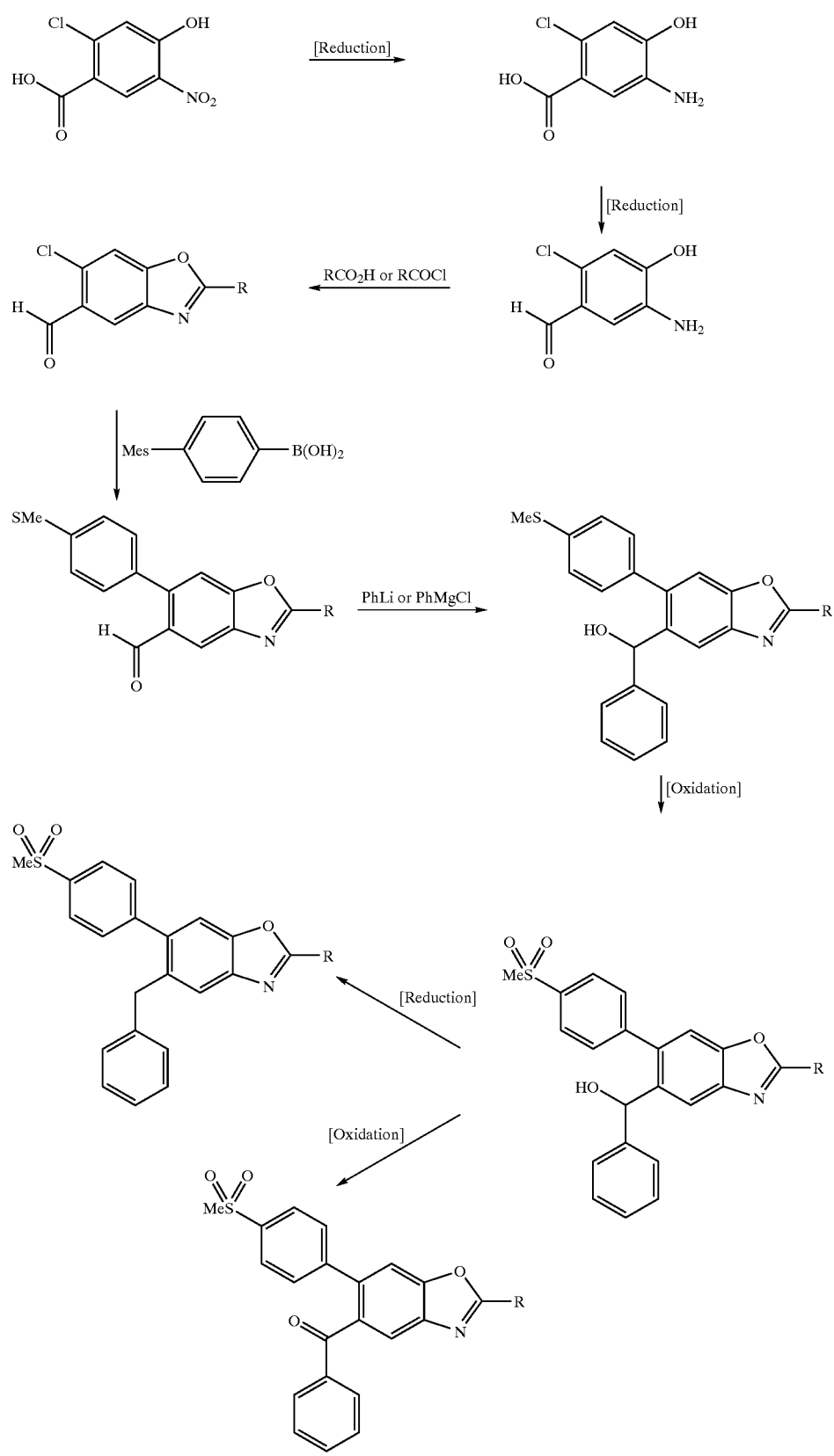

Reduction of the nitro group of 2-chloro-4-hydroxy-5-nitrobenzoic acid (Goldstein et. al. *Helv. Chim. Acta.*, 20:1407 (1937)) gives the amine. This reduction can be accomplished using any reagent known in the art for the reduction of aromatic nitro compounds to amines. Examples of such reagents include, but are not limited to, hydrogenation in the presence of a catalyst such as palladium or platinum on charcoal, zinc, tin or iron and hydrochloric acid in a refluxing aqueous or alcoholic solvent or sodium borohydride in the presence of a catalyst such as nickel or cobalt chloride. Reduction of the carboxylic acid gives the benzilic aldehyde. This reduction can be accomplished using any reagent known in the art for the reduction of carboxylic acids to alcohols with a subsequent oxidation to the carbaldehyde. Examples of such reagents include, but are not limited to, borane in tetrahydrofuran, lithium aluminum hydride in ether or diisobutylaluminum hydride in tetrahydrofuran, hexanes or toluene. Subsequent oxidation to the aldehyde can be accomplished using any reagent known in the art for the oxidation of benzilic alcohols to benzilic aldehydes. Examples of such reagents include, but are not limited to, pyridinium chlorochromate or pyridinium dichromate in methylene chloride orsulfur trioxide-pyridine complex with dimethyl sulfoxide Formation of the substituted benzoxazole ring can be accomplished by treatment of the substituted aniline with a carboxylic acid or carboxylic acid chloride under acidic conditions with the removal of the water formed. Examples of such reagents and conditions used to catalyze the formation of the ring include, but are not limited to, polyphosphoric acid at 100–150° C., trimethylsilyl polyphosphate or concentrated sulfuric acid in benzene under reflux with azeotropic removal of the water generated. Suzuki coupling of the chloro substituted benzoxazole with 4-methylthiopheny boronic acid using conditions described herein gives the biaryl product. Reaction of the carbaldehyde with a substituted aryl lithium or aryl Grignard reagent gives the benzilic alcohol. Oxidation of the methylthio group to the corresponding methylsulfonyl group using the conditions described herein gives compounds of Formula (I). Oxidation of the alcohol using the conditions described herein gives additional compounds of Formula (I). Reduction of the alcohol using the conditions described herein gives additional compounds of Formula (I).

Compounds of Formula (I), wherein $X^1$ is a 4-methylsulfonylphenyl, $Y^1$ is a methylidene or a methylene, $Z^1$ is a cycloalkyl or alkyl group, R is a D group or a precursor to a D group, wherein D and q are as defined herein and —J═K—L═ is selected such that it forms a substituted benzoxazole ring, can be prepared following the general method shown in Scheme 6.

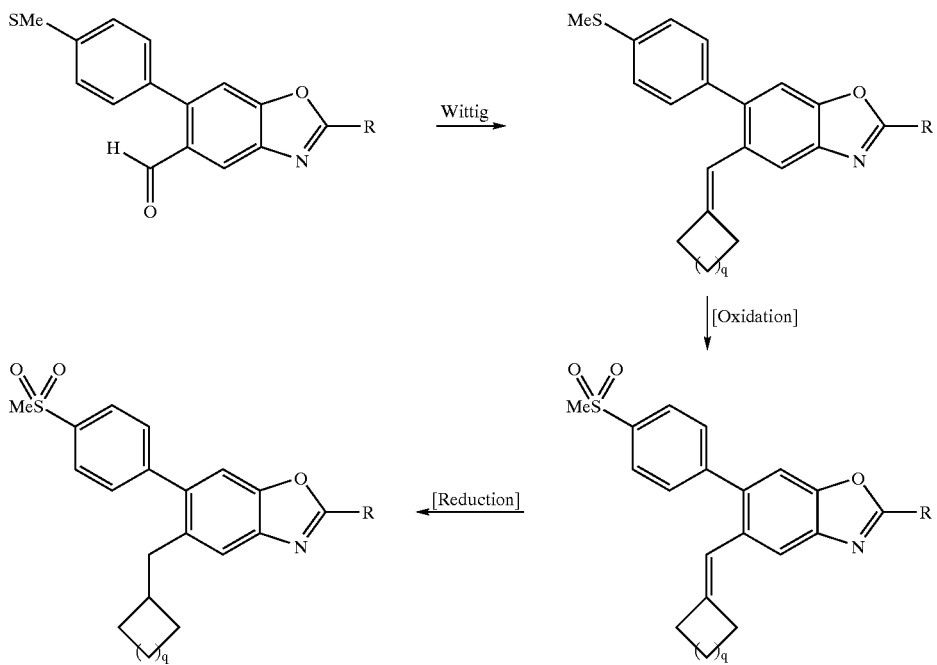

Scheme 6

Wittig coupling of 2-substituted-6-(4-methylthiophenyl)benzoxazole-5-carbaldehyde using the reagents and conditions described herein gives the substituted alkenes. Oxidation of the methylthio group to the corresponding methylsulfonyl group using the conditions described herein gives compounds of Formula (I). Reduction of the double bond using the conditions described herein gives additional compounds of Formula (I).

Compounds of Formula (I) wherein $X^1$ is a 4-methylsulfonylphenyl, $Y^1$ is a methylene, hydroxymethylene or carbonyl, $Z^1$ is a substituted phenyl or 2-naphthyl, or heteroaryl, R is a D group or a precursor to a D group, wherein D and q are as defined herein and —J═K—L═ is selected such that it forms a substituted benzthiazole ring, can be prepared following the general method shown in Scheme 7.

Scheme 7
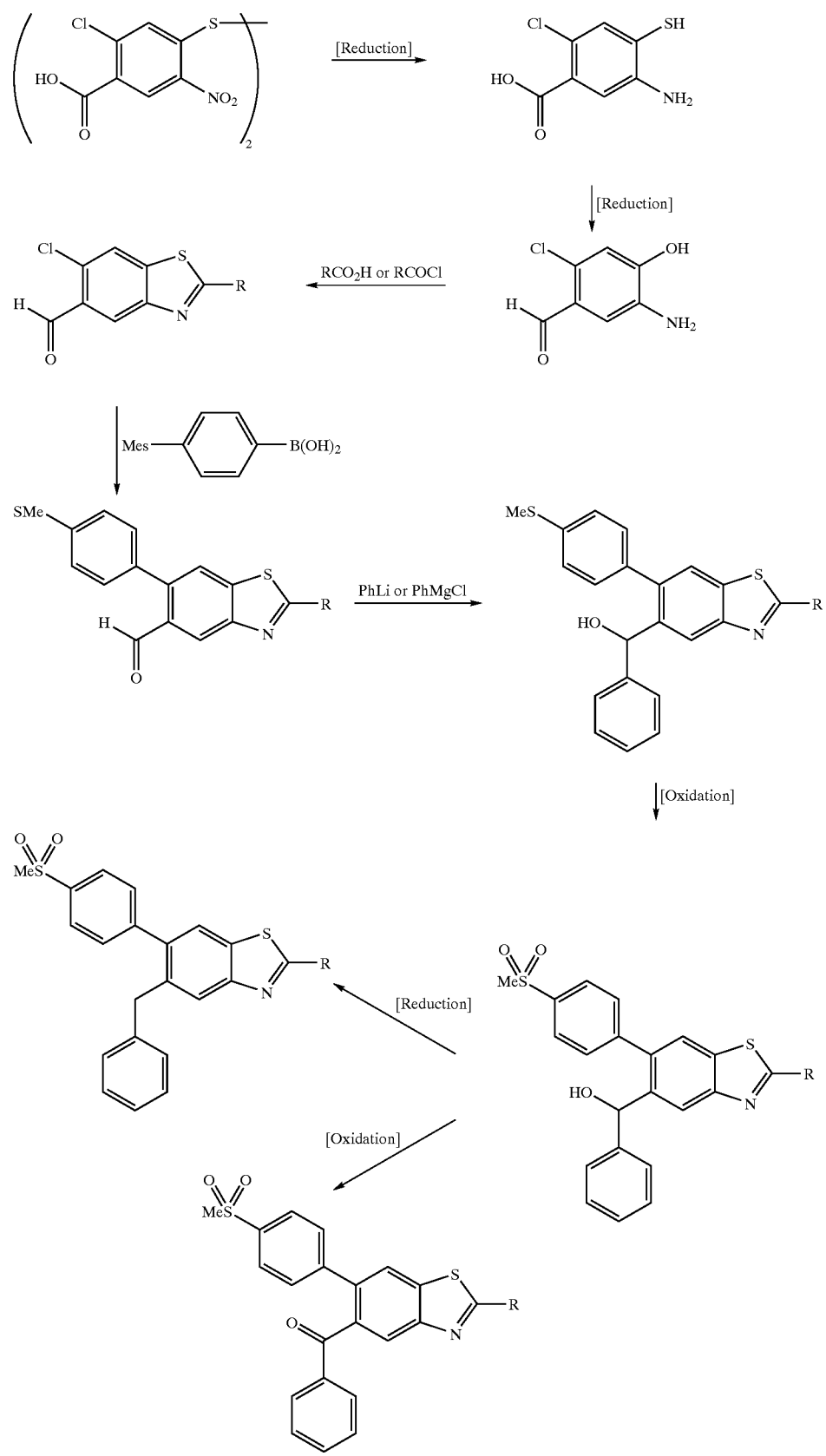

Reduction of the nitro groups of 2,2'-dichloro-5,5'-dinitro4,4'-disulfanediyl-di-benzoic acid (Goldstein et. al. *Helv. Chim. Acta.*, 21:1513 (1938)) using the reagents and conditions described herein gives the diamine. Reduction of the disulfide gives the thiol. This reduction can be accomplished using any reagent known in the art for the reduction of disulfides to thiols. Examples of such reagents include, but are not limited to, zinc and acetic acid or dilute mineral acid or triphenylphosphine in water. Conversion of the carboxylic acid to the carboxylic acid chloride can be accomplished using any reagent known in the art for the conversion of carboxylic acids to carboxylic acid chlorides. Examples of such reagents include, but are not limited to, thionyl chloride or oxalyl chloride with or without a catalytic amount of dimethylforamide, phosphorus pentachloride or triphenylphosphine and carbon tetrachloride. Reduction of the carboxylic acid chloride gives the aldehyde. This reduction can be accomplished using any reagent known in the art for the conversion of carboxylic acid chlorides directly to aldehydes. Examples of such reagents include, but are not limited to, catalytic hydrogenation with palladium on barium sulfate (Rosenmund reduction), sodium borohydride and cadmium chloride or lithium tri-tert-butoxyaluminum hydride in diglyme at −78° C. Formation of the substituted benzthiazole ring can be accomplished by treatment of the substituted aniline with a carboxylic acid or carboxylic acid chloride under acidic conditions with removal of the water formed. Examples of such reagents and conditions used to catalyze the formation of the ring include, but are not limited to, polyphosphoric acid at 100–150° C., trimethylsilyl polyphosphate or concentrated sulfuric acid in benzene under reflux with azeotropic removal of the water generated. Suzuki coupling of the chloro-substituted benzthiazole with 4-methylthiophenylboronic acid using conditions described herein gives the biaryl product. Reaction of the carbaldehyde with a substituted aryl lithium or aryl Grignard reagent gives the benzilic alcohol. Oxidation of the methylthio group to the corresponding methylsulfonyl group using the conditions described herein gives compounds of Formula (I). Oxidation of the alcohol using the conditions described herein gives additional compounds of Formula (I). Reduction of the alcohol using the conditions described herein gives additional compounds of Formula (I).

Compounds of Formula (I), wherein $X^1$ is a 4-methylsulfonylphenyl, $Y^1$ is a methylidene or a methylene, $Z^1$ is a cycloalkyl or alkyl group, R is a D group or a precursor to a D group, wherein D and q are as defined herein and —J═K—L═ is selected such that it forms a substituted
benzthiazole ring, can be prepared following the general method shown in Scheme 8.

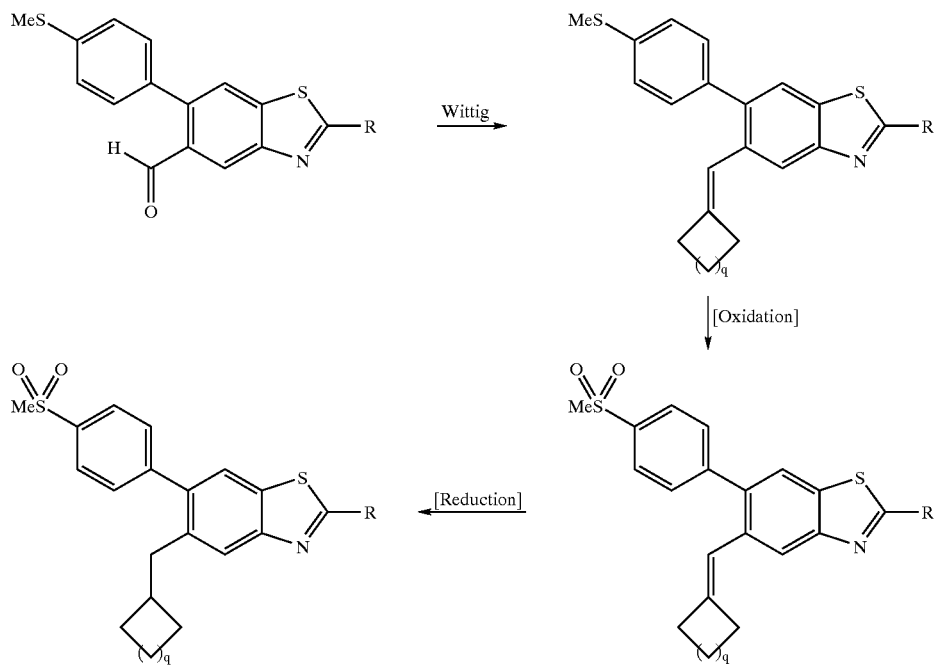

Scheme 8

Wittig coupling of 2-substituted-6-(4-methylthiophenyl)benzthiazole-5-carbaldehyde using the conditions described herein gives the substituted alkenes. Oxidation of the methylthio group to the corresponding methylsulfonyl group using the conditions described herein givess compounds of Formula (I). Reduction of the double bond using the conditions described herein gives additional compounds of Formula (I).

Compounds of Formula (I) wherein $X^1$ is a 4-methylsulfonylphenyl, $Y^1$ is a methylene, hydroxymethylene or carbonyl, $Z^1$ is a substituted phenyl, 2-naphthyl, or heteroaryl, R is a D group or a precursor to a D group, D is as defined herein and —J═K—L═ is selected such that it forms a substituted benzoxazole ring, can be prepared following the general method shown in Scheme 9.

Scheme 9
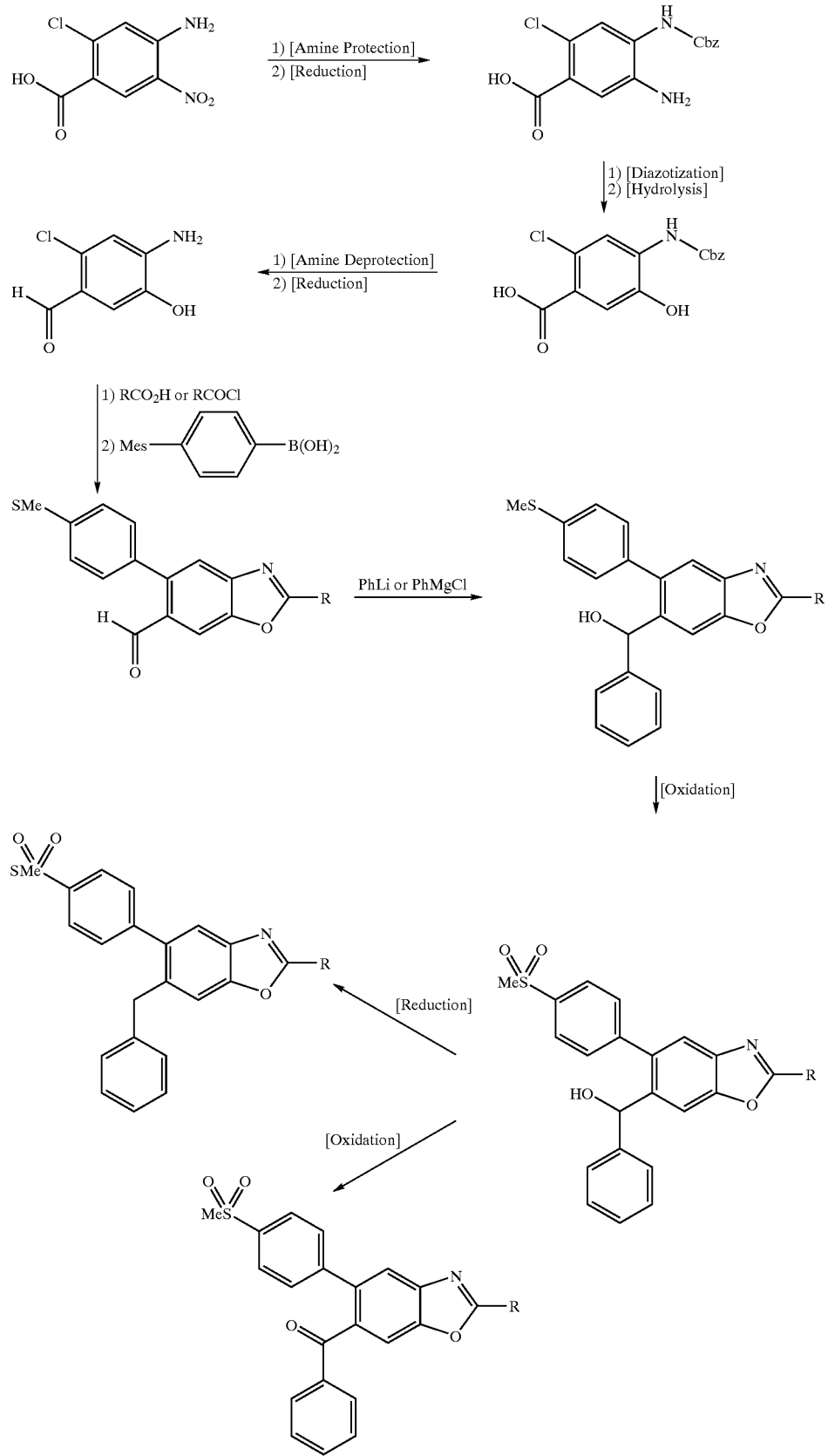

Protection of the of the amine group of 4-amino-2-chloro-5-nitro-benzoic acid (Goldstein et. al., *Helv. Chim. Acta.*, 20:1407 (1937)) as the N-carbobenzyloxy derivative can be accomplished by reacting the amine with benzyl chloroformate. Reduction of the nitro group of 2-chloro-5-nitro-4-((phenylmethoxy)carbonylamino)benzoic acid using the reagents and conditions described herein gives the amine. Treatment of the amine with nitrous acid followed by conversion of the diazonium group to a hydroxy group gives the phenol. Conversion of the aromatic primary amine to the diazonium salt can be accomplished using any reagent known in the art for the conversion of anilines to diazonium salts, such as, for example, sodium nitrite and sulfuric acid to form the diazonium salt. Treatment of the diazonium salt with aqueous boiling dilute sulfuric acid gives the phenol. Alternatively, treatment of an aqueous solution of the diazonium salt containing an excess of cupric nitrate with cuprous oxide gives the phenol. Deprotection of carbamate protecting group by hydrogenation in the presence of a catalyst, such as, for example, palladium on carbon gives the amine. Reduction of the carboxylic acid or acid chloride to the benzilic alcohol and the oxidizing the benzilic alcohol to the aldehyde or, alternatively, reducing the carboxylic acid via the carboxylic acid chloride directly to the carbaldehyde using the conditions described herein gives the aldehyde. Formation of the benzoxazole ring using the conditions described herein, followed by Suzuki coupling of the chloro substituted benzoxazole with 4-methylthiophenylboronic acid using the conditions described herein gives the biaryl product. Reaction of the carbaldehyde with a substituted aryl lithium or aryl Grignard reagent gives the benzilic alcohol. Oxidation of the methylthio group to the corresponding methylsulfonyl group using the conditions described herein gives compounds of Formula (I). Oxidation of the alcohol using the conditions described herein gives additional compounds of Formula (I). Reduction of the alcohol using the conditions described herein gives additional compounds of Formula (I).

Compounds of Formula (I), wherein $X^1$ is a 4-methylsulfonylphenyl, $Y^1$ is a methylidene or a methylene, $Z^1$ is a cycloalkyl or alkyl group, R is a D group or a precursor to a D group, wherein D and q are as defined herein and —J=K—L= is selected such that it forms a substituted benzoxazole ring, can be prepared following the general method shown in Scheme 10.

Scheme 10

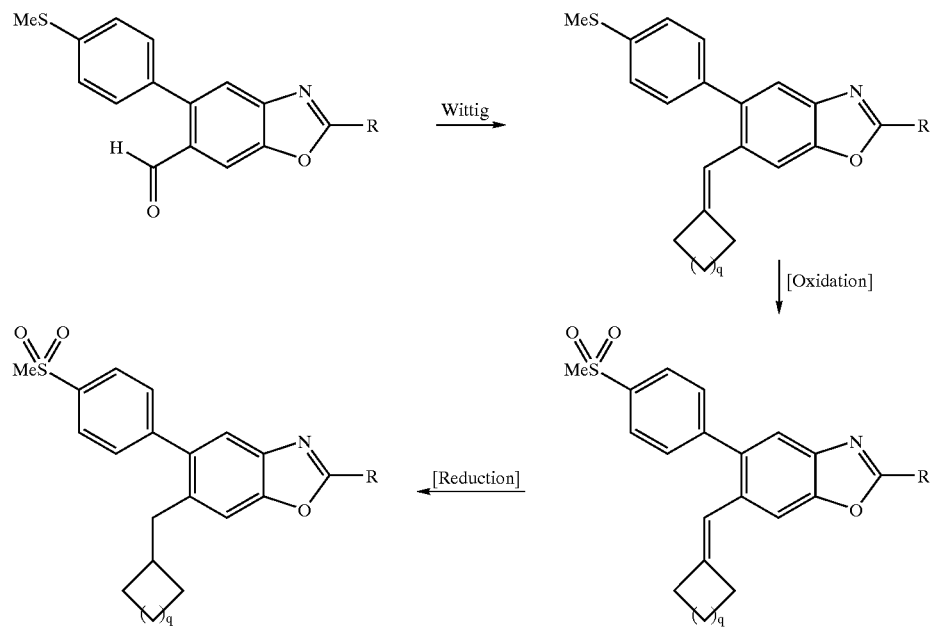

Wittig coupling of the 2-substituted 5-(4-methylthiophenyl)benzoxazole-6-carbaldehyde using the conditions described herein gives the substituted alkenes. Oxidation of the methylthio group to the corresponding methylsulfonyl group using the conditions described herein gives compounds of Formula (I). Reduction of the double bond using the conditions described herein gives additional compounds of Formula (I).

The compounds of Formula (I) can be nitrosated and/or nitrosylated through one or more sites such as oxygen, sulfur and/or nitrogen using the methods described in the examples herein and using conventional methods known to one skilled in the art. For example, known methods for nitrosating and nitrosylating compounds are described in U.S. Pat. Nos. 5,380,758 and 5,703,073; WO 97/27749; WO 98/19672; and Oae et al, *Org. Prep. Proc. Int.*, 15(3):165–198 (1983), the disclosures of each of which are incorporated by reference herein in their entirety. The methods of nitrosating and/or nitrosylating the compounds described in the examples herein and in these references can be applied by one skilled in the art to produce any of the nitrosated and/or nitrosylated compounds of Formula (I) described herein. The nitrosated and/or nitrosylated compounds of Formula (I) (i.e. nitrosated and/or nitrosylated COX-2 selective inhibitors) of the invention donate, transfer or release a biologically active form of nitrogen monoxide (nitric oxide).

Nitrogen monoxide can exist in three forms: NO− (nitroxyl), NO· (uncharged nitric oxide) and NO+

(nitrosonium). NO· is a highly reactive short-lived species that is potentially toxic to cells. This is critical because the pharmacological efficacy of NO depends upon the form in which it is delivered. In contrast to the nitric oxide radical (NO·), nitrosonium (NO$^+$) does not react with $O_2$ or $O_2^-$ species, and functionalities capable of transferring and/or releasing NO$^+$ and NO– are also resistant to decomposition in the presence of many redox metals. Consequently, administration of charged NO equivalents (positive and/or negative) is a more effective means of delivering a biologically active NO to the desired site of action.

Compounds contemplated for use in the invention (e.g., COX-2 selective inhibitors that can be optionally nitrosated and/or nitrosylated) are, optionally, used in combination with nitric oxide and compounds that release nitric oxide or otherwise directly or indirectly deliver or transfer a biologically active form of nitrogen monoxide to a site of its intended activity, such as on a cell membrane in vivo.

The term "nitric oxide" encompasses uncharged nitric oxide (NO·) and charged nitrogen monoxide species, preferably charged nitrogen monoxide species, such as nitrosonium ion (NO$^+$) and nitroxyl ion (NO–). The reactive form of nitric oxide can be provided by gaseous nitric oxide. The nitrogen monoxide releasing, delivering or transferring compounds have the structure F—NO, wherein F is a nitrogen monoxide releasing, delivering or transferring moiety, and include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexeneamide (FK-409), (E)-alkyl-2-((E)-hydroxyimino)-5-nitro-3-hexeneamines, N-((2Z, 3E)-4-ethyl-2-(hydroxyimino)-6-methyl-5-nitro-3-heptenyl)-3-pyridinecarboxamide (FR 146801), nitrosoamines, furoxans as well as substrates for the endogenous enzymes which synthesize nitric oxide. NONOates include, but are not limited to, (Z)-1-(N-methyl-N-(6-(N-methyl-ammoniohexyl)amino))diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-(N-(3-aminopropyl)-N-(4-(3-aminopropylammonio) butyl)-amino)diazen-1-ium-1,2-diolate (spermine NONOate or "SPER/NO") and sodium (Z)-1-(N,N-diethylamino) diazenium-1,2-diolate (diethylamine NONOate or "DEA/NO") and derivatives thereof. NONOates are also described in U.S. Pat. Nos. 6,232,336, 5,910,316 and 5,650,447, the disclosures of which are incorporated herein by reference in their entirety. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligo-nucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, Org. Prep. Proc. Int., 15(3): 165–198 (1983), the disclosures of each of which are incorporated by reference herein in their entirety.

Another embodiment of the invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) HS(C(R$_e$)(R$_f$))$_m$SNO;

(ii) ONS(C(R$_e$)(R$_f$))$_m$R$_e$; and (iii) H$_2$N—CH(CO$_2$H)—(CH$_2$)$_m$—C(O)NH—CH(CH$_2$SNO)—C(O)NH—CH$_2$—CO$_2$H;

wherein m is an integer from 2 to 20; R$_e$ and R$_f$ are each independently a hydrogen, an alkyl, a cycloalkoxy, a halogen, a hydroxy, an hydroxyalkyl, an alkoxyalkyl, an arylheterocyclic ring. a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an alkoxy, an aryl, an arylalkyl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, an arylsulfonyloxy, a carbamoyl, a urea, a nitro, —T—Q—, or (C(R$_e$)(R$_f$))$_k$—T—Q, or R$_e$ and R$_f$ taken together are an oxo, a methanthial, a heterocyclic ring, a cycloalkyl group or a bridged cycloalkyl group; Q is —NO or —NO$_2$; and T is independently a covalent bond, a carbonyl, an oxygen, —S(O)$_o$— or —N(R$_a$)R$_i$—, wherein o is an integer from 0 to 2, R$_a$ is a lone pair of electrons, a hydrogen or an alkyl group; R$_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyloxy, an arylsulfinyl, an arylsulfonyloxy, an arylsulfonyl, a sulfonamido, a carboxamido, a carboxylic ester, an aminoalkyl, an aminoaryl, —CH$_2$—C(T—Q)(R$_e$)(R$_f$), or —(N$_2$O$_2$—)$^-$·M$^+$, wherein M$^+$ is an organic or inorganic cation; with the proviso that when R$_i$ is —CH$_2$—C(T—Q)(R$_e$)(R$_f$) or —(N$_2$O$_2$—)·M$^+$; then "—T—Q" can be a hydrogen, an alkyl group, an alkoxyalkyl group, an aminoalkyl group, a hydroxy group or an aryl group.

In cases where $R_e$ and $R_f$ are a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetraflurorborate in an inert solvent.

Another group of NO adducts for use in the invention, where the NO adduct is a compound that donates, transfers or releases nitric oxide, include compounds comprising at least one ON—O—, ON—N—or ON—C—group. The compounds that include at least one ON—O—, ON—N—or ON—C—group are preferably ON—O—, ON—N—or ON—C—polypeptides (the term "polypeptide" includes proteins and polyamino acids that do not possess an ascertained biological function, and derivatives thereof); ON—O—, ON—N—or ON—C—amino acids (including natural and synthetic amino acids and their stereoisomers and racemic mixtures); ON—O—, ON—N—or ON—C—sugars; ON—O—, ON—N—or ON—C—modified or unmodified oligonucleotides (comprising at least 5 nucleotides, preferably 5–200 nucleotides); ON—O—, ON—N—or ON—C—straight or branched, saturated or unsaturated, aliphatic or aromatic, substituted or unsubstituted hydrocarbons; and ON—O—, ON—N—or ON—C—heterocyclic compounds.

Another group of NO adducts for use in the invention include nitrates that donate, transfer or release nitric oxide, such as compounds comprising at least one $O_2N$—O—, $O_2N$—N—, $O_2N$—S—or $O_2N$—C—group. Preferred among these compounds are $O_2N$—O, $O_2N$—N—, $O_2N$—S—or $O_2N$—C—polypeptides (the term "polypeptide" includes proteins and also polyamino acids that do not possess an ascertained biological function, and derivatives thereof); $O_2N$—O—, $O_2N$—N—, $O_2N$—S—or $O_2N$—C—amino acids (including natural and synthetic amino acids and their stereoisomers and racemic mixtures); $O_2N$—O—, $O_2N$—N—, $O_2N$—S—or $O_2N$—C—sugars; $O_2N$—O—, $O_2N$—N—, $O_2N$—S—or $O_2N$—C—modified and unmodified oligonucleotides (comprising at least 5 nucleotides, preferably 5–200 nucleotides); $O_2N$—O—, $O_2N$—N—, $O_2N$—S—or $O_2N$—C—straight or branched, saturated or unsaturated, aliphatic or aromatic, substituted or unsubstituted hydrocarbons; and $O_2N$—O—, $O_2N$—N—, $O_2N$—S—or $O_2N$—C—heterocyclic compounds. Preferred examples of compounds comprising at least one $O_2N$—O—, $O_2N$—N—, $O_2N$—S—or $O_2N$—C—group include isosorbide dinitrate, isosorbide mononitrate, clonitrate, erythrityl tetranitrate, mannitol hexanitrate, nitroglycerin, pentaerythritoltetranitrate, pentrinitrol, propatylnitrate and organic nitrates with a sulfhydryl-containing amino acid such as, for example SPM 3672, SPM 5185, SPM 5186 and those disclosed in U.S. Pat. Nos. 5,284,872, 5,428,061, 5,661,129, 5,807,847 and 5,883,122 and in U.S. Provisional Application No. 60/311,175 and in WO 97/46521 and WO 00/54756, the disclosures of each of which are incorporated by reference herein in their entirety.

Another group of NO adducts are N-oxo-N-nitrosoamines that donate, transfer or release nitric oxide and are represented by the formula: $R^1R^2N$—$N(O$—$M^+)$—NO, where $R^1$ and $R^2$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where $M^+$ is an organic or inorganic cation, such as, for example, an alkyl substituted ammonium cation or a Group I metal cation.

The invention is also directed to compounds that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/ or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid) and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, Nature, 327:524–526 (1987); Ignarro et al, Proc. Natl. Acad. Sci. USA, 84:9265–9269 (1987)).

The invention is also based on the discovery that compounds and compositions of the invention may be used in conjunction with other therapeutic agents for co-therapies, partially or completely, in place of other conventional antinflammatory compounds, such as, for example, together with steroids, NSAIDs, 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG-CoA inhibitors, $H_2$ receptor antagonists, antineoplastic agents, antiplatelet agents, thrombin inhibitors, thromboxane inhibitors, decongestants, diuretics, sedating or non-sedating anti-histamines, inducible nitric oxide synthase inhibitors, opiods, analgesics, Helicobacter pylori inhibitors, proton pump inhibitors, isoprostane inhibitors, and mixtures thereof.

Leukotriene $A_4$ ($LTA_4$) hydrolase inhibitors refer to compounds that selectively inhibit leukotriene $A_4$ hydrolase with an $IC_{50}$ of less than about 10 $\mu M$, and preferably with an $IC_{50}$ of less than about 1 $\mu M$. Suitable $LTA_4$ hydrolase inhibitors include, but are not limited to, RP-64966, (S,S)-3-amino-4-(4-benzyloxyphenyl)-2-hydroxybutyric acid benzyl ester, N-(2(R)-(cyclohexylmethyl)-3-(hydroxycarbamoyl)propionyl)-L-alanine, 7-(4-(4-ureidobenzyl)phenyl) heptanoic acid and 3 (3-(1E,3E-tetradecadienyl)-2-oxiranyl)benzoic acid lithium salt, and mixtures thereof.

Suitable $LTB_4$ receptor antagonists include, but are not limited to, ebselen, linazolast, ontazolast; WAY 121006; Bay-x-1005; BI-RM-270; CGS-25019C; ETH-615; MAFP; TMK-688; T-0757; LY 213024, LY 210073, LY 223982, LY 233469, LY 255283, LY 264086, LY 292728 and LY 293111; ONO-LB457, ONO-4057, and ONO-LB-448, S-2474, calcitrol; PF 10042; Pfizer 105696; RP 66153; SC-53228, SC-41930, SC-50605, SC-51146 and SC-53228; SB-201146 and SB-209247; SKF-104493; SM 15178; TMK-688; BPC 15, and mixtures thereof. The preferred $LTB_4$ receptor antagonists are calcitrol, ebselen, Bay-x-1005, CGS-25019C, ETH-615, LY-293111, ONO-4057 and TMK-688, and mixtures thereof.

Suitable 5-LO inhibitors include, but are not limited to, A-76745, 78773 and ABT761; Bay-x-1005; CMI-392; E-3040; EF-40; F-1322; ML-3000; PF-5901; R-840;

rilopirox, flobufen, linasolast, lonapolene, masoprocol, ontasolast, tenidap, zileuton, pranlukast, tepoxalin, rilopirox, flezelastine hydrochloride, enazadrem phosphate, and bunaprolast, and mixtures thereof. Suitable 5-LO inhibitors are also described more fully in WO 97/29776, the disclosure of which is incorporated herein by reference in its entirety.

Suitable 5-HT agonists, include, but are not limited to, rizatriptan, sumatriptan, naratriptan, zolmitroptan, eleptriptan, almotriptan, ergot alkaloids. ALX 1323, Merck L 741604 SB 220453 and LAS 31416. Suitable 5-HT agonists are described more fully in WO 0025779, and in WO 00/48583. 5-HT agonists refers to a compound that is an agonist to any 5-HT receptor, including but not limited to, 5-$HT_1$ agonists, 5-$HT_{1B}$ agonists and 5-$HT_{1D}$ agonists, and the like.

Suitable steroids, include, but are not limited to, budesonide, dexamethasone, corticosterone, prednisolone, and the like. Suitable steroids are described more fully in the literature, such as in the Merck Index on CD-ROM, Twelfth Edition, Version 12:1, 1996.

Suitable HMG CoA inhibitors, include, but are not limited to, reductase and synthase inhibitors, such as, for example, squalene synthetase inhibitors, benzodiazepine squalene synthase inhibitors, squalene epoxidase inhibitors, acyl-coenzyme A, bile acid sequestrants, cholesterol absorption inhibitors, and the like. Suitable HMG CoA inhibitors include simvastatin, pravastatin, lovastatin, and the like, and are described more fully in U.S. Pat. No. 6,245,797 and WO 99/20110, the disclosures of which are incorporated herein by reference in their entirety.

Suitable NSAIDs, include, but are not limited to, acetaminophen, aspirin, diclofenac, ibuprofen, ketoprofen, naproxen and the like. Suitable NSAIDs are described more fully in the literature, such as in Goodman and Gilman, The Pharmacological Basis of Therapeutics (9th Edition), McGraw-Hill, 1995, Pgs. 617–657; the Merck Index on CD-ROM, Twelfth Edition, Version 12:1, 1996; and in U.S. Pat. Nos. 6,057,347 and 6,297,260 assigned to NitroMed Inc., the disclosures of which are incorporated herein by reference in their entirety.

Suitable $H_2$ receptor anatgonists, include, but are not limited to, cimetidine, roxatidine, rantidine and the like. Suitable $H_2$ receptor antagonists are described more fully in the literature, such as in Goodman and Gilman, The Pharmacological Basis of Therapeutics (9th Edition), McGraw-Hill, 1995, Pgs. 901–915; the Merck Index on CD-ROM, Twelfth Edition, Version 12:1, 1996; and in WO 00/28988 assigned to NitroMed Inc., the disclosures of which are incorporated herein by reference in their entirety.

Suitable antineoplastic agents, include but are not limited to, 5-FU-fibrinogen, acanthifolic acid, aminothiadiazole, altretamine, anaxirone, aclarubicin and the like. Suitable antineoplastic agents are also described in U.S. Pat. No. 6,025,353 and WO 00/38730, the disclosures of which are incorporated herein by reference in their entirety.

Suitable antiplatelet agents, include but are not limited to, aspirin, ticlopidine, dipyridamole, clopidogrel, glycoprotein IIIb/IIIa receptor antagonists, and the like. Suitable antineoplastic agents are also described in WO 99/45913, the disclosure of which is incorporated herein by reference in its entirety.

Suitable antiplatelet agents, include but are not limited to, aspirin, ticlopidine, dipyridamole, clopidogrel, glycoprotein IIb/IIIa receptor antagonists, and the like. Suitable antiplatelet agents are also described in WO 99/45913, the disclosure of which is incorporated herein by reference in its entirety.

Suitable thrombin inhibitors, include but are not limited to, N'—((1-(aminoiminomethyl)-4-piperidinyl)methyl)-N-(3,3-diphenylpropinyl)-L-proline amide),3-(2-phenylethylamino)-6-methyl-1-(2-amino-6-methyl-5-methylene-carboxamidomethylpyridinyl)-2-pyrazinone, 3-(2-phenethylamino)-6-methyl-1-(2-amino-6-methyl-5-methylenecarboxamidomethylpyridinyl)-2-pyridinone, and the like. Suitable thrombin inhibitors are also described in WO 00/18352, the disclosure of which is incorporated herein by reference in its entirety.

Suitable thromboxane inhibitors, include but are not limited to thromboxane synthase inhibitors, thromboxane receptor antagonists, and the like. Suitable thromboxane inhibitors, are also described in WO 01/87343, the disclosure of which is incorporated herein by reference in its entirety.

Suitable decongestants include, but are not limited to, phenylephrine, phenylpropanolamine, pseudophedrine, oxymetazoline, ephinephrine, naphazoline, xylometazoline, propylhexedrine, levo-desoxyephedrine, and the like.

Suitable antitussives include, but are not limited to, codeine, hydrocodone, caramiphen, carbetapentane, dextramethorphan, and the like.

Suitable proton pump inhibitors, include, but are not limited to, omeprazole, esomeprazole, lansoprazole, rabeprazole, pantoprazole, and the like. Suitable proton pump inhibitors are described more fully in the literature, such as in Goodman and Gilman, The Pharmacological Basis of Therapeutics (9th Edition), McGraw-Hill, 1995, Pgs. 901–915; the Merck Index on CD-ROM, Twelfth Edition, Version 12:1, 1996; and in WO 00/50037 assigned to NitroMed Inc., the disclosures of which are incorporated herein by reference in their entirety.

The compounds and compositions of the invention, may also be used in combination therapies with opioids and other analgesics, including, but not limited to, narcotic analgesics, Mu receptor antagonists, Kappa receptor antagonists, non-narcotic (i.e. non-addictive) analgesics, monoamine uptake inhibitors, adenosine regulating agents, cannabinoid derivatives, neurokinin 1 receptor antagonists, Substance P antagonists, neurokinin-1 receptor antagonists, sodium channel blockers, N-methyl-D-aspartate receptor antagonists, and mixtures thereof. Preferred combination therapies would be with morphine, meperidine, codeine, pentazocine, buprenorphine, butorphanol, dezocine, meptazinol, hydrocodone, oxycodone, methadone, Tramadol ((+) enantiomer), DuP 747, Dynorphine A, Enadoline, RP-60180, HN-11608, E-2078, ICI-204448, acetominophen (paracetamol), propoxyphene, nalbuphine, E-4018, filenadol, mirtentanil, amitriptyline, DuP631, Tramadol ((−) enantiomer), GP-531, acadesine, AKI-1, AKI-2, GP-1683, GP-3269, 4030W92, tramadol racemate, Dynorphine A, E-2078, AXC3742, SNX-111, ADL2-1294, ICI-204448, CT-3, CP-99,994, CP-99,994, and mixtures thereof.

The compounds and compositions of the invention can also be used in combination with inducible nitric oxide synthase (iNOS) inhibitors. Suitable iNOS inhibitors are disclosed in U.S. Pat. Nos. 5,132,453 and 5,273,875, and in WO 97/38977 and WO 99/18960, the disclosures of each of which are incorporated by reference herein in their entirety.

The invention is also based on the discovery that the administration of a therapeutically effective amount of the compounds and compositions described herein is effective for treating inflammation, pain (both chronic and acute), and fever, such as, for example, analgesic in the treatment of pain, including, but not limited to headaches, migraines, postoperative pain, dental pain, muscular pain, and pain resulting from cancer; as an antipyretic for the treatment of fever, including but not limited to, rheumatic fever, symptoms associated with influenza or other viral infections, common cold, low back and neck pain, dysmenorrhea, headache, toothache, sprains, strains, myositis, neuralgia, synovitis; arthritis, including but not limited to rheumatoid arthritis, degenerative joint disease (osteoarthritis), spondyloarthropathies, gouty arthritis, systemic lupus erythematosus and juvenile arthritis. For example, the patient can be administered a therapeutically effective amount of at least one COX-2 selective inhibitor of the invention. In another embodiment, the patient can be administered a therapeutically effective amount of at least one nitrosated and/or nitrosylated COX-2 selective inhibitor. In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and, at least one therapeutic agent, including but not limited to, steroids, nonsterodal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Another embodiment of the invention provides methods for decreasing and/or preventing gastrointestinal disorders and improving the gastrointestinal properties of the COX-2 selective inhibitor by administering to the patient in need thereof a therapeutically effective amount of the compounds and/or compositions described herein. Such gastrointestinal disorders refer to any disease or disorder of the upper gastrointestinal tract (e.g., esophagus, the stomach, the duodenum, jejunum) including, for example, inflammatory bowel disease, Crohn's disease, gastritis, irritable bowel syndrome, ulcerative colitis, peptic ulcers, stress ulcers, gastric hyperacidity, dyspepsia, gastroparesis, Zollinger-Ellison syndrome, gastroesophageal reflux disease, bacterial infections (including, for example, a *Helicobacter Pylori* associated disease), short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns. For example, the patient can be administered a therapeutically effective amount of at least one nitrosated and/or nitrosylated COX-2 selective inhibitor of the invention. In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and at least one therapeutic agent, including but not limited to, steroids, nonsterodal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Yet another embodiment of the invention provides methods for facilitating wound healing (such as, for example, ulcer healing) by administering to the patient in need thereof a therapeutically effective amount of the compounds and/or compositions described herein. Wound refers to, and includes, any lesion that is characterized by loss of tissue, and, includes, but are not limited to, ulcers, cuts, bums, and the like. Ulcers refers to lesions of the upper gastrointestinal tract lining that are characterized by loss of tissue, and, include, but are not limited to, gastric ulcers, duodenal ulcers, gastritis, and the like. For example, the patient can be administered a therapeutically effective amount of at least one nitrosated and/or nitrosylated COX-2 selective inhibitor of the invention. In another embodiment, the patient can be administered a therapeutically effective amount of at least one COX-2 selective inhibitor, that is optionally nitrosated and/or nitrosylated, and at least one nitric oxide donor. In yet another embodiment, the patient can be administered a therapeutically effective amount of at least one COX-2 selective inhibitor, that is optionally nitrosated and/or nitrosylated, and at least one therapeutic agent, and, optionally, at least one nitric oxide donor. The compounds can be administered separately or in the form of a composition.

Another embodiment of the invention provides methods to decrease or reverse renal and other toxicities (such as, for example, kidney toxicity) by administering to a patient in need thereof a therapeutically effective amount of the compounds and/or compositions described herein. For example, the patient can be administered a therapeutically effective amount of at least one nitrosated and/or nitrosylated COX-2 selective inhibitor of the invention. In another embodiment, the patient can be administered a therapeutically effective amount of at least one COX-2 selective inhibitor, that is optionally nitrosated and/or nitrosylated, and at least one nitric oxide donor. In yet another embodiment, the patient can be administered a therapeutically effective amount of at least one COX-2 selective inhibitor, that is optionally nitrosated and/or nitrosylated, and at least one therapeutic agent, and, optionally, at least one nitric oxide donor. The compounds can be administered separately or in the form of a composition.

Another embodiment of the invention provides methods to treat or prevent disorders resulting from elevated levels of COX-2 by administering to a patient in need thereof a therapeutically effective amount of the compounds and/or compositions described herein. For example, the patient can be administered a therapeutically effective amount of at least one COX-2 selective inhibitor, that is optionally nitrosated and/or nitrosylated, of the invention. In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and at least one therapeutic agent, including but not limited to, steroids, a nonsterodal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Disorders resulting from elevated levels of COX-2 (e.g., COX-2 mediated disorders) include, but are not limited to, for example, angiogenisis, arthritis, asthma, bronchitis, menstrual cramps, premature labor, tendinitis, bursitis; skin-related conditions, such as, for example, psoriasis, eczema, surface wounds, bums and dermatitis; post-operative inflammation including from ophthalmic surgery, such as, for example, cataract surgery and refractive surgery, and the like; treatment of neoplasia, such as, for example, brain cancer, bone cancer, epithelial cell-derived neoplasia (epithelial carcinoma), such as, for example, basal cell carcinoma, adenocarcinoma, gastrointestinal cancer, such as, for example, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that effect epithelial cells throughout the body, benign and cancerous tumors, growths, polyps, adenomatous polyps, including, but not limited to, familial adenomatous polyposis, fibrusis resulting from radiation therapy, and the like; treatment of inflammatory processes in diseases, such as, for example, vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like; treatment of ophthalmic diseases and disorders, such as, for example, retinitis, retinopathies, uveitis, ocular photophobia, acute injury to the eye tissue, glaucoma, inflammation of the eye and elevation of intraocular pressure and the like; treatment of pulmonary inflammation, such as, for example, those associated with viral infections and cystic fibrosis, and the like; treatment of central nervous system disorders, such as, for example, cortical dementias including Alzheimer's disease, vascular dementia, multi-infarct dementia, pre-senile dementia, alcoholic dementia, senile dementia, and central nervous system damage resulting from stroke, ischemia and trauma, and the like; treatment of allergic rhinitis, respiratory distress syndrome, endotoxin shock syndrome, atherosclerosis; treatment of inflammations and/or microbial infections including, for example, inflammations and/or infections of the eyes, ears, nose, throat, and/or skin; treatment and/or prevention of cardiovascular disorders, such as, for example, coronary artery disease, aneurysm, arteriosclerosis, atherosclerosis, including, but not limited to, cardiac transplant atherosclerosis, myocardial infaraction, hypertension, ischemia, embolism, stroke, thrombosis, venous thrombosis, thromboembolism, thrombotic occlusion and reclusion, restenosis, angina, unstable angina, shock, heart failure, coronary plaque inflammation, bacterial-induced inflammation, such as, for example, Chlamydia-induced inflammation, viral induced inflammation, inflammation associated with surgical procedures, such as, for example, vascular grafting, coronary artery bypass surgery, revascularization procedures, such as, for example, angioplasty, stent placement, endarterectomy, vascular procedures involving arteries, veins, capillaries, and the like; treatment and/or prevention of urinary and/or urological disorders, such as, for example, incontinence and the like; treatment and/or prevention of endothelial dysfunctions, such as, for example, diseases accompanying these dysfunctions, endothelial damage from hypercholesterolemia, endothelial damage from hypoxia, endothelial damage from mechanical and chemical noxae, especially during and after drug, and mechanical reopening of stenosed vessels, for example, following percutaneous transluminal angiography (PTA) and percuntaneous transluminal coronary angiography (PTCA), endothelial damage in postinfarction phase, endothelium-mediated reocculusion following bypass surgery, blood supply distrubances in peripheral arteries, as well as, cardiovascular diseases, and the like; disorders treated by the preservation of organs and tissues, such as, for example, for organ transplants, and the like; disorders treated by the inhibition and/or prevention of activation, adhesion and infiltration of neutrophils at the site of inflammation; and disorders treated by the inhibition and/or prevention of platelet aggregation. The compounds and compositions of the invention can also be used as a pre-anesthetic medication in emergency operations to reduce the danger of aspiration of acidic gastric contents.

Another embodiment of the invention provides methods for improving the cardiovascular profile of COX-2 selective inhibitors by administering to a patient in need thereof a therapeutically effective amount of the compounds and/or compositions described herein. For example, the patient can be administered a therapeutically effective amount of at least one nitrosated and/or nitrosylated COX-2 selective inhibitor of the invention. In another embodiment, the patient can be administered a therapeutically effective amount of at least one COX-2 selective inhibitor, that is optionally nitrosated and/or nitrosylated, and at least one nitric oxide donor. In yet another embodiment, the patient can be administered a therapeutically effective amount of at least one COX-2 selective inhibitor, that is optionally nitrosated and/or nitrosylated, at least one of 3-hydroxy-3-methylglutaryl coenzyme A (HMG-CoA) inhibitors, antiplatelet agents, thrombin inhibitors, thromboxane inhibitors, and, optionally, at least one nitric oxide donor. The compounds can be administered separately or in the form of a composition.

When administered in vivo, the compounds and compositions of the invention can be administered in combination with pharmaceutically acceptable carriers and in dosages described herein. When the compounds and compositions of the invention are administered as a mixture of at least one COX-2 selective inhibitor and/or at least one nitrosated and/or nitrosylated COX-2 selective inhibitor and/or at least one nitric oxide donor and/or therapeutic agent, they can also be used in combination with one or more additional compounds which are known to be effective against the specific disease state targeted for treatment. The nitric oxide donors, therapeutic agents and/or other additional compounds can be administered simultaneously with, subsequently to, or prior to administration of the COX-2 selective inhibitor and/or nitrosated and/or nitrosylated COX-2 selective inhibitor.

The compounds and compositions of the invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional non-toxic pharmaceutically acceptable carriers, adjuvants, and vehicles, as desired. Parenteral includes subcutaneous injections, intravenous, intramuscular, intrastemal injection, or infusion techniques.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention, such as for treating pediatric fever and the like, can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules and the like. The required dosage can be administered as a single unit or in a sustained release form.

The bioavailabilty of the compositions can be enhanced by micronization of the formulations using conventional techniques such as grinding, milling, spray drying and the like in the presence of suitable excipients or agents such as phospholipids or surfactants.

The preferred methods of administration of the COX-2 selective inhibitors and compositions for the treatment of gastrointestinal disorders are orally, bucally or by inhalation. The preferred methods of administration for the treatment of inflammation and microbial infections are orally, bucally, topically, transdermally or by inhalation.

The compounds and compositions of the invention can be formulated as pharmaceutically acceptable salt forms. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesuifonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The amount of a given COX-2 selective inhibitor of the invention that will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The amount of nitric oxide donor in a pharmaceutical composition can be in amounts of about 0.1 to about 10 times the molar equivalent of the COX-2 selective inhibitor. The usual daily doses of the COX-2 selective inhibitors are about 0.001 mg to about 140 mg/kg of body weight per day, preferably 0.005 mg to 30 mg/kg per day, or alternatively about 0.5 mg to about 7 g per patient per day. For example, inflammations may be effectively treated by the administration of from about 0.01 mg to 50 mg of the compound per kilogram of body weight per day, or alternatively about 0.5 mg to about 3.5 g per patient per day. The compounds may be administered on a regimen of up to 6 times per day, preferably 1 to 4 times per day, and most preferably once per day. Effective doses may be extrapolated from dose-response curves derived from in vitro or animal model test systems and are in the same ranges or less than as described for the commercially available compounds in the Physician's Desk Reference, supra.

The invention also provides pharmaceutical kits comprising one or more containers filled with one or more of the ingredients of the pharmaceutical compounds and/or compositions of the invention, including, at least, one or more of the novel COX-2 selective inhibitors, that is optionally nitrosated and/or nitrosylated, and one or more of the NO donors described herein. Associated with such kits can be additional therapeutic agents or compositions (e.g., steroids, NSAIDs, 5-lipoxygenase (5-LO) inhibitors, leukotriene $B_4$ ($LTB_4$) receptor antagonists and leukotriene $A_4$ ($LTA_4$) hydrolase inhibitors, 5-HT agonists, HMG-CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like), devices for administering the compositions, and notices in the form prescribed by a governmental agency regulating the manufacture, use or sale of pharmaceuticals or biological products which reflects approval by the agency of manufacture, use or sale for humans.

EXAMPLES

The following non-limiting examples further describe and enable one of ordinary skill in the art to make and use the invention. In each of the examples, flash chromatography was performed on 40 micron silica gel (Baker). All the reagents used are readily available from commercial sources.

Example 1

1-(6-(Cyclohexylmethyl)(2-H-benzo(3,4-d)1,3-dioxolen-5-yl))-4-(methylsulfonyl)benzene 1a. 6-Bromo-2H-benzo(d)1,3-dioxolene-5-carbaldehyde The title compound was synthesized as described in the literature (Khanapure, S. P. and Biehl, E. R. *J. Org. Chem.* 1990, 55, 1471). Treatment of piperonal (40 g) with bromine (40 mL) in acetic acid (500 mL) and carbon disulfide (50 mL) containing a catalytic amount of iodine at room temperature, overnight, gave the title compound (46 g, 70% yield), mp 128–130° C. $^1$H NMR (300 MHz, CDCl$_3$) δ10.17 (s, 1H, 7.33 (s, 1H), 7.03 (s, 1H), 6.06 (s, 2H), $^{13}$C NMR (75 MHz, CDCl$_3$) δ190.3, 153.3, 148.1, 128.0, 121.5, 113.2, 108.1, 102.7; mass spectrum (API-TIS) m/z 229 (Br 79) and 231 (Br 81) (M+H) LRMS (APIMS) m/z 229 (M+H)$^+$ and 231 ((M+H)+2)$^+$.

1b. 6-(4-Methylthiophenyl)-2H-benzo(d)1,3-dioxolene-5-carbaldehyde

The product of Example 1a (1.15 g, 5 mmol) and 4-(methylthio)benzeneboronic acid (840 mg, 5 mmol) were dissolved in toluene (75 mL) and sodium carbonate (2M, 5 mL, 10 mmol) was added. To this reaction mixture was added ethanol (2 mL) followed by tetrakis (triphenylphosphine) palladium (680 mg, 0.5 mmol). The reaction mixture was refluxed overnight under a nitrogen atmosphere. The reaction mixture was then diluted with water (25 mL) and extracted with EtOAc (2×150 mL). The combined organic extracts were washed with water (4×50 mL), brine (1×25 mL), dried over sodium sulfate, and filtered. The filtrate was evaporated under reduced pressure and the residue was chromatographed on silica gel and eluted with Hex:EtOAc (19:1). This gave the title compound as a white solid (1.2 g, 88% yield). $^1$H NMR (300 MHz, CDCl$_3$) δ9.74 (s, 1H), 7.41 (s, 1H), 7.29 (m, 4H), 6.80 (s, 1H), 6.07 (s, 2H), 2.52 (s, 3H); $^{13}$C NMR (75 MHz, CDCl$_3$) δ190.4, 152.1, 147.7, 142.9, 139.1, 134.0, 130.4, 128.7, 126.0, 110.0, 106.2; mass spectrum (API-TIS) m/z 273 (M+H).

1c. 1-(6-(Cyclohexylidenemethyl)(2-H-benzo(3,4-d)1,3-dioxolen-5-yl))-4-methylthiobenzene A suspension of cyclohexyl(triphenyl)phosphonium bromide (1.7 g, 4 mmol) in anhydrous THF (25 mL) was stirred at –78° C. n-BuLi (1.4 mL of 2.5 M in hexane, 3.5 mmol) was added drop-wise to the stirred suspension under nitrogen atmosphere. The reaction mixture was stirred at –78° C. to –60° C. for over a period of 1 hour. The suspension of ylide was then cooled to –78° C. and the product of Example 1b (272 mg, 1 mmol) in THF (5 mL) was added drop-wise to the ylide solution. The reaction mixture was stirred for 1.5 hours at –78° C., then slowly allowed to warm to room temperature and stirred at room temperature overnight. The reaction mixture was then quenched with saturated aqueous ammonium chloride and extracted with EtOAc (2×50 mL). The combined organic extracts were washed with water (1×50 mL), brine (1×50 mL) dried over sodium sulfate, and filtered. The filtrate was evaporated and the residue was chromatographed on silica gel and eluted with Hex:EtOAc (9:1). This gave the title compound as a white powder, (250 mg, 67% yield), mp 83–84° C. $^1$H NMR (300 MHz, CDCl$_3$) δ7.31 (m, 4H), 6.79 (s, 1H), 6.72 (s, 1H), 5.92 (s, 2H), 5.88 (s, 1H), 2.51 (s, 3H), 2.23 (t, J=5.6 Hz, 2H), 2.11 (m, 2H), 1.45–1.55 (m, 6H).

1d. 1-(6-(Cyclohexylidenemethyl)(2-H-benzo(3,4-d) 1,3-dioxolen-5-yl))-4-(methylsulfonyl)benzene The product of Example 1c (230 mg, 0.68 mmol) was dissolved in methanol (10 mL) with stirring at room temperature. A solution of OXONE® (835 mg, 1.36 mmol) in water (5 mL) was added. The reaction mixture was stirred at room temperature for 2 hours, and then diluted with water (25 mL), neutralized with ammonium hydroxide and extracted with EtOAc (2×50 mL). The combined organic extracts were washed with water (2×50 mL), brine (1×25 mL), dried over sodium sulfate, and filtered. The filtrate was evaporated under reduced pressure and the residue was chromatographed on silica gel, eluted with Hex:EtOAc (1:1) to give the title compound as a crystalline solid, (140 mg, 56% yield), mp 147–151° C. $^1$H NMR (300 MHz, CDCl$_3$) δ7.89 (d, J=8.3 Hz, 2H), 7.84 (d, J=8.3 Hz, 2H), 6.77 (s, 1H), 6.72 (s, 1H), 5.98 (s, 2H), 3.07 (s, 3H), 2.14 (t, J=5.6 Hz, 2H), 2.08 (m, 2H), 1.51–1.30 (m, 6H); $^{13}$C NMR (75 MHz, CDCl$_3$) δ47.2, 147.1, 146.4, 138.3, 135.5, 130.6, 130.5, 126.8, 120.9, 110.5, 109.4, 101.2, 44.5, 36.9, 29.5, 28.2. 27.3, 26.4; mass spectrum (API-TIS) m/z 371 (M+H).

1e. 1-(6-(Cyclohexylmethyl)(2-H-benzo(3,4-d)1,3-dioxolen-5-yl))-4-(methylsulfonyl) benzene The product of Example 1d (110 mg, 0.297 mmol) was dissolved in a mixture of EtOAc (5 mL) and EtOH (25 mL). The catalyst, palladium on carbon (250 mg, 10% yield) was added under a stream of nitrogen. The hydrogenation was performed at 20 psi of hydrogen for 3 hours. The solution was filtered to remove the catalyst and the filtrate was evaporated under reduced pressure to give the crude product that was triturated with Hex:EtOAc (5:1) to give the title compound (60 mg, 54% yield), mp 112–116° C. $^1$H NMR (300 MHz, CDCl$_3$) δ7.94 J=8.2 Hz, 2H), 7.43 (d, J=8.2 Hz, 2H), 6.75 (s, 1H), 6.61 (s, 1H), 5.97 (s, 2H), 3.10 (s, 3H), 2.34 (d, J=5.1 Hz, 2H), 1.6–0.80 (m, 11H); $^{13}$C NMR (75 MHz, CDCl$_3$) δ148.1, 147.4, 145.5, 138.7 133.3, 132.5, 130.7, 127.1, 109.8, 109.5, 101.1, 44.5, 40.2, 39.8, 32.9 (233 C), 26.3, 26.2 (233 C); mass spectrum (API-TIS) m/z 390 (M+NH$_4$).

Example 2

Cyclohexyl(6-(4-(methylsulfonyl)phenyl)(2H-benzo (d)1,3-dioxolan-5-yl) ketone

2a. Cyclohexyl(6-(4-methylthiophenyl)(2H-benzo(d)1,3-dioxolan-5-yl))methan-1-ol

The product of Example 1b (272 mg, 1 mmol) was dissolved in anhydrous THF (10 mL). The solution was cooled to 0° C. and cyclohexyl magnesium bromide (2 M in THF, 2 mL, 2 mmol) was added drop-wise under nitrogen atmosphere. The reaction mixture was stirred at 0° C. for 30 minutes and then at room temperature for 2 hours. The reaction was quenched with saturated aqueous ammonium chloride, acidified with 1 N HCl and then extracted with ethyl acetate (2×50 mL). The combined organic extracts were washed with water (1×25 mL), brine (1×25 mL), dried over sodium sulfate, filtered and the filtrate was evaporated under reduced pressure to give the crude product. Purification by silica gel column chromatography using 20% ethyl acetate in hexane gave the title compound as a white solid (331 mg, 93% yield), mp 110–1120° C. $^1$H NMR (CDCl$_3$) δ 7.26 (d, J=8.4 Hz, 2H), 7.18 (d, J=8.4 Hz, 2H), 7.01 (s, 1H), 6.64 (s, 1H), 5.97 (dd, J=4.1 and 1.3 Hz, 2H), 2.52 (s, 3H), 2.0 (m, 1H, OH), 1.80–1.50 (m, 4H), 1.20–0.5 (m, 6H); $^{13}$C NMR (CDCl$_3$) δ147.3, 146.4, 137.9, 137.0, 135.0, 134.8, 130.0 (2×C), 126.2 (2×C), 109.7, 106.2, 101.1, 74.9, 44.9, 29.3, 29.2, 26.2, 26.0, 28.9, 15.7; LRMS (APIMS) m/z 730 (2 M+NH$_4$)$^+$, 339 (M-OH)$^+$.

2b. 1-(6-(Cyclohexylhydroxymethyl)(2H-benzo(3,4-d)1,3-dioxolan-5-yl))-4-(methylsulfonyl)benzene The product of Example 2a (160 mg, 0.449 mmol) was dissolved in MeOH (10 mL). To this solution, OXONE® (550 mg, 0.898 mmol) in water (2 mL) was added. The reaction mixture was stirred at room temperature for 2 hours, diluted with water and ammonium hydroxide was added until the solution was basic. The solvent was evaporated under reduced pressure. The resulting product was extracted with ethyl acetate (2×50 mL), washed with brine (1×50 mL), dried over anhydrous sodium sulfate, filtered and the filtrate was evaporated under reduced pressure to give an oil which upon trituration with hexane yielded the title compound (160 mg, 92% yield), mp 140–142° C. $^1$H NMR (CDCl$_3$) δ7.93 (d, J=8.3 Hz, 2H), 7.46 (d, J=8.4 Hz, 2H), 7.03 (s, 1H), 6.60 (s, 1H), 5.98 (s, 2H), 4.21 (d, J=6.8 Hz, 1H), 3.1 (s, 3H), 2.0 (m, 1H), 1.7–0.5 (m, 10H); $^{13}$C NMR (CDCl$_3$) δ148.1, 147.1, 146.7, 139.0, 134.8, 133.4, 130.7 (2×C), 127.3 (2×C), 109.2, 106.6, 101.4, 74.8, 45.0, 44.5, 29.3, 29.1, 26.1, 25.9, 25.8; LRMS (APIMS) m/z 406 (M+NH$_4$)$^+$.

2c. Cyclohexyl 6-(4-(methylsulfonyl)phenyl)(2H-benzo(d)1,3-dioxolan-5-yl) ketone A suspension of the product of the Example 2b (150 mg, 0.386 mmol) and alumina (1 g) in anhydrous CH$_2$Cl$_2$ (50 mL) was stirred at room temperature. While stirring, pyridinium chlorochromate (260 mg, 1.158 mmol) was added and the reaction mixture was stirred at room temperature for 1 hour. The mixture was diluted with CH$_2$Cl$_2$ and the alumina was removed by filtration. The filtrate was washed with water (1×50 mL), saturated aqueous sodium bicarbonate (2×50 mL), brine (1×50 mL), dried over anhydrous sodium sulfate, filtered and the filtrate was evaporated under reduced pressure. Purification by flash column chromatography using ethyl acetate as the eluant gave the title compound as a white solid, (130 mg, 82% yield), mp 172–174° C. $^1$H NMR (CDCl$_3$) δ7.93 (d, J=8.3 Hz, 2H), 7.45 (d, J=8.4 Hz, 2H), 7.03 (s, 1H), 6.8 (s, 1H), 6.05 (s, 2H), 2.25 (m, 1H), 1.7–1.5 (m, 5H), 1.3–0.8 (m, 5H); $^{13}$C NMR (CDCl$_3$) δ149.4, 147.7, 139.3, 134.0, 133.8, 129.6 (2×C), 127.4 (2×C), 110.2, 108.6, 102.0, 49.7, 44.5 (2×C), 29.1 (2×C), 25.6 (2'C); LRMS (APIMS) m/z 404 (M+NH$_4$), 387 (M+H)$^+$.

Example 3

6-(4-(Methylsulfonyl)phenyl)(2H-benzo(d)1,3-dioxolan-5-yl)phenyl ketone 3a. (6-(4-Methylthiophenyl)(2H-benzo(d)1,3-dioxolan-5-yl))phenylmethan-1-ol The product of Example 1b (2.72 g, 10 mmol) was dissolved in anhydrous THF (100 mL). The solution was cooled to 0° C. and phenyl magnesium chloride (2 M in THF) (12 mL, 24 mmol) was added drop-wise under a nitrogen atmosphere. The reaction mixture was stirred at 0° C. for 30 minutes and then at room temperature for 2 hours. The reaction was quenched with saturated aqueous ammonium chloride, acidified with 1 N HCl and the THF layer was separated. The aqueous layer was extracted with ethyl acetate. The combined organic extracts were dried over sodium sulfate, filtered and the filtrate was evaporated under reduced pressure to give the crude product. Purification by silica gel column chromatography using 20% ethyl acetate in hexane as the eluant gave the title compound as a white solid (2.3 g, 66% yield), mp 96–99° C. $^1$H NMR (CDCl$_3$) δ 7.21 (m, 9H), 6.95 (s, 1H), 6.69 (s, 1H), 5.94 (s, 2H), 5.82 (s, 1H), 2.50 (s, 3H), 2.24 (br s, 1H, OH); $^{13}$C NMR (CDCl$_3$) δ147.2, 146.7, 143.9, 137.4, 137.3, 134.9, 134.5, 129.9, 128.2, 127.1, 126.3, 126.2, 109.7, 107.5, 101.1, 72.0, 15.7; LRMS (APIMS) m/z 333 ((M+NH$_4$)—OH)$^+$.

3b. 1-(6-(Hydroxyphenylmethyl)(2H-benzo(3,4-d)1,3-dioxolan-5-yl))-4-(methylsulfonyl)benzene The product of Example 3a (400 mg, 1.17 mmol) was dissolved in CH$_2$Cl$_2$ (20 mL) and saturated aqueous sodium bicarbonate (10 mL) was added. To this mixture, recrystallized (98% purity) m-chloroperbenzoic acid (530 mg, 2.97 mmol) was added and the resulting mixture was stirred at room temperature for 2 hours under nitrogen atmosphere. The organic layer was separated and the aqueous layer was extracted with CH$_2$Cl$_2$ (3×25 mL). The combined organic layers were washed with saturated aqueous sodium bicarbonate (4×25 mL), water (1×25 mL) brine (1×25 mL), dried over anhydrous sodium sulfate, filtered, and the filtrate was evaporated under reduced pressure to give a white foam (450 mg). Purification by silica gel column chromatography using ethyl actate/hexane (1:1) as the eluant gave the title compound as a white solid, (420 mg, 94% yield), mp 144–148° C. $^1$H NMR (CDCl$_3$) δ7.89 (d, J=8.0 Hz, 2H), 7.44 (d, J=8.0 Hz, 2H), 7.23 (m, 3H), 7.12 (m, 2H), 7.0 (s, 1H), 6.65 (s, 1H), 5.97 (s, 2H), 5.69 (s, 1H), 3.06 (s, 3H), 2.44 (br s, 1H, OH); $^{13}$C NMR (CDCl$_3$) δ 148.1, 146.9, 146.5, 143.4, 139.2, 134.9, 133.0, 130.5, 128.3, 127.4, 127.1, 126.3, 109.4, 107.8, 101.4, 72.1, 44.5; LRMS (APIMS) m/z 400 (M+NH$_4$)$^+$.

3c. 4-(Methylsulfonyl)-1-(6-benzyl(2H-benzo(3,4-d)1,3-dioxolan-5-yl))benzene

The product of Example 3b (550 mg, 1.435 mmol) was dissolved in ethanol (200 mL). Under a nitrogen atmosphere palladium on carbon (10% catalyst, 250 mg) was added. Hydrogenation was performed overnight at 40 psi under a hydrogen atmosphere. The solution was filtered to remove the catalyst and the filtrate was evaporated under reduced pressure to give the crude product that was triturated with 20% ethyl acetate in hexane to give the title compound (400 mg, 76% yield), mp 111–114° C. $^1$H NMR (CDCl$_3$) δ7.90 (d, J=8.4 Hz, 2H), 7.40 (d, J=8.3 Hz, 2H), 7.25–7.10 (m, 3H), 6.94 (d, J=7.0 Hz, 2H), 6.71 (s, 1H), 6.70 (s, 1H), 5.99 (s, 2H), 2.75 (s, 3H); $^{13}$C NMR (CDCl$_3$) δ 147.8, 147.3, 146.2, 140.9, 138.9, 133.8, 133.4, 131.7, 130.4, 130.2, 128.52, 128.48, 127.2, 126.1, 110.6, 109.7, 101.3, 44.6, 38.8; LRMS (APIMS) m/z 384 (M+H)$^+$.

3d. 6-(4-(Methylsulfonyl)phenyl)(2H-benzo(d)1,3-dioxolan-5-yl) phenyl ketone

A suspension of Example 3b (115 mg, 0.3 mmol) and alumina (1 g) in anhydrous CH$_2$Cl$_2$ (10 mL) were stirred at room temperature. To this mixture, pyridinium chlorochromate (126 mg, 0.58 mmol) was added and the mixture stirred at room temperature for 15 minutes. The reaction mixture was diluted with CH$_2$Cl$_2$, then the alumina was removed by filtration. The filtrate was washed with water (3×25 mL), saturated aqueous sodium bicarbonate (2×25 mL), brine (1×25 mL), then dried over anhydrous sodium sulfate, filtered and the filtrate evaporated under reduced pressure. Purification by flash column chromatography using 40% ethyl acetate in hexanes as the eluant gave the title compound as a white solid, (110 mg, 96.5% yield), mp 180–184° C. $^1$H NMR (CDCl$_3$) δ 7.72 (d, J=8.0 Hz, 2H), 7.61 (d, J=7.5 Hz, 2H), 7.41 (m, 3H), 7.27 (m, 2H), 7.03 (s, 1H), 6.89 (s, 1H), 6.10 (s, 2H), 2.93 (s, 3H); $^{13}$C NMR (CDCl$_3$) δ 196.8, 149.4, 147.5, 145.9, 139.0, 137.5, 134.9, 132.9, 132.8, 129.9, 129.8, 128.2, 127.2, 110.1, 109.8, 102.1, 44.4; LRMS (APIMS) m/z 381 (M+H)$^+$.

Example 4

2-Fluorophenyl 6-(4-(methylsulfonyl)phenyl)(2H-benzo(d)1,3-dioxolan-5-yl) ketone 4a. (2-Fluorophenyl)(6-(4-methylthiophenyl)(2H-benzo(d)1,3-dioxolan-5-yl))methan-1-ol To a −78° C. cooled solution of 1-bromo-2-fluorobenzene (1.75 g, 10 mmol) in anhydrous THF (60 mL) was added t-BuLi (1.7 M, 12 mL, 20 mmol). The resulting red solution was stirred at −78° C. for 15 minutes and then the product of Example 1b (1.36 g, 5 mmol) in THF (20 mL) was added drop-wise. The reaction mixture was stirred at −78° C. for 30 minutes then slowly allowed to warm to room temperature and stirred at room temperature for 1 hour. The reaction was quenched with saturated aqueous ammoniun chloride solution and then acidified with 1 N HCl. The aqueous layer was extracted with ethyl acetate. The combined organic extracts were dried over sodium sulfate, filtered, and the filtrate was evaporated under reduced pressure to give the crude product that was purified by flash column chromatography using 20% ethyl acetate in hexanes to yield the title compound (1.85 g). Recrystallization from hexane gave the title compound as a white solid, (1.4 g, 76% yield), mp 130–135° C. $^1$H NMR (CDCl$_3$) δ 7.51 (t, J=8.3 Hz, 1H), 7.32 (d, J=8.4 Hz, 1H), 7.30–7.20 (m, 5H), 6.91 (m, 1H), 6.85 (s, 1H), 6.71 (s, 1H), 6.02 (s, 1H), 5.94 (s, 2H), 2.50 (s, 3H), 2.31 (br s, 1H, OH); $^{13}$C NMR (CDCl$_3$) δ161.3, 158.0, 146.8, 137.3, 134.9, 133.4, 130.8, 129.8, 128.8, 127.5, 127.1, 126.2, 123.9, 115.2, 110.0, 107.4, 101.2, 67.00, 15.8; LRMS (APIMS) m/z 351 (M-OH)$^+$, 754 (2 M+NH$_4$)$^+$.

4b. (2-Fluorophenyl)(6-(4-methylthiophenyl)(2H-benzo(d) 1,3-dioxolan-5-yl))methan-1-ol The product of Example 4a (700 mg, 1.9 mmol) was dissolved in MeOH (180 mL). To this solution, OXONE® (2.7 g, 2.9 mmol) dissolved in H$_2$O (40 mL) was added drop-wise. The mixture was stirred at room temperature for 2 hours, diluted with water and ammonium hydroxide was added until the solution was basic. The solvent was evaporated under reduced pressure. The resulting product was extracted with ethyl acetate (2×75 mL), washed with brine (1×50 mL), dried over anhydrous sodium sulfate, filtered and the extracts were evaporated under reduced pressure to give the title compound that was used without further purification, (740 mg, 93% yield), mp 163–169° C. $^1$H NMR (CDCl$_3$) δ 7.85 (d, J=6.4 Hz, 2H), 7.46 (d, J =6.5 Hz, 2H), 7.46 (d, J=6.5 Hz, 2H), 7.4–7.1 (m, 3H), 6.85 (s, 1H), 6.80 (m, 1H), 6.61 (s, 1H), 5.99 (s, 2H), 5.91(d, J=3.8 Hz, 1H), 3.07 (s, 3H), 2.44 (d, J=4.1 Hz, 1H, OH); LRMS (APIMS) m/z 418 (M+NH$_4$)$^+$.

4c. 1-(6-((2-Fluorophenyl)methyl)(2H-benzo(3,4-d)1,3-dioxolan-5-yl))-4-(methylsulfonyl)benzene The product of Example 4b (300 mg, 0.75 mmol) was dissolved in anhydrous CH$_2$Cl$_2$ (10 mL) and under nitrogen atmosphere trifluoroacetic acid (5 mL) was added at 0° C. The reaction mixture was stirred at 0° C. for 15 minutes and to the resulting dark orange solution was then added, in small portions, sodium borohydride (416 mg, 11.25 mmol). The reaction mixture was stirred at 0° C. for 15 minutes and then at room temperature for 15 minutes. The solvent and trifluoroacetic acid were evaporated under reduced pressure and the residue was extracted with dichloromethane. The combined organic extracts were washed with water, brine, dried over sodium sulfate and filtered. The filtrate was evaporated under reduced pressure to give the crude product that was purified by silica gel column chromatography using 20% ethyl acetate in hexane as the eluant to give the title compound as a white solid (97 mg, 33% yield), mp 98–99° C. $^1$H NMR (CDCl$_3$) δ7.92 (d, J=6.8 Hz, 2H), 7.42 (d, J=7.6 Hz, 2H), 7.20 (m, 1H), 7.05–6.80 (m, 3H), 6.69 (s, 1H), 6.68 (s, 1H), 5.97 (s, 2H), 3.81 (s, 2H), 3.08 (s, 3H); $^{13}$C NMR (CDCl$_3$) δ162.3, 159.05, 147.7, 147.2, 146.2, 139.0, 133.4, 130.5, 130.3 (2×C), 127.9, 127.2 (2×C), 115.3, 115.0, 110.2, 109.7, 101.3,44.55, 31.8; LRMS (APIMS) m/z 402 (M+NH$_4$)$^+$.

4d. 2-Fluorophenyl 6-(4-(methylsulfonyl)phenyl)(2H-benzo(d)1,3-dioxolan-5-yl) ketone The product of Example 4b (310 mg, 0.775 mmol) and alumina (3 g) in anhydrous CH$_2$Cl$_2$ (20 mL) were stirred at room temperature. To this mixture, pyridinium chlorochromate (501 mg, 2.325 mmol) was added and the mixture stirred at room temperature for 15 minutes. The reaction mixture was diluted with CH$_2$Cl$_2$ and the alumina was removed by filtration. The filtrate was washed with water (3×55 mL), saturated aqueous sodium bicarbonate (2×55 mL), brine (1×50 mL), then dried over anhydrous sodium sulfate, filtered and the filtrate was evaporated under reduced pressure. Purification by flash column chromatography using ethyl acetate as the eluant gave the title compound as a white solid, (90 mg, 29% yield), mp 212–215° C. $^1$H NMR (CDCl$_3$) δ7.74 (d, J=6.4 Hz, 2H), 7.42–7.3 (m, 4H), 7.13 (s, 1H), 7.02 (t, J=7.6 Hz, 1H), 6.86 (d, J=9.3 Hz, 1H), 6.82 (s, 1H), 6.11 (s, 2H), 5.29 (s, 2H), 2.95 (s, 3H); LRMS (APIMS) m/z 399 (M+H)$^+$.

Example 5

3-Fluorophenyl 6-(4-(methylsulfonyl)phenyl)(2H-benzo(d)1,3-dioxolan-5-yl) ketone 5a. (3-Fluorophenyl)(6-(4-methylthiophenyl)(2H-benzo(d) 1,3-dioxolan-5-yl))methan-1-ol The Grignard reagent was prepared by refluxing 1-bromo-3-fluorobenzene (1.75 g, 10 mmol), magnesium metal (267 mg, 11 mmol) and a few crystals of iodine in anhydrous THF (40 mL) under nitrogen atmosphere until most of the magnesium metal was consumed. The reaction mixture was cooled to room temperature and to this solution the product of Example 1b (1.36 g, 5 mmol) in anhydrous THF (10 mL) was added and then stirred at room temperature overnight. The reaction was then quenched with saturated aqueous ammonium chloride, acidified with 1 N HCl and the organic layer was separated. The aqueous layer was extracted with ethyl acetate. The combined organic layers were dried over anhydrous sodium sulfate, filtered. The filtrate was concentrated under reduced pressure to give the crude product that was purified by flash column chromatography using 10% ethyl acetate in hexane as the eluant to give the title compound as a white solid, (1.03 g, 56% yield). mp 97–99° C. $^1$H NMR (CDCl$_3$) δ7.28–7.18 (m, 5H), 6.92 (m, 3H), 6.87 (s, 1H), 6.70 (s, 1H), 5.96 (d, J=1.8 Hz, 2H), 5.79 (d, J=3.6 Hz, 1H), 2.51 (s, 3H), 2.18 (d, J=3.8 Hz, 1H, OH); $^{13}$C NMR (CDCl$_3$) δ164.4, 161.1, 147.4, 146.6, 137.7, 137.2, 134.7, 134.4, 129.8 (2×C), 126.3 (2×C), 121.9, 114.0 (d, J=21 Hz), 113.3 (d, J=22 Hz), 109.8, 107.4, 101.3, 71.5, 15.7; LRMS (APIMS) m/z 386 (M+NH$_4$)$^+$, 754 (2 M+NH$_4$)$^+$.

5b. 1-(6-((3-Fluorophenyl)hydroxymethyl)(2H-benzo(3,4-d)1,3-dioxolan-5-yl))-4-(methylsulfonyl)benzene The product of Example 5a (770 mg, 2.09 mmol) was dissolved in MeOH (35 mL). To this solution, OXONE® (2.7 g, 4.4 mrnol) in water (10 mL) was added drop-wise. The reaction mixture was stirred at room temperature for 2 hours, diluted with water and ammonium hydroxide was added until the solution was basic. The solvent was evaporated under reduced pressure. The resulting product was extracted with ethyl acetate (2×75 mL), washed with brine (1×50 mL), dried over anhydrous sodium sulfate, filtered and the filtrate was evaporated under reduced pressure to give an oil which upon trituration with hexane gave the title compound (830 mg, 99% yield), mp 163–169° C. $^1$H NMR (CDCl$_3$) δ7.92 (d, J=8.4 Hz, 2H), 7.47 (d, J=8.4 Hz, 2H), 7.4 (m, 1H), 6.93 (s, 1H), 6.88 (m, 3H), 6.67 (s, 1H), 5.99 (d, J=1.8 Hz, 2H), 5.68 (d, J=3.2 Hz, 1H), 3.08 (s, 3H), 2.50 (d, J=3.8 Hz, 1H, OH); $^{13}$C NMR (CDCl$_3$) δ164.4, 161.1, 148.2, 147.2, 146.4, 139.4, 134.5, 133.2, 130.5 (2×C), 129.9 (d, J=8 Hz), 127.3 (2×C), 121.9, 114.2 (d, J=21 Hz), 113.3 (d, J=22 Hz), 109.5, 107.8, 101.6, 71.5, 44.5; LRMS (APIMS) m/z 418 (M+NH$_4$)$^+$.

5c. 1-(6-((3-Fluorophenyl)methyl)(2H-benzo(3,4-d)1,3-dioxolan-5-yl))-4-(methylsulfonyl)benzene The product of Example 5b (250 mg, 0.625 mmol) was dissolved in anhydrous dichloromethane (10 mL) at 0° C.

and under nitrogen atmosphere trifluoroacetic acid (5 mL) was added. The reaction mixture was stirred at 0° C. for 15 minutes. To the resulting dark orange color solution was then added, in small portions, sodium borohydride (555 mg, 15 mmol). The reaction mixture was stirred at 0° C. for 15 minutes and then at room temperature for 15 minutes. The solvent and trifluoroacetic acid were evaporated under reduced pressure and the residue was extracted with dichloromethane. The combined organic extracts were washed with water, brine, dried over sodium sulfate, filtered and the filtrate was evaporated under reduced pressure to give the crude product that was purified by silica gel column chromatography using 20% ethyl acetate in hexane to give the title compound as a white solid, (180 mg, 74% yield), mp 110–111° C. $^1$H NMR (CDCl$_3$) δ7.89 (d, J=8.4 Hz, 2H), 7.37 (d, J=8.3 Hz, 2H), 7.15 (m, 1H), 6.83 (dt, J=5.2 and 2.3 Hz, 1H), 6.70 (m, 3H), 6.60 (d, J=9.9 Hz, 1H), 5.99 (s, 2H), 3.8 (s, 2H), 3.08 (s, 3H); $^{13}$C NMR (CDCl$_3$) δ164.5, 161.2, 147.9, 146.4, 143.5, 139.1, 133.6, 130.9, 130.4 (2×C), 127.2(2×C), 124.2, 115.3, 129.9 (d, J=21.5 Hz), 113.9 (d, J=21 Hz), 110.6, 109.8, 101.4, 44.5, 38.6; LRMS (APIMS) m/z 402 (M+NH$_4$)$^+$.

5d. 3-Fluorophenyl 6-(4-(methylsulfonyl)phenyl)(2H-benzo(d)1,3-dioxolan-5-yl) ketone A suspension of the product Example 5b (360 mg, 0.9 mmol) and alumina (3 g) in anhydrous CH$_2$Cl$_2$ (50 mL) were stirred at room temperature. To this mixture, pyridinium chlorochromate (675 mg, 3 mmol) was added and the mixture stirred at room temperature for 1 hour. The reaction mixture was diluted with CH$_2$Cl$_2$, and the alumina was removed by filtration. The filtrate was washed with water (1×50 mL), saturated aqueous sodium bicarbonate (2×50 mL), brine (1×50 mL), then dried over anhydrous sodium sulfate, filtered and the filtrate was evaporated under reduced pressure. Purification by flash column chromatography using ethyl acetate as the eluant gave the title compound as a white solid, (270 mg, 75% yield), mp 205–209° C. $^1$H NMR (CDCl$_3$) δ 7.75 (d, J=8.3 Hz, 2H), 7.38–7.30 (m, 5H), 7.24 (t, J=5.2 Hz, 1H), 7.04 (s, 1H), 6.89 (s, 1H), 6.12 (s, 2H), 2.95 (s, 3H); $^{13}$C NMR (CDCl$_3$) δ195.5, 163.9, 160.7, 150.0, 147.7, 145.7, 139.7, 139.6, 135.1, 132.2, 129.9 (2×C), 129.3 (2×C), 125.6, 119.9 (d, J=21 Hz), 116.4 (d, J=22 Hz), 110.0 (d, J=35 Hz), 102.3, 44.4; LRMS (APIMS) m/z 399 (M+H)+, 416 (M+NH$_4$)$^+$.

Example 6

6-(4-(Methylsulfonyl)phenyl)(2H-benzo(d)1,3-dioxolan-5-yl) 3-pyridyl ketone 6a. (6-(4-Methylthiophenyl)(2H-benzo(d)-1,3-dioxolan-5-yl))-3-pyridylmethan-1-ol To a −78° C. cooled solution of 3-bromopyridine (632 mg, 4 mmol) in anhydrous THF (20 mL) was added t-BuLi (1.7 M, 4.64 mL, 8 mmol). The resulting dark blue solution was stirred at −78° C. for 10 minutes and then the product of Example 1b (820 mg, 3 mmol) in THF (15 mL) was added drop-wise. The reaction mixture was then stirred at −78° C. for 30 minutes, slowly allowed to warm to room temperature and stirred for an additional 30 minutes at room temperature. The reaction was quenched with saturated aqueous ammoniun chloride solution, the THF layer was separated. The aqueous layer was extracted with ethyl acetate. The combined organic layers were dried over sodium sulfate, filtered, and the filtrate was evaporated under reduced pressure to give the crude product. Purification by silica gel flash column chromatography using ethyl acetate/hexane (1:1) and then ethyl acetate as the eluants gave the title compound, (320 mg, 23% yield), mp 130–135° C. $^1$H NMR (CDCl$_3$) δ8.23 (d, J=4.3, Hz, 1H), 8.17 (s, 1H), 7.51 (d, J=7.8 Hz, 1H), 7.18 (d, J=8.1 Hz, 2H), 7.13 (m, 1H), 7.08 (d, J=8.1 Hz, 2H), 6.89 (s, 1H), 6.64 (s, 1H), 5.81 (d, J=3.0 Hz, 2H), 5.80 (s, 1H), 4.5 (br s, 1H, OH), 2.45 (s, 3H); $^{13}$C NMR (CDCl$_3$) δ147.8, 147.7, 147.4, 146.8, 140.0, 137.6, 137.1, 134.5, 134.4, 134.2, 129.7, 126.2, 123.1, 109.8, 107.3, 101.2, 60.3, 15.6; LRMS (APIMS) m/z 352 (M+H)$^+$.

6b. 1-(6-(Hydroxy-3-pyridylmethyl)(2H-benzo(3,4-d)1,3-dioxolan-5-yl))-4-(methylsulfonyl)benzene The product of Example 6a (501 mg, 1.45 mmol) was dissolved in MeOH (35 mL). To this solution, OXONE® (1.9 g, 2.9 mmol) in water (12 mL) was added drop-wise. The reaction mixture was stirred at room temperature for 2 hours, diluted with water and ammonium hydroxide was added until the solution was basic. The solvent was evaporated under reduced pressure. The resulting product was extracted with ethyl acetate (3×50 mL), washed with brine (1×50 mL), dried over anhydrous sodium sulfate, filtered and the filtrate was evaporated under reduced pressure to give the title compound that was used without further purification, (550 mg, 99% yield), mp 165–185° C. $^1$H NMR (CDCl$_3$) δ8.32 (br s, 1H), 7.88 (d, J=8.0 Hz, 2H), 7.5 (d, J=7.7 Hz, 1H), 7.41 (d, J=8.0 Hz, 2H), 7.18 (m, 1H), 6.91 (s, 1H), 6.65 (s, 1H), 5.99 (d, J=3.0 Hz, 2H), 5.71 (s, 1H), 3.95 (br s, 1H, OH), 3.07 (s, 3H); $^{13}$C NMR (CDCl$_3$) δ 148.2, 147.8, 147.3, 146.3, 139.45, 134.3, 134.1, 133.0, 130.5, 127.4, 123.3, 109.5, 107.8, 101.6, 69.9, 44.5; LRMS (APIMS) m/z 384 (M+H)$^+$.

6c. 4-(Methylsulfonyl)-1-(6-(3-pyridylmethyl)(2H-benzo(3,4-d)1,3-dioxolan-5-yl))benzene The product of Example 6b (540 mg, 1.41 mmol) was dissolved in anhydrous dichloromethane (5 mL) and under nitrogen atmosphere trifluoroacetic acid (10 mL) was added followed by triethylsilane (5 mL). The reaction mixture was stirred at room temperature overnight. The solvent and trifluoroacetic acid were evaporated under reduced pressure and the residue was extracted with dichloromethane. The combined organic extracts were washed with water, brine, dried over sodium sulfate and filtered. The filtrate was evaporated under reduced pressure to give the crude product that was purified by silica gel column chromatography using 5% methanol in dichloromethane as the eluant to give the title compound as a white solid, (255 mg, 41% yield), mp 121–137° C. $^1$H NMR (CDCl$_3$) δ 8.38 (d, J=4.0 Hz, 1H), 8.17 (s, 1H), 7.90 (d, J=8.2 Hz, 2H), 7.37 (d, J=8.2 Hz, 2H), 7.21 (d, J=7.9 Hz, 1H), 7.12 (dd, J=7.8 and 4.5 Hz, 1H), 6.7 (s, 1H), 6.68 (s, 1H), 5.99 (s, 2H), 3.81 (s, 2H), 3.08 (s, 3H); LRMS (APIMS) m/z 368 (M+H)$^+$.

6d. 6-(4-(Methylsulfonyl)phenyl)(2H-benzo(d)1,3-dioxolan-5-yl) 3-pyridyl ketone

A suspension of the product of Example 6b (80 mg, 0.209 mmol) and alumina (1 g) in anhydrous CH$_2$Cl$_2$ (10 mL) was stirred at room temperature. To this mixture, pyridinium chlorochromate (48 mg, 0.21 mmol) was added and the mixture stirred at room temperature for 15 minutes. The reaction mixture was diluted with CH$_2$Cl$_2$ and the alumina was removed by filtration. The filtrate was washed with water (3×25 ML), saturated aqueous sodium bicarbonate (2×25 mL), brine (1×25 mL), then dried over anhydrous sodium sulfate, filtered and the filtrate was evaporated under reduced pressure. Purification by flash column chromatography using ethyl acetate as the eluant gave the title compound as a white solid, (110 mg, 96.5% yield, mp 186–190° C. $^1$H NMR (CDCl$_3$) δ 8.7 (br s, 1H), 8.59 (br s, 1H), 7.91 (d, J=7.5 Hz, 1H), 7.75 (d, J=8.0 Hz, 2H), 7.40 (d, J=8.0 Hz, 2H), 7.25 (br s, 1H), 7.91 (d, H), 6.98 (s, 1H), 2.94 (s, 3H); LRMS (APIMS) m/z 382 (M+H)$^+$.

Example 7

4-(Methylsulfonyl)-1-(6-((3-((nitrooxy)methyl)piperidyl)methyl)(2H-benzo(3,4-d)1,3-dioxolan-5-yl))benzene 7a. (6-(4-Methylthiophenyl)-2H-benzo(d)1,3-dioxolene-5-yl)methan-1-ol.

The product of Example 1b (590 mg, 2.169 mmol) was dissolved in ethanol (30 mL) and sodium borohydride (160 mg, 4.338 mmol) was added. The reaction mixture was stirred at room temperature for 30 minutes. The solvent was evaporated under reduced pressure and the residue treated with water (25 mL), neutralized with 1 N HCl and extracted with ethyl acetate (2×50 mL). The combined organic extracts were washed with water (2×50 mL), brine (1×25 mL), dried over sodium sulfate, filtered and the filtrate was evaporated under reduced pressure to give the crude product (590 mg). Purification by silica gel column chromatography using 5% ethyl acetate in hexane as the eluant gave the title compound as a white solid, (340 mg, 66% yield), mp 95–97° C. $^1$H NMR (CDCl$_3$) δ 7.25 (m, 4H), 6.99 (s, 1H), 6.72 (s, 1H), 5.96 (s, 2H), 4.41 (s, 2H), 2.50 (s, 3H); $^{13}$C NMR (CDCl$_3$) δ 147.0, 146.8, 137.3, 137.1, 108.1, 101.1, 62.7, 15.7; LRMS (APIMS) m/z 292 (M+NH$_4$)$^+$.

7b. 1-(6-(Hydroxymethyl)(2H-benzo(3,4-d)1,3-dioxolen-5-yl)-4-(methylsulfonyl)benzene The product of Example 7a (260 mg, 0.95 mmol) was dissolved in dichloromethane (20 mL), saturated aqueous sodium bicarbonate (10 mL) was added followed by m-chlorobenzoic acid (548 mg, 60% yield). The reaction mixture was stirred at room temperature for 1 hour. The organic layer was separated. The aqueous layer was extracted with dichloromethane and the combined organic layers were washed with 10% sodium bicarbonate (3×25 mL), water (2×50 mL), brine (1×25 mL), dried over sodium sulfate, filtered and the filtrate was evaporated under reduced pressure to give the crude product. Purification by silica gel column chromatography using 10% ethyl acetate in hexane as the eluant gave the title compound as a white crystalline solid, (270 mg, 97% yield), mp 163° C. $^1$H NMR (CDCl$_3$) δ 7.95 (d, J=8.1 Hz, 2H), 7.55 (d, J=8.2 Hz, 2H), 7.03 (s, 1H), 6.72 (s, 1H), 6.00 (s, 2H), 4.43 (s, 2H), 3.09 (s, 3H), 2.1 (br s, 1H, OH); $^{13}$C NMR (CDCl$_3$) δ 147.9, 147.3, 146.3, 139.1, 133.3, 131.8, 130.3, 127.3, 109.7, 109.3, 101.4, 62.6, 44.5; LRMS (APIMS) m/z 324 (M+NH$_4$)$^+$.

7c. 6-(4-(Methylsulfonyl)phenyl)-2H-benzo(d)1,3-dioxolane-5-carbaldehyde

The product of Example 7b (4.6 g, 15 mmol) and alumina (10 g) in anhydrous CH$_2$Cl$_2$ (250 mL) were stirred at room temperature. To this mixture, pyridinium chlorochromate (6.75 g, 30 mmol) was added and the mixture stirred at room temperature for 15 minutes. The reaction mixture was then diluted with CH$_2$Cl$_2$ and the alumina was removed by filtration. The filtrate was washed with water (1×200 mL), saturated aqueous sodium bicarbonate (3×125 mL), brine (1×75 mL), then dried over anhydrous sodium sulfate, filtered and the filtrate was evaporated under reduced pressure. The resulting product was recrystallized from hexane/ethyl acetate (80 20) to give the title compound as a white solid, (4.1 g, 68% yield), mp 152–153° C. $^1$H NMR (CDCl$_3$) δ 9.74 (s, 1H), 8.06 (d, J=8.2 Hz, 2H), 7.59 (d, J=8.2 Hz, 2H), 7.51 (s, 1H), 6.86 (s, 1H), 6.16 (s, 2H), 3.16 (s, 3H); $^{13}$C NMR (CDCl$_3$) δ 189.3, 152.3, 148.5, 143.3, 140.9, 130.9 (2×C), 128.83, 127.4 (2×C), 110.0, 106.7, 102.4, 49.7, 44.4; LRMS (APIMS) m/z 322 (M+NH$_4$), 305 (M+H)$^+$.

7d. Ethyl (2E)-2-methyl-3-(6-(4-(methylsulfonyl)phenyl)(2H-benzo(d)1,3-dioxolan-5-yl))prop-2-enoate A mixture of carboethoxyethylidenetriphenyl phosphorane (720 mg, 2 mmol) and the product of Example 7c (410 mg, 1.34 mmol) in anhydrous THF (35 mL) were refluxed for 5 hours under nitrogen atmosphere. The reaction mixture was concentrated under reduced pressure and purified by column chromatography, using 20% ethyl acetate in hexane as the eluant, to give the title compound as a white powder, (290 mg, 56% yield), mp 165–173° C. $^1$H NMR (CDCl$_3$) δ 7.93 (d, J=8.2 Hz, 2H), 7.43 (d, J=8.2 Hz, 2H), 7.34 (s, 1H), 6.91 (s, 1H), 6.86 (s, 1H), 6.06 (s, 2H), 4.18 (q, J=7.1 Hz, 2H), 3.10 (s, 3H), 2.03 (s, 3H), 1.23 (t, J=7.1 Hz, 3H); $^{13}$C NMR (CDCl$_3$) δ 168.1, 147.9, 147.5, 145.0, 139.1, 137.8, 134.4, 130.5 (2×C), 128.8, 127.9, 127.1 (2×C), 109.9, 109.7, 101.7, 60.7, 44.5, 14.2; LRMS (APIMS) m/z 406 (M+NH$_4$)$^+$.

7e. 1-(6-((1E)-3-Hydroxy-2-methylprop-1-enyl)(2H-benzo(3,4-d)1,3-dioxolan-5-yl))-4-(methylsulfonyl)benzene To a stirred solution of the product of Example 7d (110 mg, 0.28 mmol) in anhydrous CH$_2$Cl$_2$ (4 mL) cooled to 0° C., was added diisobutylaluminium hydride (1 mL, 1 M in CH$_2$Cl$_2$). The reaction mixture was stirred at 0° C. for 15 minutes and then at room temperature for 15 minutes. The reaction was quenched with ice-cold water, neutralized with 1 N HCl and extracted with dichloromethane (2×50 mL). The combined organic extracts were washed with water (1×50 mL), brine (1×50 mL), dried over anhydrous sodium sulfate, filtered and the filtrate was evaporated under reduced pressure to give the title compound as a white solid, (90 mg, 93% yield), mp 140–141° C. $^1$H NMR (CDCl$_3$) δ 7.95 (d, J=8.4 Hz, 2H), 7.49 (d, J=8.4 Hz, 2H), 6.85 (s, 1H), 6.80 (s, 1H), 6.20 (s, 1H), 6.01 (s, 2H), 4.04 (s, 2H), 3.09 (s, 3H), 1.84 (s, 3H), 1.70 (br s, 1H, OH); $^{13}$C NMR (CDCl$_3$) δ 147.4, 147.0, 146.8, 138.6, 138.0, 133.1, 130.5, 129.7 (2×C), 127.0 (2×C), 123.9, 110.2, 109.7, 101.4, 68.2, 44.5, 15.2; LRMS (APIMS) m/z 364 (M+NH$_4$)$^+$.

7f. 4-(Methylsulfonyl)-1-(6-((3-((nitrooxy)methyl)piperidyl)methyl)(2H-benzo(3,4-d)1,3-dioxolan-5-yl))benzene To acetic anhydride (230 μL, 2.5 mmol) at 0° C. was added drop-wise, with stirring, fuming nitric acid (70 μL, 1.66 mmol). This mixture was immediately added drop-wise to a solution of the product of Example 7e (80 mg, 0.231 mmol) in anhydrous ethyl acetate (0.5 mL), at 0° C. The reaction mixture was stirred at 0° C. for 15 minutes and then at room temperature for 5 minutes. The reaction was treated with ice-cold water and extracted with ethyl acetate (2×50 mL). The combined organic extracts were washed with water (1×50 mL), brine (1×50 mL), dried over sodium sulfate, filtered and the filtrate was evaporated under reduced pressure to give the crude product. Purification by flash column chromatography using ethyl acetate:hexane (10:90) as an eluent gave the title compound as a white solid (55 mg in 17% yield), mp 87–89° C. $^1$H NMR (CDCl$_3$) δ 7.94 (d, J=8.3 Hz, 2H), 7.45 (d, J=8.3 Hz, 2H), 6.82 (s, 1H), 6.80 (s, 1H), 6.30 (s, 1H), 6.02 (s, 2H), 4.7 (s, 2H), 3.09 (s, 3H), 1.82 (s, 3H), 1.70; $^{13}$C NMR (CDCl$_3$) δ 147.6, 147.4, 146.2, 138.9, 133.1, 130.5, 130.0, (2×C), 129.5, 128.1, 127.1 (2×C), 109.7, 110.2, 101.5, 77.9, 44.4, 15.5; LRMS (APIMS) m/z 409 (M+NH$_4$)$^+$.

Example 8

4-(Methylsulfonyl)-1-(6-((3-((nitrooxy)methyl)piperidyl) methyl)(2H-benzo(3,4-d)1,3-dioxolan-5-yl))benzene 8a. 1-(6-(Chloromethyl)(2H-benzo(3,4-d)1,3-dioxolan-5-yl))-4-(methylsulfonyl)benzene To a solution of Example 7b (1.53 g, 5 mmol) in anhydrous benzene (35 mL) was added thionyl chloride (0.8 mL) followed by a catalytic amount of pyridine (3 to 4 drops).

The reaction mixture was stirred at room temperature overnight. The solvent was evaporated under reduced pressure, and the residue on addition of hexane gave a white solid. The product was used without further purification. The sample was characterized after purification by silica gel column chromatography using ethyl acetate hexane (1:1) as the eluant, mp 146–148° C. $^1$H NMR (CDCl$_3$) δ 8.00 (d, J=8.3 Hz, 2H), 7.6 (d, J=8.3 Hz, 2H), 6.99 (s, 1H), 6.71 (s, 1H), 6.02 (s, 2H), 4.38 (s, 2H), 3.11 (s, 3H); $^{13}$C NMR (CDCl$_3$) δ148.1, 145.7, 139.6, 134.1, 130.2, (2×C), 128.5, 127.4 (2×C), 110.3, 109.7, 101.7,44.4; LRMS (APIMS) m/z 324 (M+NH$_4$)$^+$.

8b. 1-(6-((3-(Hydroxymethyl)piperidyl)methyl)(2H-benzo (3,4-d)1,3-dioxolan-5-yl))-4-(methylsulfonyl)benzene The product of Example 8a (410 mg, 1.2 mmol) and 2-piperidine methanol (138 mg, 1.2 mmol) were dissolved in anhydrous DMF (5 mL). Potassium carbonate (830 mg, 6 mmol) was added and reaction mixture was stirred at room temperature overnight. The reaction mixture was then treated with ice-cold water and extracted with ethyl acetate (2×75 mL). The combined organic extracts were washed with water (1×50 mL), brine (1×50 mL), dried over sodium sulfate, filtered and the filtrate was evaporated under reduced pressure to give the crude product that was purified by flash column chromatography using methanol:dichloromethane (5:95) as an eluent to give the title compound as a white solid, (410 mg, 80% yield), mp 127–137° C. $^1$H NMR (CDCl$_3$) δ 7.92 (d, J=6.4 Hz, 2H), 7.56 (d, J=6.4 Hz, 2H), 7.26 (s, 1H), 6.67 (s, 1H), 5.98 (s, 2H), 3.45 (m, 2H), 3.21 (s, 2H). 3.10 (s, 3H), 2.63 (m, 1H), 2.42 (m, 1H), 1.90 (m, 3H), 1.63 (m, 3H), 1.45 (m, 1H), 1.21 (m, 1H), 1.07 (m, 1H); $^{13}$C NMR (CDCl$_3$) δ147.5, 147.4, 146.6, 138.8, 134.0, 130.5, 130.2, (2×C), 127.0 (2×C), 110.2, 109.7, 101.3, 66.7, 60.4, 56.9, 53.8,44.6, 38.2, 27.3, 24.6; LRMS (APIMS) m/z 404 (M+H)$^+$.

8c. 4-(Methylsulfonyl)-1-(6-((3-((nitrooxy)methyl) piperidyl)methyl)(2H-benzo(3,4-d) 1,3-dioxolan-5-yl)) benzene To acetic anhydride (230 μL, 2.5 mmol) at 0° C. was added fuming nitric acid (70 μL, 1.66 mmol). This mixture was immediately added drop-wise to a solution of the product of Example 8b (101 mg, 0.25 mmol) in anhydrous ethyl acetate (2 mL), at 0° C. The reaction mixture was stirred at 0° C. for 15 minutes and then at room temperature for 5 minutes. The reaction was treated with ice-cold water and extracted with ethyl acetate (2×50 mL). The combined organic extracts were washed with water (1×50 mL), brine (1×50 mL), dried over sodium sulfate, filtered and the filtrate was evaporated under reduced pressure to give the crude product. Purification by flash column chromatography using ethyl acetate:hexane (10:90) as an eluent gave the title compound as a white solid, (80 mg, 71% yield), mp 126–128° C. $^1$H NMR (CDCl$_3$) δ7.95 (d, J=8.4 Hz, 2H), 7.52 (d, J=8.4 Hz, 2H), 7.01 (s, 1H), 6.69 (s, 1H), 6.01 (s, 2H), 4.32 (s, 2H), 3.11 (s, 3H). 2.52–2.48 (m, 2H), 2.02–1.5 (m, 7H); $^{13}$C NMR (CDCl$_3$) δ147.7, 147.2, 146.7, 138.8, 134.0, 130.5 (2×C), 127.0 (2×C), 110.1, 109.7, 101.4, 60.0, 55.8, 53.4, 54.5, 44.5, 34.1, 31.6, 26.7, 24.0; LRMS (APIMS) m/z 449 (M+H)$^+$.

Example 9

1-((6-(4-Methylsulfonyl)phenyl)-2H-benzo(d)1,3-dioxolan-5-yl)methyl)piperidin-2-one 9a. (6-(4-Methylthiophenyl)-2H-benzo(d)1,3-dioxolen-5-yl)methylamine.

To a stirred mixture of the product of Example 1b (2.72 g, 10 mmol), 4° A molecular sieves (6 g), and NH$_4$OAc (11.6 g, 150 mmol) in MeOH (80 mL) was added sodium cyanoborohydride (0.95 g, 15 mmol). The reaction mixture was stirred at room temperature for 72 hours, filtered, and rinsed with MeOH. The filtrate was evaporated under reduced pressure. The resulting residue was dissolved in EtOAc (200 mL), washed with 2M aqueous sodium carbonate, dried over sodium sulfate, filtered, and the filtrated evaporated under reduced pressure. The crude product was purified by flash chromatography using MeOH:CH$_2$Cl$_2$ (1:9) with trace a amount of NH$_4$OH, as the eluant to give the title compound as a viscous oil which solidified on standing, (1.70 g, 62% yield), mp 42° C. $^1$H NMR (300 MHz, CDCl$_3$) δ7.28 (dd, J=6.5, 1.8 Hz, 2H), 7.20 (dd, J=6.5, 1.8 Hz, 2H), 6.94 (s, 1H), 6.69 (s, 1H), 5.96 (s, 2H), 3.67 (s, 2H), 2.51 (s, 3H), 1.53 (br, 2H); LRMS (APIMS) m/z 274 ((M+H)$^+$).

9b. 1-((6-(4-Methylthiophenyl)-2H-benzo(d)1,3-dioxolan-5-yl)methyl)piperidin-2-one To a stirred solution of the product of Example 9a (261 mg, 0.956 mmol) and methyl 5-bromovalerate (187 mg, 0.956 mmol) in toluene (3 mL) was added triethylamine (0.140 mL, 1.0 mmol). The reaction mixture was maintained at 70–80° C. for 14 hours and then the solvent was evaporated under reduced pressure. Purification by flash chromatography (0–2% gradient MeOH in CH$_2$Cl$_2$) gave the title compound as a white solid, (142 mg, 42% yield), mp 140–144° C; $^1$H NMR (300 MHz, CDCl$_3$) δ 7.27 (d, J=8.2 Hz, 2H), 7.16 (d, J=8.2 Hz, 2H), 6.79 (s, 1H), 6.68 (s, 1H), 5.97 (s, 2H), 4.51 (s, 2H), 2.92 (t, J=6.0 Hz, 2H), 2.51 (s, 3H), 2.39 (t, J=6.0 Hz, 2H), 1.74–1.67 (m, 4H); LRMS (APIMS) m/z 256 ((M+H)$^+$).

9c. 1-((6-(4-Methylsulfonyl)phenyl)-2H-benzo(d)1,3-dioxolan-5-yl)methyl)piperidin-2-one The product of Example 9b (142 mg, 0.400 mmol) was dissolved in MeOH. To this solution, OXONE® (0.74 g, 1.2 mmol) in water (6 mL was added. The reaction mixture was stirred at room temperature for 15 minutes, diluted with water, neutralized with saturated sodium bicarbonate and then extracted with EtOAc (2×). The organic extracts were dried over sodium sulfate, filtered, and the filtrate was evaporated under reduced pressure. The resulting solid was purified by recrystallization from EtOAc:Hexane (1:1) to give the title compound as white prisms, (108 mg, 70% yield), mp 156–157° C. $^1$H NMR (300 MHz, CDCl$_3$) δ 7.97 (d, J=8.4 Hz, 2H), 7.46 (d, J=8.4 Hz, 2H), 6.81 (s, 1H), 6.68 (s, 1H), 6.01 (s, 2H), 4.47 (s, 2H), 3.11 (s, 3H), 2.95 (t, J=60 Hz, 2H), 2.38 (t, J=60 Hz, 2H), 1.75–1.71 (m, 4H); $^{13}$C NMR (75 MHz, CDCl$_3$) δ 169.9, 148.2, 146.8, 146.4, 139.3, 133.4, 130.4, 128.4, 127.4, 109.6, 107.9, 101.4, 47.1, 44.5, 32.3, 23.1, 21.3; LRMS (APIMS) m/z 388 ((M+H)$^+$).

Example 10

4-(6-(Cyclopenthylmethyl)(2H-benzo(3,4-d)1,3-dioxolan-5-yl))-1-(methylsulfonyl)benzene 10a 4-(6-(Cyclopentylidenemethyl)(2H-benzo(3,4-d)1,3-dioxolan-5-yl))-1-(methylsulfonyl)benzene A suspension of cyclopentyl triphenyl phosphinebromide (1.24 g, 3 mmol) in anhydrous THF (15 mL) was stirred at 0° C. under nitrogen atmosphere. A solution of t-BuOK (2.5 mL of 1M in THF, 2.5 mmol) was added drop-wise and stirred for 15 minutes. To the resulting dark orange colored mixture, the product of Example 7a (3.04 g, 3 mmol) in anhydrous THF (10 mL) and DMF (10 μL) was added drop-wise. The reaction mixture was stirred at 0° C. for 30 minutes, then slowly allowed to warm to room temperature and stirred for 3 hours at room temperature. The reaction was quenched with saturated aqueous ammonium chloride and the organic layer was separated. The aqueous layer was diluted, extracted with ethyl acetate. The combined organic layers were dried over anhydrous sodium sulfate, filtered and the filtrate was concentrated under reduced pressure. Purification by flash column chromatography using 20% ethyl acetate in hexanes as the eluant gave the title compound as a white solid, (280 mg, 72% yield), mp 145–147° C. $^1$H NMR (CDCl$_3$, 300 MHz) δ7.94–7.91 (m, 2H), 7.51–7.48 (m, 2H), 7.26 (s, 1H), 6.97 (s, 1H), 6.75 (s, 1H), 6.00–5.97 (m, 3H), 3.11 (s, 3H), 2.41 (t, J=6.8 Hz, 2H), 2.31 (t, J=7.0 Hz, 2H), 1.77–1.54 (m, 4H). $^{13}$C NMR (CDCl$_3$, 75.45 MHz) δ147.4, 147.3, 146.9, 146.0, 138.5, 132.3, 131.1, 130.7, 126.9, 111.0, 109.6, 108.8, 101.2, 44.5, 34.8, 30.9, 26.8, 25.4. LRMS (APIMS) m/z 374 (M+NH$_4$)$^+$.

10.b 4-(6-(Cyclopenthylmethyl)(2H-benzo(3,4-d)1,3-dioxolan-5-yl))-1-(methylsulfonyl)benzene The product of Example 10a (220 mg, 0.57 mmol) was dissolved in EtOH (100 mL) and flushed with nitrogen for 15 minutes. To this solution, palladium on carbon (10% catalyst, 50 mg) was added. Hydrogenation was performed at 30–40 psi of hydrogen at room temperature overnight. The reaction mixture was filtered and the solvent removed under reduced pressure. Purification by flash column chromatography using ethyl acetate as the eluant gave the title compound as a white solid, (170 mg, 83% yield), mp 103–105° C. $^1$H NMR (CDCl$_3$, 300 MHz) δ 7.98–7.94 (m, 2H), 7.48–7.44 (m, 2H), 6.80 (s, 1H), 6.64–6.61 (m, 1H), 5.98 (s, 2H), 3.10 (s, 3H), 2.49–2.43 (m, 2H), 1.98–1.83 (m, 1H), 1.59–1.40 (m, 6H), 0.98–0.78 (m, 2H). $^{13}$C NMR (CDCl$_3$, 75.45 MHz) δ 148.0, 147.5, 145.5, 138.7, 133.5, 133.0, 130.7, 127.1, 109.7, 109.6, 101.1, 44.6, 41.9, 38.3, 32.3, 24.6. LRMS (APIMS) m/z 376 (M+NH$_4$)$^+$.

Example 11

4-(6-(Cycloheptylmethyl)(2H-benzo(3,4-d)1,3-dioxolan-5-yl))-1-(methylsulfonyl)benzene 11a. 4-(6-(Cycloheptylidenemethyl)(2H-benzo(3,4-d)1,3-dioxolan-5-yl))-1-methylthiobenzene A suspension of cycloheptyl triphenyl phosphine bromide (0.66 g, 1.5 mmol) in anhydrous THF (15 mL) was stirred at 0° C. under nitrogen atmosphere. A solution of n-BuLi (0.5 mL of 2.5 M in hexane, 1.25 mmol) was added drop-wise and stirred for 15 minutes. To the resulting dark orange colored mixture, the product of Example 1b (268 mg, 1 mmol) in anhydrous THF (5 mL) was added drop-wise. The reaction mixture was stirred at 0° C. for 30 min., then slowly allowed to warm to room temperature and stirred for 3 hours at room temperature. The reaction was then quenched with saturated aqueous ammonium chloride and the organic layer was separated. The aqueous layer was diluted with water, extracted with ethyl acetate. The combined organic layers were dried over anhydrous sodium sulfate, filtered and the filtrate concentrated under reduced pressure. Purification by flash column chromatography using 4% ethyl acetate in hexanes as the eluant gave the title compound as an oil (220 mg, 57% yield). $^1$H NMR (CDCl$_3$, 300 MHz) δ7.22 (s, 4H), 6.77 (d, J=3.1 Hz, 2H), 5.94 (s, 3H), 2.48 (s, 3H), 2.40–2.36 (m, 2H), 2.25–2.20 (m, 2H), 1.63–1.32 (m, 8H). $^{13}$C NMR (CDCl$_3$, 75.45 MHz) δ 146.2, 146.0, 143.4, 138.2, 136.6, 134.0, 130.4, 130.2, 125.9, 125.4, 109.9, 109.5, 100.9, 37.4, 31.1, 29.9, 28.9, 28.9, 27.0, 15.8.

11b. 4-(6-(Cycloheptylidenemethyl)(2H-benzo(3,4-d)1,3-dioxolan-5-yl))-1-(methylsulfonyl) benzene The product of Example 11a (200 mg, 0.57 mmol) was dissolved in MeOH (25 mL). To this solution, OXONE® (0.74 g, 1.2 mmol) dissolved in H$_2$O (4 mL) was added drop-wise while stirring under inert atmosphere. The reaction mixture was stirred at room temperature overnight, diluted with water, aqueous sodium hydroxide (1M) was added until the solution was basic and the solvent was removed under reduced pressure. The product was extracted with ethyl acetate (3×), washed with brine (1×50 mL), dried over anhydrous sodium sulfate, filtered and the filtrate was evaporated under reduced pressure. Purification by flash column chromatography using 10% ethyl acetate in hexanes as the eluant gave the title compound as a white solid (150 mg, 75%), mp 168–169° C. $^1$H NMR (CDCl$_3$, 300 MHz) δ 7.91 (d, J=8.3 Hz, 2H), 7.51 (d, J=8.2 Hz, 2H), 6.79 (d, J=2.1 Hz, 2H), 6.00 (s, 2H), 5.92 (s, 1H), 3.09 (s, 3H), 2.32 (t, J=14.4 Hz, 2H), 2.23–2.17 (m, 2H), 1.61–1.51 (m, 8H). $^3$C NMR (CDCl$_3$, 75.45 MHz) δ 147.3, 146.4, 145.0, 138.4, 132.5, 131.0, 130.7, 126.8, 124.5, 110.3, 109.5, 101.3, 44.6, 37.5, 31.2, 29.9, 29.0, 28.9, 26.9. LRMS (APIMS) m/z 402 (M+NH$_4$)$^+$.

11c. 4-(6-(Cycloheptylmethyl)(2H-benzo(3,4-d)1,3-dioxolan-5-yl))-1-(methylsulfonyl)benzene The product of Example 11b (110 mg, 0.29 mmol) was dissolved in EtOH (100 mL) and flushed with nitrogen for 15 minutes. To this solution, palladium on carbon (10%, 50 mg) was added. Hydrogenation was performed at 30–40 psi of hydrogen at room temperature for 4 hours. The reaction mixture was filtered and the solvent removed under reduced pressure. Purification by flash column chromatography using 50% ethyl acetate in hexanes as the eluant gave the title compound as a white solid, (90 mg, 80% yield), mp 89–92° C. $^1$H NMR (CDCl$_3$, 300 MHz) δ 7.91 (d, J=8.3 Hz, 2H), 7.39 (d, J=8.3 Hz, 2H), 6.72 (s, 1H), 6.57 (s, 1H), 5.92 (s, 2H), 3.07 (s, 3H), 2.33 (d, J=7.1 Hz, 2H), 1.53–1.14 (m, 11H), 0.90 (q, J=10.2 Hz, 2H). $^{13}$C NMR (CDCl$_3$, 75.45 MHz) δ 147.9, 147.4, 145.4, 138.6, 133.3, 132.8, 130.6, 127.0, 109.6, 109.4, 101.0, 44.4, 41.1, 40.4, 33.9, 28.1, 26.0. LRMS (APIMS) m/z 404 (M+NH$_4$)$^+$.

Example 12

6-(4-(methylsulfonyl)phenyl)(2H-benzo(d)1,3-dioxollan-5-yl)3-((nitrooxy)methyl)phenylketone 12a. (3-Methylphenyl)(6-(4-methylthiophenyl)(2H-benzo(d)1,3-dioxolan-5-yl))methan-1-ol The Grignard reagent was prepared by refluxing 3-bromo-1-methylbenzene (1.21 mL, 10 mmol), magnesium metal (240 mg, 10 mmol) and a few crystals of iodine in anhydrous THF (30 mL) under nitrogen atmosphere until most of the magnesium metal was consumed. The reaction mixture was cooled to room temperature and to this solution, the product of Example 1b (1.37 g, 5 mmol) dissolved in anhydrous THF (15 mL) was added and the reaction mixture was stirred for 2 hours at room temperature. The reaction was quenched with saturated aqueous ammonium chloride and the organic layer separated. The aqueous layer was extracted with ethyl acetate. The combined organic layers were dried over anhydrous sodium sulfate, filtered and the filtrate was evaporated under reduced pressure. Purification by flash column chromatography using 10% ethyl acetate in hexanes as the eluant gave the title compound as an oil, (1.15 g, 85% yield). $^1$H NMR (CDCl$_3$, 300 MHz) δ 7.26–7.12 (m, 5H), 7.02–6.95 (m, 4H) 6.68 (s, 1H), 5.94 (d, J=1.2 Hz, 2H), 5.77 (d, J=3.3 Hz, 1H), 2.50 (s, 3H), 2.29 (s, 3H), 2.16–2.13 (broad, 1H). $^{13}$C NMR (CDCl$_3$, 75.45 MHz) δ 147.3, 146.7, 143.8, 137.8, 137.4, 135.1, 134.6, 130.0, 128.1, 127.9, 127.0, 126.2, 123.4, 109.8, 107.5, 101.2, 72.1, 21.4, 15.8. LRMS (APIMS) m/z 746 (2M+NH$_4$)$^+$, 347 (M–OH)$^+$.

12b. 4-(6-(Hydroxy(3-methylphenyl)methyl)(2H-benzo(3,4-d)1,3-dioxolan-5-yl))-1-(methylsulfonyl)benzene The product of Example 12a (990 mg, 2.72 mmol) was dissolved in MeOH (200 mL). To this solution, OXONE® (4.93 g, 5.44 mmol) in water (10 mL) was added drop-wise. The reaction mixture was stirred at room temperature under nitrogen atmosphere, diluted with water, aqueous sodium hydroxide (1M) was added until the solution was basic and then the solvent was removed under reduced pressure. The resulting product was extracted with ethyl acetate (2×), washed with brine, dried over anhydrous sodium sulfate, filtered and the filtrate was evaporated under reduced pressure. Purification by flash column chromatography using 10% ethyl acetate in hexanes as the eluant gave the title compound as a white solid (1.07 g, 99% yield), mp 154° C. $^1$H NMR (CDCl$_3$, 300 MHz) δ7.93, (d, J=8.5 Hz, 2H), 7.46 (d, J=8.4 Hz, 2H), 7.16 (t, J=7.6 Hz, 1H), 7.05–7.04 (m, 2H), 6.95–6.90 (m, 2H), 6.68 (s, 1H), 6.01–6.00 (m, 2H), 5.68 (d, J=3.5 Hz, 1H), 3.09 (s, 3H), 2.29 (s, 3H), 2.04 (s, 1H). $^{13}$C NMR (CDCl$_3$, 75.45 MHz) δ148.0, 147.0 146.6, 143.4, 139.2, 138.1, 135.0, 133.0, 130.6, 128.3, 128.3, 127.2, 127.0, 123.4, 109.4, 107.8, 101.5, 72.2,44.5, 21.4. LRMS (APIMS) m/z 414 (M+NH$_4$)$^+$, 379 (M-OH)$^+$.

12c. 3-Methylphenyl 6-(4-(methylsulfonyl)phenyl)(2H-benzo(d)1,3-dioxolan-5-yl)ketone A suspension of the product of Example 12b (990 mg, 2.5 mmol) and alumina (3 g) in anhydrous CH$_2$Cl$_2$ (250 mL) were stirred at room temperature. To this mixture, pyridinium chlorochromate (1.61 g, 7.5 mmol) was added and the mixture stirred at room temperature for 15 minutes. The reaction mixture was diluted with CH$_2$Cl$_2$, and the alumina was removed by filtration. The filtrate was washed with water, saturated aqueous sodium bicarbonate, brine, then dried over anhydrous sodium sulfate, filtered and the filtrate was evaporated under reduced pressure. Purification by flash column chromatography using 15% ethyl acetate in hexanes as the eluant gave the title compound as a white solid (600 mg, 61% yield), mp 168–170° C. $^1$H NMR (CDCl$_3$, 300 MHz) δ 7.75 (d, J=8.3 Hz, 2H), 7.44–7.37 (m, 4H), 7.26–7.18 (m, 2H), 7.18 (s, 1H), 7.04 (s, 1H), 6.12 (s, 2H), 3.00 (s, 3H), 2.36 (s, 3H). $^{13}$C NMR (CDCl$_3$, 75.45 MHz) δ 196.9, 149.7, 147.5, 146.0, 139.0, 138.6, 137.5, 134.9, 133.8, 133.0, 130.3, 129.9, 128.2, 127.3, 127.2, 110.2, 109.8, 102.1, 44.4, 21.2.LRMS (APIMS) m/z 412 (M+NH$_4$)$^+$, 395 (M+H)$^+$.

12d. 6-(4-(methylsulfonyl)phenyl)(2H-benzo(d)1,3-dioxolan-5-yl)3-((nitrooxy)methyl)phenylketone To a solution of Example 12c (190 mg, 0.48 mmol) in CCl$_4$, N-bromosuccinimide (80 mg, <1 equiv.) and benzoyl peroxide (10–15 mg) were added and the resulting mixture was refluxed for 3 hours. The solvent was removed under reduced pressure, the residue was dissolved in acetonitrile (10 mL), AgNO$_3$ (230 mg, 1.5 mmol) was added and the reaction stirred overnight at room temperature. The solvent was removed under reduced pressure and the reaction mixture was partitioned between CH$_2$Cl$_2$ and H$_2$O. The organic layer was washed with brine, dried over anhydrous sodium sulfate, filtered and the filtrate was evaporated under reduced pressure to give the crude product. Purification by flash column chromatography using 20% ethyl acetate in hexanes as the eluant gave the title compound as a white foam (33 mg, 15% yield). $^1$H NMR (CDCl$_3$, 300 MHz) δ 7.72 (d, J=8.2 Hz, 2H), 7.65 (d, J=7.7 Hz, 1H), 7.57 (s, 1H), 7.43 (d, J=7.6 Hz, 1H), 7.36 (d, J=8.0 Hz, 3H), 7.07 (s, 1H), 6.91 (s, 1H), 6.91 (s, 2H), 5.33 (s, 2H), 2.94 (s, 3H). $^{13}$C NMR (CDCl$_3$, 75.45 MHz) δ 196.2, 150.1, 147.8, 145.6, 139.2, 138.2, 135.0, 133.1, 132.6, 132.3, 130.7, 130.1, 129.9, 128.9, 127.3, 110.1, 109.9, 102.3, 73.8, 44.3. LRMS (APIMS) m/z 473 (M+NH$_4$)$^+$.

Example 13

4-(6-(3-Methoxyphenyl)methyl)(2H-benzo(3,4-d)1,3-dioxolan-5-yl))-1-(methylsulfonyl)benzene 13a. (3-Methoxyphenyl)(6-(4-methylthiophenyl)(2H-benzo(d)1,3-dioxolan-5-yl))methan-1-ol The Grignard reagent was prepared by refluxing 3-bromoanisole (1.21 mL, 9 mmol), magnesium metal (216 mg, 9 mmol) and a few crystals of iodine in anhydrous THF (30 mL) under nitrogen atmosphere until most of the magnesium metal was consumed. The reaction mixture was cooled to room temperature and to this solution the product of Example 1b (0.82 g, 3 mmol) dissolved in anhydrous THF (15 mL) was added and then stirred for 2 hours at room temperature. The reaction was quenched with saturated aqueous ammonium chloride and the organic layer was separated. The aqueous layer was extracted with ethyl acetate. The combined organic layers were dried over anhydrous sodium sulfate, filtered and the filtrate concentrated under reduced pressure. Purification by flash column chromatography using 10% ethyl acetate in hexanes as the eluant gave the title compound as a white solid (1.09 g, 95%), mp 95° C. $^1$H NMR (CDCl$_3$, 300 MHz) δ 7.28–7.25 (m, 2H), 7.21 (s, 2H), 7.19 (s, 1H), 6.95 (d, J=0.5 Hz, 1H), 6.82–6.77 (m, 2H), 6.75 (s, 2H), 6.69 (d, J=0.9 Hz, 1H), 5.97–5.95 (m, 2H), 5.80 (d, J=3.8 Hz, 1H), 3.76 (d, J=0.9 Hz, 3H), 2.51 (d, J=0.9 Hz, 3H), 2.04–2.01 (m, 1H). $^{13}$C NMR (CDCl$_3$, 75.45 MHz) δ 159.6, 147.4, 146.8, 145.6, 137.5, 137.4, 134.9, 134.7, 130.0, 129.3, 126.3, 118.7, 112.6, 112.1, 109.8, 107.5, 101.2, 72.0, 55.2, 15.8. LRMS (APIMS) m/z 778 (2M+NH$_4$)$^+$, 363 (M-OH)$^+$.

13b. 1-(6-(Hydroxy(3-methoxyphenyl)methyl)(2H-benzo(3,4-d)1,3-dioxolan-5yl))-4-(methylsulfonyl)benzene The product of Example 13a (1.0 g, 2.63 mmol) was dissolved in MeOH (100 mL). To this solution, OXONE® (3.21 g, 5.26 mmol) dissolved in water (10 mL) was added drop-wise. The reaction mixture was stirred overnight under nitrogen atmosphere, diluted with water and ammonium hydroxide was added until the solution was basic. The solvent was evaporated under reduced pressure. The resulting product was extracted with ethyl acetate (3×), washed with brine, dried over anhydrous sodium sulfate, filtered and the filtrate was evaporated under reduced pressure. Purification by flash column chromatography using 40% ethyl acetate in hexanes as the eluant gave the title compound as a white solid (1.00 g, 93% yield), mp 154° C. $^1$H NMR (CDCl$_3$, 300 MHz) δ 7.92 (d, J=8.1 Hz, 2H), 7.47 (d, J=8.0 Hz, 2H), 7.23–7.1 (m, 1H), 7.01 (s, 1H), 6.77–6.67 (m, 4H), 5.99 (d, J=2.6 Hz, 2H), 5.67 (s, 1H), 3.75 (s, 3H), 3.08 (s, 3H), 2.32 (s, 1H). $^{13}$C NMR (CDCl$_3$, 75.45 MHz) δ 159.6, 148.0, 147.0, 146.5, 145.2, 139.2, 134.8, 133.0, 130.6, 129.4, 127.2, 118.7, 112.5, 112.3, 109.4, 107.7, 101.5, 72.0, 55.2, 44.5. LRMS (APIMS) m/z 430 (M+NH$_4$)$^+$.

13c. 3-Methoxyphenyl-6-(4-(methylsulfonyl)phenyl)(2H-benzo(d)1,3-dioxolan-5-yl) ketone A suspension of product of Example 13 b (500 mg, 1.2 mmol) and alumina (1 g) in anhydrous CH$_2$Cl$_2$ (250 mL) were stirred at room temperature. To this mixture, pyridinium chlorochromate (0.52 g, 2.4 mmol) was added and the mixture stirred for 30 minutes. The reaction mixture was diluted with CH$_2$Cl$_2$, and the alumina was removed by filtration. The filtrate was washed with water, saturated aqueous sodium bicarbonate, brine, then dried over anhydrous sodium sulfate, filtered and the filtrate was evaporated under reduced pressure. Purification by flash column chromatography using CH$_2$Cl$_2$ as the eluant gave the title compound as a white solid, (300 mg, 61% yield), mp 158° C. $^1$H NMR (CDCl$_3$, 300 MHz) δ 7.75 (d, J=8.3 Hz, 2H), 7.39 (d, J=8.3 Hz, 2H), 7.20–7.16 (m, 3H), 7.03 (s, 1H), 7.00–6.96 (m, 1H), 6.90 (s, 1H), 6.11 (s, 2H), 3.77 (s, 3H). 2.96 (s, 3H). $^{13}$C NMR (CDCl$_3$, 75.45 MHz) δ 196.5, 159.4, 149.7, 147.4, 145.9, 139.0, 138.8, 134.9, 132.8, 129.9, 129.2, 127.2, 122.8, 119.3, 114.0, 110.1, 109.7, 102.1, 55.4, 44.4. LRMS (APIMS) m/z 411 (M+H)$^+$.

13d. 4-(6-(3-Methoxyphenyl)methyl)(2H-benzo(3,4-d)1,3-dioxolan-5-yl))-1-(methylsulfonyl)benzene The product of Example 13c (160 mg, 0.39 mmol) was dissolved in EtOH (60 mL) and flushed with nitrogen for 15 minutes. To this solution, palladium on carbon (10% catalyst, 50 mg) was added. Hydrogenation was performed at 30–40 psi of hydrogen at room temperature overnight. The reaction mixture was filtered and the filtrate was evaporated under reduced pressure to give the title compound as a white solid (140 mg, 95% yield), mp 125–126° C. $^1$H NMR (CDCl$_3$, 300 MHz) δ 7.92 (s, 1H), 7.89 (s, 1H), 7.42 (s, 1H), 7.39 (s, 1H), 7.14 (t, J=7.9 Hz, 1H), 6.73–6.70 (m, 3H), 6.56–6.53 (m, 1H), 6.47 (s, 1H), 5.98 (s, 2H), 3.79 (s, 2H), 3.73 (s, 3H), 3.08 (s, 3H). $^{13}$C NMR (CDCl$_3$, 75.45 MHz) δ 159.6, 147.7, 147.3, 146.2, 142.6, 138.9, 133.4, 131.5, 130.4, 129.3, 127.2, 120.9, 114.7, 111.0, 110.6, 109.7, 101.3, 55.1, 44.5, 38.7. LRMS (APIMS) m/z 810 (2M+NH$_4$)$^+$, 397 (M+H)$^+$.

Example 14

2-Fluoro-5-methylphenyl6-(4-(methylsulfonyl) phenyl)(2H-benzo(d)1,3-dioxolan-5-yl)ketone 14a. (2-Fluoro-5methylphenyl)(6-(4-methylthiophenyl)(2H-benzo(d)1,3-dioxolen-5-yl))methan-1-ol To a solution of 3-bromo-4-fluorotoluene (0.7 mL, 5 mmol) in anhydrous THF (25 mL) at −78° C. under nitrogen atmosphere, a solution of t-BuLi in pentane (5.9 mL, 10 mmol) was added and the mixture stirred for 15 minutes. (color change observed). To this reaction mixture the product of Example 1b (1.34 g, 5 mmol), dissolved in anhydrous THF (20 mL), was added drop-wise and stirred at −78° C. for 15 minutes, then slowly allowed to warm to room temperature and stirred for 3 hours at room temperature. The reaction was then quenched with saturated aqueous ammonium chloride and the organic layer was separated. The organic layer was washed with brine, dried over anhydrous sodium sulfate, filtered and the filtrate was evaporated under reduced pressure. Purification by flash column chromatography using 5% ethyl acetate in hexanes as the eluant gave the title compound as a white solid, (1.42 g, 74% yield), mp 110° C. $^1$H NMR (CDCl$_3$, 300 MHz) δ 7.26–7.18 (m, 5H), 7.01–6.98 (m, 1H), 6.87 (s, 1H), 6.82-6.76 (m, 1H), 6.69 (s, 1H), 5.97 (s, 1H), 5.95 (s, 2H), 2.50 (s, 3H), 2.31 (s, 3H), 2.10 (s, 1H). $^{13}$C NMR (CDCl$_3$, 75.45 MHz) δ 159.5, 156.3, 147.1, 146.8, 137.4, 137.3, 135.0, 133.4, 133.4, 130.2, 129.8, 129.3, 129.2, 128.0, 127.9, 126.2, 115.0, 114.8, 110.0, 107.5, 101.2, 67.2, 20.8, 15.8. LRMS (APIMS) m/z 782 (2M+NH$_4$)$^+$, 365 (M−OH)$^+$.

14b. 4-(6-((2-Fluoro-5-methylphenyl)hydroxymethyl)(2H-benzo(3,4-d)1,3-dioxolan-5-yl))-(methylsulfonyl)benzene The product of Example 14a (1.32 g, 3.5 mmol) was dissolved in MeOH (150 mL). To this solution, OXONE® (4.32 g, 7 mmol) dissolved in water (15 mL) was added. The reaction mixture was stirred overnight under nitrogen atmosphere, diluted with water, and then aqueous sodium hydroxide (1M) was added until the solution was basic. The solvent was evaporated under reduced pressure. The resulting product was extracted with ethyl acetate (3×), washed with brine, dried over anhydrous sodium sulfate, filtered and the filtrate was evaporated under reduced pressure to give the title compound as a white solid (1.38 g, 95% yield), mp 169–171° C. $^1$H NMR (CDCl$_3$, 300 MHz) δ 7.93 (s, 1H), 7.90 (s, 1H), 7.50 (s, 1H), 7.47 (s, 1H), 7.26–7.22 (m, 1H), 7.00–6.98 (m, 1H), 6.94 (s, 1H), 6.80–6.74 (m, 1H), 6.67 (s, 1H), 6.00–5.99 (m, 2H), 5.88 (s, 1H), 3.10 (s, 3H), 2.31 (s, 3H), 2.25 (s, 1H). $^{13}$C NMR (CDCl$_3$, 75.45 MHz) δ 147.9 147.1, 146.4, 139.2, 133.7, 133.3, 130.5, 130.1, 129.6, 129.5, 127.7, 127.2, 115.0, 114.8, 109.6, 107.7, 101.5, 66.8, 44.5, 20.8. LRMS (APIMS) m/z 846 (2M+NH$_4$)$^+$, 432 (M+NH$_4$)$^+$.

14c. 2-Fluoro-5-methylphenyl6-(4-(methylsulfonyl)phenyl)(2H-benzo(d)1,3-dioxolan-5-yl)ketone A suspension of the product of Example 14b (700 mg, 1.7 mmol) and alumina (1 g) in anhydrous CH$_2$Cl$_2$ (250 mL) were stirred at room temperature. To this mixture, pyridinium chlorochromate (0.73 g, 5.1 mmol) was added and the mixture stirred for 30 minutes at room temperature. The reaction mixture was diluted with CH$_2$Cl$_2$, and the alumina removed by filtration. The filtrate was washed with saturated aqueous sodium bicarbonate, brine, then dried over anhydrous sodium sulfate, filtered and the filtrate was evaporated under reduced pressure. Purification by flash column chromatography using CH$_2$Cl$_2$ as the eluant gave the title compound as a white solid, (480 mg, 68% yield), mp 153–154° C. $^1$H NMR (CDCl$_3$, 300 MHz) δ 7.77 (s, 1H), 7.74 (s, 1H), 7.40 (s, 1H), 7.38 (s, 1H), 7.20–7.17 (m, 1H), 7.15-7.10 (m, 2H), 6.83 (s, 1H), 6.78–6.72 (m, 1H), 6.12 (s, 2H), 2.97 (s, 3H), 2.24 (3H). $^{13}$C NMR (CDCl$_3$, 75.45 MHz) δ 193.4, 150.2, 147.7, 146.0, 139.1, 135.6, 134.5, 134.4, 133.8, 133.7, 131.2, 130.1, 127.0, 116.04, 115.8, 110.2, 109.8, 102.2, 44.4, 20.3. LRMS (APIM-S) m/z 842.4 (2M+NH$_4$), 413 (M+H)$^+$.

Example 15

5-(1-(3',5'-Difluorophenyl)methyl)-1,2-methylenedioxy-4-(4-methylsulfonylphenyl)benzene 15a. 4-(1-(3',5'-Difluorophenyl)-1-hydroxymethyl)-1,2-methylenedioxy-5-(4-methylthiophenyl)benzene. (3,5-difluorophenyl)(6-(4-methylthiophenyl)(2H-benzo(d)1,3-dioxolan-5-yl))methan-1-ol The Grignard reagent was prepared by refluxing magnesium metal (170 mg, 6.98 mmol, 1.9 eq), dry THF (10 mL) and 3,5-difluorobromobenzene (1.42 g, 7.34 mmol). The reaction mixture was maintained at reflux for 2 hours or until all the magnesium metal was consumed. The resulting dark black solution was cooled to room temperature and to this solution the product of Example 1b (1.00 g, 3.67 mmol) was added as a solid. The reaction was then stirred at room temperature for 1hour then quenched by the addition of saturated aqueous NH$_4$Cl (3 mL). The reaction mixture was diluted with EtOAc, the aqueous layer was separated, made acidic with 10% HCl, and then extracted with EtOAc. The combined organic extracts were dried over sodium sulfate, filtered and the filtrate was concentrated under reduced pressure to give a pale yellow oil which slowly solidified. The resulting product was used for the next reaction without further purification.

15b. 4-(1-(3',5'-Difluorophenyl)-1-hydroxymethyl)-1,2-methylenedioxy-5-(4-methylsulfonylphenyl)benzene.

A mixture of MeOH:H$_2$O:CH$_2$Cl$_2$ (3:1:2, 60 μL), was added to the product of Example 15a. OXONE® (4.97 g, 8.08 mmol) was added at room temperature and the reaction mixture was stirred at room temperature for 16 hours. The reaction mixture was filtered through a pad of Celite, washed with CH$_2$Cl$_2$. The filtrate was evaporated under reduced pressure and the residue was dissolved in CH$_2$Cl$_2$. The organic layer was washed with water, saturated sodium bicarbonate, brine, dried over sodium sulfate, filtered, and the filtrate was evaporated under reduced pressure to give a pale yellow oil that was used without further purification.

15c. 5-(1-(3',5'-Difluorophenyl)methyl)-1,2-methylenedioxy-4-(4-methylsulfonylphenyl)benzene The product of Example 15b, dissolved in a minimal amount of $CH_2Cl_2$, and under argon atmosphere was added to trifluoroacetic acid at 0° C. and the reaction mixture was stirred at 0° C. for 15 minutes. To the resulting solution was then added, in small portions, sodium borohydride (1.39 g, 36.72 mmol). The reaction mixture was stirred at 0° C. for an additional 30 minutes. The solvent and trifluoroacetic acid were evaporated under reduced pressure to give a grayish foam. Ice-cold water (20 mL) was added to the foam and the aqueous layer was made basic (pH 8–9) by the addition of NaOH (50%). The aqueous layer was extracted with $CH_2Cl_2$ (2×) and the combined organic layers were dried over sodium sulfate, filtered and the filtrate was evaporated under reduced pressure to give a pale yellow semi-solid. Recrystallization from $CH_2Cl_2$/hexanes gave the title compound as a cream-colored solid (930 mg, 63% overall yield for 3 steps), mp 140–141° C. $^1$H NMR (CDCl$_3$) δ 7.91 (m, 2H), 7.36 (m, 2H), 6.71 (s, 1H), 6.70 (s, 1H), 6.59 (m, 1H), 6.42 (m, 2H), 6.02 (s, 2H), 3.80 (s, 2H), 3.09 (s, 3H); LRMS (APIMS) m/z 420 (M+NH$_4$)$^+$.

Example 16

4-(1-(3',5'-Difluorophenyl)-1-oxomethyl)-1,2-methylenedioxy-5-(4-methylsulfonylphenyl)benzene 16a. 4-(1-(3',5'-Difluorophenyl)-1-oxomethyl)-1,2-methylenedioxy-5-(4-methylsulfonylphenyl)benzene.

The product of Example 15b (1 g, 2.39 mmol) was dissolved in dry $CH_2Cl_2$ (50 mL). Celite (2 g) was added, followed by NaOAc (1.76 g, 21.50 mmol) and pyridinium chlorochromate (3.10 g, 14.32 mmol, 6.0 eq). The resulting mixture was stirred at room temperature for 2 hours. The reaction mixture was filtered through a plug of Florisil using EtOAc as the eluant. The filtrate was evaporated under reduced pressure to give a faint yellow oil. Trituration with Et$_2$O gave the title compound as a white crystalline solid (430 mg, 43.2% yield overall for 3 steps). $^1$H NMR (CDCl$_3$) δ 7.80 (m, 2H), 7.37 (m, 2H), 7.10 (m, 2H), 7.05 (s, 1H), 6.91 (s, 1H), 6.87 (m, 1H), 6.14 (s, 2H), 2.98 (s, 3H); LRMS (APIMS) m/z 434 (M+NH$_4$)$^+$.

Example 17

4-(1-(3',5'-Difluorophenyl)-1-oxomethyl)-1,2-hydroxy-5-(4-methylsulfonylphenyl)benzene 17a. 4,5-dimethoxy-2-(4-methylthiophenyl)benzaldehyde 2-Bromoveratraldehyde (25 g, 103.3 mmol) and 4-(methylthio)benzeneboronic acid (19.66 g, 118.5 mmol) were dissolved in toluene (550 mL) and sodium carbonate (2M, 103 μL, 206 mmol) was added. To this reaction mixture was added ethanol (50 mL) followed by tetrakis (triphenylphosphine)palladium (3.4 g, 2.5 mmol) and the reaction mixture was refluxed overnight under nitrogen atmosphere. The reaction mixture was cooled to room temperature, diluted with water (250 mL) and extracted with ethyl acetate (2×250 mL). The combined organic extracts were washed with water (4×250 mL), brine (1×250 mL), dried over sodium sulfate, filtered and the filtrate was evaporated under reduced pressure to give the crude product. The product was purified by trituration with ethyl acetate/hexane to give the title compound as a white solid (21.3 g, 85% yield), mp 114–115° C. $^1$H NMR (CDCl$_3$, 300 MHz) δ 9.83 (s, 1H), 7.64 (s, 1H), 7.43–7.23 (m, 4H), 6.83 (s, 1H), 3.98 (d, J=2.4 Hz, 6H), 2.55 (s, 3H). $^{13}$C NMR (CDCl$_3$, 75.45 MHz) δ 190.9, 153.4, 148.7, 1408, 138.9, 134.5, 134.1, 130.5, 130.1, 128.0, 128.0, 126.9, 126.1, 112.5, 108.7, 56.2, 56.1, 15.6. LRMS (APIMS) m/z 289 (M+H)$^+$.

17b. 4-(1-(3',5'-Difluorophenyl)-1-hydroxymethyl)-1,2-dimethoxy-5-(4-methylthiophenyl)benzene.

The Grignard reagent was prepared by refluxing magnesium metal (2.21 g, 91.06 mmol), dry THF (200 mL) and 3,5-difluorobromobenzene (11.04 mL, 95.85 mmol). The reaction mixture was maintained at reflux for 2 hours or until all the magnesium metal was consumed. The resulting dark black solution was cooled to room temperature, diluted with dry THF (100 mL) and to this solution the product of Example 17a (13.82 g, 47.92 mmol) was added as a solid. The reaction was then stirred at room temperature for 1 hour then quenched by the addition of saturated aqueous NH$_4$Cl (50 mL). The reaction mixture was diluted with EtOAc, the aqueous layer was separated, made acidic with 10% HCl, and then extracted EtOAc (2×). The combined organic extracts were dried over sodium sulfate, filtered and the filtrate was concentrated under reduced pressure to give a pale yellow oil which slowly solidified. The resulting product was used for the next reaction without further purification.

17c. 4-(1-(3',5'-Difluorophenyl)-1-hydroxymethyl)-1,2-dimethoxy-5-(4-methylsulfonylphenyl)benzene A mixture MeOH:H$_2$O:CH$_2$Cl$_2$ (3:1:2) was added to the product of Example 17b. OXONE® (64.81 g, 0.105 mol) was added at room temperature and the reaction mixture was stirred for 20 hours. The reaction mixture was filtered through a pad of Celite and washed with 1:1 MeOH:CH$_2$Cl$_2$. The filtrate was concentrated under reduced pressure and the residue was dissolved in CH$_2$Cl$_2$ The organic layer was washed with water, saturated sodium bicarbonate, brine, dried over sodium sulfate, filtered, and the filtrate was concentrated under reduced pressure to give a pale yellow oil that was used without further purification.

17d. 5-(1-(3',5'-Difluorophenyl)methyl)-1,2-dimethoxy-4-(4-methylsulfonylphenyl)benzene.

The product of Example 17c, dissolved in a minimal amount of CH$_2$Cl$_2$, and under argon atmosphere was added to trifluoroacetic acid (600 mL) at 0° C. and the reaction mixture was stirred at 0° C. for 15 minutes. To the resulting intense blue-green colored solution was added, in small portions, sodium borohydride (18.10 g, 0.479 mol). After completion of the sodium borohydride addition, the reaction mixture was stirred at 0° C. for an additional 1 hour. The solvent and trifluoroacetic acid were evaporated under reduced pressure to give a grayish foam. Ice cold water (500 mL) was added to the foam and the aqueous layer was made basic (pH 8–9) by the addition of 50% NaOH. The aqueous layer was extracted with CH$_2$Cl$_2$ (4×200 mL) and the combined organic layers were dried over sodium sulfate, filtered and the filtrate was evaporated under reduced pressure to give the title compound as an off-white solid (18.74 g, 93.4% overall yield for the 3 steps), mp 157–159° C. $^1$H NMR (CDCl$_3$) δ 7.92 (m, 2H), 7.40 (m, 2H), 6.75 (s, 1H), 6.73 (s, 1H), 6.59 (m, 1H), 6.44 (m, 2H), 3.89 (s, 6H), 3.86 (S, 2H), 3.09 (s, 3H); LRMS (APIMS) m/z 436 (M+NH$_4$)$^+$.

17e. 5-(1-(3',5'-Difluorophenyl)methyl)-1,2-dihydroxy-4-(4-methylsulfonylphenyl)benzene To the product of Example 17d (18.74 g, 44.78 mmol) and dry CH$_2$Cl$_2$ (500 mL), cooled to 0° C. was added boron tribromide (0.112 mol, 10.6 mL) over a period of 2–3 minutes. The resulting dull red turbid solution was stirred at 0° C. for 45 minutes. The reaction was quenched at 0° C. by the addition of MeOH (70 mL) followed a minute later by the addition of water (70 mL). The reaction mixture was warmed to room temperature. The solvent (CH$_2$Cl$_2$ and MeOH) was evaporated under reduced pressure to give a solid. The solid was removed by filtration, washed with water and then dried under high vacuum overnight to give the title compound as a pale yellow solid, (17.0 g, 97.2% yield) mp 214° C. (dec). $^1$H NMR (DMSO-d$_6$) δ 9.15 (s, 1H), 9.13 (s, 1H), 7.90 (m, 2H), 7.47 (m, 2H), 6.99 (m, 1H), 6.64 (s, 1H), 6.62 (s, 1H), 6.60 (m, 2H), 3.81 (s, 2H), 3.24 (s, 3H); LRMS (APIMS) m/z 408 (M+NH$_4$)$^+$.

17f. 1,2-(Bis(ethoxycarbonyl))methylenedioxy-5-(1-(3',5'-difluorophenyl)methyl)--4-(4-methylsulfonylphenyl)benzene The product of Example 17e (530 mg, 1.36 mmol) was dissolved in dry acetone (10 mL). Potassium carbonate (563 mg, 4.07 mmol) was added at room temperature followed by diethyl 2,2-dibromomalonate (475 mg, 1.49 mmol). The slurry was stirred at room temperature for 18 hours. The solids were removed by filtration through Celite and washed with acetone. The solvent was evaporated under reduced pressure and the residue was purified by silica gel flash column using EtOAc:hexanes (1:3, 250 mL), then EtOAc:hexanes (1:1, 250 mL) and finally EtOAc (250 mL) as the eluants, to give the title compound as a white solid, (435 mg, 60.0% yield), mp 49–51° C. $^1$H NMR (CDCl$_3$) δ 7.93 (m, 2H), 7.37 (m, 2H), 6.83 (s, 1H), 6.82 (s, 1H), 6.60 (m, 1H), 6.41 (m, 2H), 4.40 (q, J=7.1 Hz, 4H), 3.81 (s, 2H), 3.10 (s, 3H), 1.37 (t, J=7.1 Hz, 6H); LRMS (APIMS) m/z 564 (M+NH$_4$)$^+$.

17 g. 4-(1-(3',5'-Difluorophenyl)-1-oxomethyl)-1,2-dimethoxy-5-(4-methylsulfonylphenyl)benzene The product of Example 17f (13.5 g, 31.07 mmol) was dissolved in dry CH$_2$Cl$_2$ (1 L). Celite (40 g) was added, followed by pyridinium dichromate (29.2 g, 77.68 mmol). The resulting mixture was stirred at room temperature for 24 hours. The reaction mixture was filtered through a plug of Florisil using EtOAc as the eluant. The filtrate was evaporated under reduced pressure to give a faint yellow solid. The solid was dissolved in a minimal amount of CH$_2$Cl$_2$ and then diluted with Et$_2$O (6-fold excess). The resulting crystals were filtered and washed with Et$_2$O to give the title compound as a pale yellow solid, (8.77 g, 65% yield) (hydrate), mp 175–176° C. $^1$H NMR (CDCl$_3$) δ 7.80 (m, 2H), 7.41 (m, 2H), 7.12 (s, 1H), 7.09 (m, 2H), 6.92 (s, 1H), 6.84 (m, 1H), 4.00 (s, 3H), 3.96 (s, 3H), 2.98 (s, 3H); LRMS (APIMS) m/z 450 (M+NH$_4$)$^+$.

17 h. 4-(1-(3',5'-Difluorophenyl)-1-oxomethyl)-1,2-hydroxy-5-(4-methylsulfonylphenyl)benzene To the product of Example 17 g (3.65 g, 8.44 mmol) and CH$_2$Cl$_2$ (70 ml), cooled to 0° C., was added boron tribromide (29.54 mmol, 2.80 mL) over a period of 2 minutes. The resulting dull red turbid solution was stirred at 0° C. for 2.5 hours. The reaction mixture was quenched at 0° C. by the addition of MeOH (6 mL). The reaction mixture was warmed to room temperature and stirred overnight at which point a precipitate formed. The solid was removed by filtration and washed with Et$_2$O to give a white solid (1.3 g). The filtrate was evaporated under reduced pressure and the resulting solid was removed by filtration and washed with Et$_2$O. The solids were combined to give the title compound, (3.0 g, 88% yield), mp 199–200° C. (dec). $^1$H NMR (DMSO-d6) δ 10.03 (s, 1H), 9.68 (s, 1H), 7.76 (m, 2H), 7.42 (m, 1H), 7.40 (m, 2H), 7.19 (m, 2H), 7.02 (s, 1H), 6.89 (s, 1H), 5.75 (s, 2H), 3.15 (s, 3H); LRMS (APIMS) m/z 422 (M+NH$_4$)$^+$.

Example 18

(7-((3,5-Difluorophenyl)methyl)-6-(4-(methylsulfonyl)phenyl)(2H, 3H-benzo(e)1,4-dioxin-2-yl))-N-(2-(nitrooxy)ethyl)carboxamide 18a. Ethyl 7-((3,5-difluorophenyl)methyl)-6-(4-(methylsulfonyl)phenyl)-2H, 3H-benzo(e)1,4-dioxin-2-carboxylate and ethyl 6-((3, 5-difluorophenyl)methyl)-7-(4-(methylsulfonyl)phenyl)-2H, 3H-benzo(e)1,4-dioxin-2-carboxylate To a stirred mixture of the product of Example 17e (1.04 g, 2.66 mmol) and ethyl 2,3-dibromopropionate (2.93 mmol, 0.76 g) in dry acetone (100 mL) was added powdered potassium carbonate (7.7 mmol, 1.07 g). The mixture was heated at reflux for four hours, then additional ethyl 2,3-dibromopropionate (0.38 g) and potassium carbonate (0.53 g) were added, and the mixture refluxed overnight. The reaction mixture was cooled, filtered through Celite and washed with acetone. The filtrate was evaporated under reduced pressure, and the resulting residue was partitioned between ethyl acetate and water. The organic layer was separated, washed with brine, dried over magnesium sulfate, filtered and the filtrate evaporated to dryness. Trituration with ether/hexane gave the title compound as an off-white crystal (1.054 g, 81% yield). HPLC analysis (Waters Symmetry® C18 column, 4.6×250 cm, acetonitrile:water, 60:40, flow rate 1 mL/min.) showed a mixture of regioisomers in a ratio of 56:44.: mp 162–165° C. $^1$H NMR (300 MHz, CDCl$_3$) δ7.91 (d, J=8.4 Hz, 2H), 7.37 (d, J=8.4 Hz, 1H), 7.36 (d, J=8.4 Hz, 1H), 6.92 (s, 0.5H), 6.89 (s, 0.5H), 6.78 (s, 0.5H), 6.75 (s, 0.5H), 6.59 (tt, J=2.3, 9.9 Hz, 1H), 6.42 (m, 2H), 4.87 (t, J=4.0 Hz, 1H), 4.43 (m, 2H), 4.31 (q, J=7.2 Hz, 1H), 4.29 (q, J=7.2 Hz, 1H), 3.80 (s, 1H), 3.79 (s, 1H), 3.10 (s, 1.5H), 3.09 (s, 1.5H), 1.32 (t, J=7.2 Hz, 1.5H), 1.31 (t, J=7.2 Hz, 1.5H); MS (APIMS) m/z 489 (M+H)$^+$, 506 (M+18)$^+$.

18b. (7-((3,5-Difluorophenyl)methyl)-6-(4-(methylsulfonyl)phenyl)(2H, 3H-benzo(e)1, 4-dioxin-2-yl))-N-(2-hydroxyethyl)carboxamido To the product of Example 18a (0.27 g, 0.55 mmol) was added 2-aminoethanol (10 mL, neat), and the mixture was heated at 60° C., for 2 hours. The reaction mixture was diluted with ethyl acetate and water followed by 3N HCl until the aqueous layer was acidic. The organic layer was separated, dried over magnesium sulfate, filtered and the filtrate was evaporated under reduced pressure. The resulting solid was recrystallized from dichloromethane/hexane to give the title compound, (0.128 g, 46% yield). HPLC analysis (Waters Symmetry® C18 column, 4.6×250 cm, acetonitrile:water, 50:50, flow rate 1 mL/min.) revealed predominantly one regioisomer, in a ratio of 93:7. mp 237–240° C. $^1$H NMR (300 MHz, DMSO-d$_6$) δ8.13 (t, J=5.6 Hz, 1H), 7.92 (d, J=8.3 Hz, 2H), 7.50 (d, J=8.3 Hz, 2H), 6.99 (tt, J=2.3, 9.4 Hz, 1H), 6.89 (s, 1H), 6.80 (s, 1H), 6.60 (m, 2H), 4.82 (dd, J=2.6, 6.5 Hz, 1H), 4.71 (br.t, 1H), 4.41 (dd, J=2.6, 11.5 Hz, 1H), 4.21 (dd, J=6.5 Hz, 11.5, 1H), 3.88 (s, 2H), 3.43 (m, 2H), 3.31 (s, 2H), 3.24 (s, 3H), 3.19 (m, 2H); MS (APIMS) m/e 504 (M+H)$^+$.

18c. (6-((3,5-Difluorophenyl)methyl)-7-(4-(methylsulfonyl)phenyl)(2H, 3H-benzo(e)1, 4-dioxin-2-yl))-N-(2-hydroxyethyl)carboxamide The supernatant from the crystallization of the product of Example 18b was evaporated under reduced pressure to give a thick oil (0.072 g, 26% yield). Analysis by HPLC analysis (Waters Symmetry® C18 column, 4.6×250 cm, acetonitrile:water, 50:50, flow rate 1 mL/min.) showed that the oil obtained was predominantly the opposite regioisomer, in a ratio of 19:81.: $^1$H NMR (300 MHz, DMSO-d$_6$) δ 8.09 (t, J=5.7 Hz, 1H), 7.93 (d, J=8.3 Hz, 2H), 7.50 (d, J=8.3 Hz, 2H), 6.97 (tt, J=2.3, 9.4 Hz, 1H), 6.88 (s, 1H), 6.85 (s, 1H), 6.55 (m, 2H), 4.83 (dd, J=2.7, 6.0 Hz, 1H), 4.71 (br s, 1H), 4.39 (dd, J=2.7, 11.6 Hz, 1H), 4.25 (dd, J=6.0, 11.6 Hz, 1H), 3.88 (s, 2H), 3.42 (m, 2H), 3.32 (s, 2H), 3.25 (s, 3H), 3.19 (m, 2H); MS (APIMS) m/e 504 (M+H)$^+$.

18d. (7-((3,5-Difluorophenyl)methyl)-6-(4-(methylsulfonyl)phenyl)(2H, 3H-benzo(e)1, 4-dioxin-2-yl))-N-(2-(nitrooxy)ethyl)carboxamido To acetic anhydride (0.460 mL) at 0° C. was added drop-wise, with stirring, fuming nitric acid (0.140 mL). This mixture was immediately added drop-wise to a solution of the product of Example 18b (0.43 mmol, 0.216 g) dissolved in ethyl acetate (5 mL), at 0° C. The resulting solution was stirred at 0° C. for 30 min, then quenched with water and neutralized with sodium carbonate. The organic layer was separated, dried over magnesium sulfate and filtered. The filtrate was evaporated under reduced pressure. Purification by silica gel column chromatography using ethyl acetate as the eluant gave the title compound as an amorphous glassy solid (0.217 g, 92% yield). $^1$H NMR (300 MHz, CDCl$_3$) δ7.95 (d, J=8.0 Hz, 2H), 7.39 (d, J=8.0 Hz, 2H), 6.88 (m, 3H), 6.61 (t, J=8.8 Hz, 1H), 6.43 (m, 2H), 4.79 (m, 1H), 4.61 (m, 3H), 4.28 (dd, J=7.3, 11.4 Hz, 1H), 3.83 (s, 2H), 3.12 (s, 3H); MS (APIMS) m/e 503 (M+H–NO2)$^+$, 566 (M+18)$^+$.

Example 19

1-(7-((3,5-Difluorophenyl)methyl)-2-((nitrooxy)methyl)(2H, 3H-benzo(3,4-e)1,4-dioxin-6-yl))-4-(methylsulfonyl)benzene and 1-(7-((3,5-difluorophenyl)methyl)-3-((nitrooxy)methyl)(2H, 3H-benzo(e)1,4-dioxin-6-yl))-4-(methylsulfonyl)benzene 19a. 1-(7-((3,5-Difluorophenyl)methyl)-2-(hydroxymethyl)(2H, 3H-benzo(3,4-e)1,4-dioxin-6-yl))-4-(methylsulfonyl)benzene and 1-(7-((3,5-difluorophenyl)methyl)-3-(hydroxymethyl)(2H, 3H-benzo(e)1,4-dioxin-6-yl))-4-(methylsulfonyl)benzene To a stirred solution of 2N potassium hydroxide (5 mL) at room temperature was added the product of Example 17e (1.0 g, 2.56 mmol) as a solid. The mixture turned yellow, then yellow-brown as most of the solid dissolved. Epichlorohydrin (3.40 mmol, 0.315 g, 0.266 mL) was added neat, at room temperature. The resulting mixture was heated to 70° C. for two hours, then stirred overnight at room temperature. The reaction mixture was diluted with water and 3N HCl was added to neutralize the mixture. Ethyl acetate was added until the solid dissolved. The organic layer was separated, washed with brine, dried over magnesium sulfate, filtered and the filtrate was concentrated under reduced pressure. The resulting residue was purified by column chromatography using hexane:ethyl acetate (1:1) as the eluant to give the title compound (0.65 g, 57% yield). HPLC analysis (Waters Symmetry® C18 column, 4.6×250 cm, acetonitrile: water, 60:40, flow rate 1 mL/min) showed a mixture of regioisomers in a ratio of 48:52. mp 133–144° C.; $^1$H NMR (300 MHz, CDCl$_3$) δ7.9 (d, J=7.4 Hz, 2H), 7.36 (d, J=8.3 Hz, 1H), 7.35 (d, J=8.3 Hz, 1H), 6.80 (s, 0.5H), 6.78 (s, 0.5H), 6.77 (s, 0.5H), 6.76 (s, 0.5H), 6.58 (m, 1H), 6.42 (m, 2H), 4.33 (m, 2H), 4.16 (m, 1H), 3.91 (m, 2H), 3.79 (s, 2H), 3.09 (s, 3H), 2.00 (t, J=5.9 Hz, 1H); MS (APIMS) m/e 447 (M+H)$^+$, 464 (M+18)$^+$.

19b. 1-(7-((3,5-Difluorophenyl)methyl)-2-((nitrooxy)methyl)(2H, 3H-benzo(3,4-e)1, 4-dioxin-6-yl))-4-(methylsulfonyl)benzene and 1-(7-((3,5-difluorophenyl)methyl)-3-((nitrooxy)methyl)(2H, 3H-benzo(e)1,4-dioxin-6-yl))-4-(methylsulfonyl)benzene To acetic anhydride (0.230 mL) at 0° C. was added drop-wise, with stirring, fuming nitric acid (0.07 mL). This mixture was immediately added drop-wise to a solution of the product of Example 19a (0.25 mmol, 0.112 g) dissolved in ethyl acetate, at 0° C. The resulting solution was stirred at 0° C. for 15 min, then quenched with water and neutralized with sodium carbonate. The organic layer was separated, dried over magnesium sulfate and filtered. The filtrate was concentrated under reduced pressure. Purification by silica gel column chromatography using ethyl acetate as the eluant gave the title compound as an amorphous glassy solid, (69 mg, 56% yield). $^1$H NMR (300 MHz, CDCl$_3$) δ7.91 (d, J=8.3 Hz, 2H), 7.35 (d, J=8.3 Hz, 2H), 6.81 (s, 0.5H), 6.80 (s, 0.5H), 6.79 (s, 0.5H), 6.78 (s, 0.5H), 6.59 (tt, J=2.3, 9.0 Hz, 1H), 6.41 (m, 2H), 4.73 (m, 2H), 4.57 (m, 1H), 4.35 (m, 1H), 4.18 (dd, J=3.2, 6.2 Hz, 0.5H), 4.14 (dd, J=3.2, 6.2 Hz, 0.5H), 3.79 (s, 2H), 3.09 (s, 3H); MS (APIMS) m/e 509 (M+18)$^+$.

Example 20

1-(7-((3,5-Difluorophenyl)methyl)(2H, 3H-benzo(3,4-e)1,4-dioxin-6-yl))-4-(methylsulfonyl)benzene To a stirred mixture of the product of Example 17e (0.400 g, 1.02 mmol) and 1,2-dibromoethane (0.21 g, 0.140 mL, 1.13 mmol) in dry acetone (50 mL) was added powdered potassium carbonate (2.96 mmol, 0.409 g). The mixture was heated at reflux for four hours, then additional 1,2-dibromoethane (0.105 g, 0.070 mL) and potassium carbonate (0.205 g) were added, and the mixture refluxed overnight. The reaction mixture was cooled, filtered through Celite and washed with acetone. The filtrate was evaporated under reduced pressure, and the resulting residue was partitioned between ethyl acetate and water. The organic layer was separated, washed with brine, dried over magnesium sulfate, filtered and the filtrate was evaporated to near dryness. Addition of ether resulted in the formation of off-white crystals of the title compound, (0.308 g, 73% yield), mp 160–162° C. $^1$H NMR (300 MHz, CDCl$_3$) δ7.93 (td, J=1.9, 8.4 Hz, 2H), 7.39 (td, J=1.9, 8.4 Hz, 2H), 6.80 (s, 1H), 6.78 (s, 1H), 6.61 (tt, J=2.3, 9.0 Hz, 1H), 6.45 (m, 2H), 4.34 (s, 4H), 3.82 (s, 2H), 3.12 (s, 3H); MS (APIMS) m/e 434 (M+18)$^+$.

Example 21

7-((3,5-Difluorophenyl)methyl)-6-(4-(methylsulfonyl)phenyl)-2H, 3H-benzo(e)1,4-dioxin-2-carboxamide To a solution of the product of Example 18a (1.094 g, 2.2 mmol) in ethanol (20 mL) and and tetrahydrofuran (10 mL) was added concentrated ammonium hydroxide solution (15 mL). The mixture was heated at 70° C. overnight. The reaction mixture was cooled, the solvent was evaporated under reduced pressure and the resulting residue was partitioned between dichloromethane and water. The organic layer was dried over magnesium sulfate, filtered and the filtrate was evaporated under reduced pressure. The residue was re-dissolved in ethyl acetate, and crystals slowly formed to give the title compound as white crystals (0.209 g, 21% yield). NMR analysis shows only one regioisomer is present. mp 238–241° C.; $^1$H NMR (300 MHz, DMSO-d$_6$) δ7.93 (d, J=8.3 Hz, 2H), 7.55 (d, J=5.1 Hz, 2H), 7.50 (d, J=8.3 Hz, 2H), 6.97 (tt, J=2.3, 9.4H), 6.87 (s, 1H), 6.84 (s, 1H), 6.55 (m, 2H), 4.80 (dd, J=3.5, 4.8 Hz, 1H), 4.34 (m, 2H), 3.87 (s, 2H), 3.24 (s, 3H); MS (APIMS) m/e 477 (M+18)$^+$.

Example 22

3,5-Difluorophenyl 7-(4-(methylsulfonyl)phenyl)(2H, 3H-benzo(e)1,4-dioxin-6-yl) ketone To a stirred mixture of the product of Example 17 h (0.412 g, 1.02 mmol) and 1,2-dibromoethane (1.13 mmol, 0.21 g, 0.140 mL) in dry acetone (50 mL) was added powdered potassium carbonate (2.96 mmol, 0.409 g). The mixture was heated at reflux for 4 hours, then additional 1,2-dibromoethane (0.105 g, 0.070 mL) and potassium carbonate (0.205 g) were added, and the mixture refluxed overnight. The reaction mixture was cooled, filtered through Celite and washed with acetone. The filtrate was evaporated under reduced pressure, and the resulting residue was partitioned between dichloromethane and water. The organic layer was separated, washed with brine, dried over magnesium sulfate, filtered and the filtrate evaporated to dryness. Recrystallization from dichloromethane/hexane gave the title compound as off-white crystals, (0.242 g, 55% yield, mp 191–193° C. $^1$H NMR (300 MHz, CDCl$_3$) δ7.80 (d, J=8.3 Hz, 2H), 7.38 (d, J=8.3 Hz, 2H), 7.15 (m, 2H), 7.12 (s, 1H), 6.98 (s, 1H), 6.89 (tt, J=2.3, 8.4 Hz, 1H), 4.38 (m, 4H), 2.99 (s, 3H); MS (APIMS) m/e 431 (M+H)$^+$, 448 (M+18)$^+$.

Example 23

((4-(6-((3,5-Difluorophenyl)methyl)(2H-benzo(3,4-d)1,3-dioxolan-5-yl))phenyl)methyl)nitrooxy 23a. (3,5-Difluorophenyl)(6-bromo(2H-benzo(d)1,3-dioxolan-5-yl))methan-1-ol The Grignard reagent was prepared by refluxing 1-bromo-3,5-difluorobenzene (1.93 g, 10 mmol), magnesium metal (267 mg, 11 mmol) and a few crystals of iodine in anhydrous THF (40 mL) under nitrogen atmosphere until most of the magnesium metal was consumed. The reaction mixture was cooled to room temperature and to this solution, bromopiperonal (1.36 g, 5 mmol) in anhydrous THF (10 mL) was added and the reaction mixture was stirred at room temperature for 1 hour. The reaction was then quenched with saturated aqueous ammonium chloride solution, acidified with 1 N HCl and the organic layer separated. The aqueous layer was extracted with ethyl acetate. The combined organic layers were dried over anhydrous sodium sulfate, filtered and the filtrate concentrated under reduced pressure to give the crude product. Purification by flash column chromatography using 10% ethyl acetate in hexanes as the eluant gave the title compound as a white solid (1.57 g, 92% yield), mp 74–77° C. $^1$H NMR (CDCl$_3$) δ6.98 (s, 1H), 6.92 (d, J=6.4 Hz, 2H), 6.86 (s, 1H), 6.70 (t, J=2.5 Hz, 1H), 6.1 (s, 1H), 5.98 (d, J=5.4 Hz, 2H), 2.69 (br s, 1H); $^{13}$C NMR (CDCl$_3$) δ164.6 (d, J=12.5 Hz), 161.3 (d, J=12.0 Hz), 148.2, 147.9, 146.3 (t, J=8 Hz), 135.0, 113.3, 112.5, 109.3 (d, J=28 Hz), 108.1, 102.9 (t, J=25 Hz), 102.0, 73.3.

23b. 5-((3,5-Difluorophenyl)methyl)-6-bromo-2H-benzo(d)1,3-dioxolane

The product of the Example 23a (400 mg, 1.66 mmol) was dissolved in anhydrous dichloromethane (5 mL) and under nitrogen atmosphere trifluoroacetic acid (5 mL) was added at 0° C. The reaction mixture was stirred at 0° C. for 15 minutes and to the resulting dark orange colored solution was added, in small portions, sodium borohydride (860 mg, 20 mmol). The reaction mixture was stirred at 0° C. for 15 minutes and then at room temperature for 30 minutes. The solvent and trifluoroacetic acid were evaporated under reduced pressure and the residue was extracted with dichloromethane. The combined organic extracts were washed with water, brine, dried over sodium sulfate, filtered and the filtrate was evaporated under reduced pressure to give the crude product that was recrystallized from hexane to give the title compound as a white solid (345 mg, 91% yield), mp 74° C. $^1$H NMR (CDCl$_3$) δ7.05 (s, 1H), 7.03 (s, 1H), 6.70–6.65 (m, 3H), 5.96 (s, 2H), 3.99 (s, 2H).

23c. (4-(6-((3,5-Difluorophenyl)methyl)-2H-benzo(3,4-d)1,3-dioxolan-5-yl)phenyl)methan-1-ol The product of Example 23b (327 mg, 1 mmol) and 4-(hydroxymethyl)benzeneboronic acid (195 mg, 1 mmol) were dissolved in toluene (25 mL) and sodium carbonate (2M, 1 mL, 2 mmol) was added. To this reaction mixture was added ethanol (3 mL) followed by tetrakis (triphenylphosphine)palladium (110 mg, 0.1 mmol) and the resulting reaction mixture was refluxed overnight under nitrogen atmosphere. The reaction mixture was cooled to room temperature and diluted with water (25 mL) stirred well, and the organic layer was separated. The aqueous layer was extracted with ethyl acetate. The combined organic layers were washed with water (4×25 mL), brine (1×25 mL), dried over sodium sulfate, filtered and the filtrate was evaporated under reduced pressure. Purification by silica gel flash column chromatography using 10% ethyl acetate in hexane as the eluant gave the title compound as a white solid (111 mg, 31% yield), mp 88–89° C. $^1$H NMR (CDCl$_3$) δ7.55 (m, 1H), 7.35 (d, J=8.0 Hz, 7.16 (d, J=8.0 Hz, 2H), 6.73 (s, 1H), 6.65 (s, 1H), 6.57 (tt, J=7.0 and 2.2 Hz, 1H), 6.45 (m, 2H), 5.98 (s, 2H), 4.72 (d, J=3.4 Hz, 1H), 3.80 (s, 2H), 1.67 (br s, 1H, OH).

23d. ((4-(6-((3,5-Difluorophenyl)methyl)(2H-benzo(3,4-d)1,3-dioxolan-5-yl))phenyl)methyl)nitrooxy To acetic anhydride (230 μL, 2.5 mmol) at 0° C. was added drop-wise, with stirring, fuming nitric acid (70 μL, 1.66 mmol). This mixture was immediately added drop-wise to a solution of the product of Example 23c (90 mg, 0.254 mmol) dissolved in ethyl acetate (0.5 mL), cooled to 0° C. The reaction mixture was stirred at 0° C. for 15 minutes, then at room temperature for 5 minutes and quenched with ice-cold water and extracted with ethyl acetate (2×50 mL). The combined organic extracts were washed with water (1×50 mL), brine (1×50 mL), dried over sodium sulfate, filtered and the filtrate was evaporated under reduced pressure to give the crude product. Purification by silica gel flash column chromatography using ethyl acetate:hexane (20:80) as an eluent gave the title compound as a thick colorless oil (65 mg, 64% yield). $^1$H NMR (CDCl$_3$) δ7.39 (d, J=8.0 Hz, 2H), 7.21 (d, J=8.0 Hz, 2H), 6.72 (s, 1H), 6.67 (s, 1H), 6.58 (tt, J=9.0 and 2.1 Hz, 1H), 6.47 (s, 1H), 6.45 (s, 1H), 5.98 (s, 2H), 5.45 (s, 2H), 3.80 (s, 2H); $^{13}$C NMR (CDCl$_3$) δ164.5 (d, J=13 Hz), 161.2 (d, J=13 Hz), 147.4, 146.4, 145.4 (t, J=9 Hz), 142.4, 134.9, 131.0, 130,0, 129.8 (2×C), 129.0 (2×C), 111.4 (d, J=24 Hz), 110.1, 101.4 (t, J=25 Hz), 101.3, 74.4, 38.5; LRMS (APIMS) m/z 417 (M+NH$_4$)$^+$.

Example 24

1-(2-(Cyclohexylidenemethyl)phenyl)-4-(methylsulfonyl)benzene 24a. 2-(4-Methylthiophenyl)benzaldehyde 2-Bromobenzaldehyde (3.7 g, 20 mmol) and 4-(methylthio) benzeneboronic acid (3.36 g, 20 mmol) were dissolved in toluene (80 mL) and sodium carbonate (2M, 10 mL, 20 mmol) was added. To this reaction mixture was added ethanol (5 mL) followed by tetrakis (triphenylphosphine)palladium (240 mg, 0.2 mmol) and the reaction mixture was refluxed overnight under nitrogen atmosphere. The reaction mixture was cooled to room temperature and diluted with water (50 mL), stirred well, and the organic layer was separated. The aqueous layer was extracted with ethyl acetate. The combined organic layers were washed with water (2×50 mL), brine (1×50 mL), dried over sodium sulfate, filtered and the filtrate concentrated under reduced pressure to give the crude product. Purification by flash column chromatography using 5% ethyl acetate in hexane gave the title compound as a colorless thick oil (4.4 g, 96% yield). $^1$H NMR (CDCl$_3$) δ9.98 (s, 1H), 8.01 (dd, J=7.8 Hz and 1.2 Hz, 1H), 7.6 (dt, J=7.5 and 1.4 Hz, 2H), 7.62–7.40 (m, 2H), 7.3–7.25 (m, 3H), 2.53 (s, 3H); LRMS (APIMS) m/z 329 (M+H)$^+$.

24b. (2-(4-Methylthiophenyl)phenyl)methan-1-ol

The product of Example 24a (912 mg, 4 mmol) was dissolved in ethanol (50 mL) and to this solution was added sodium borohydride (444 mg, 12 mmol). The reaction mixture was stirred at room temperature for 2 hours. The solvent was evaporated under reduced pressure and the residue treated with water (25 mL), neutralized with 1 N HCl, and extracted with ethyl acetate (2×50 mL). The combined organic extracts were washed with water, brine, dried over sodium sulfate, filtered and the filtrate was evaporated under reduced pressure to give the crude product (910 mg). Trituration with 10% ethyl acetate in hexane gave the title compound as a white solid (890 mg, 97% yield), mp 81–85° C. $^1$H NMR (CDCl$_3$) δ7.55 (m, 1H), 7.4–7.2 (m, 7H), 4.61 (s, 2H), 2.50 (s, 3H), 1.63 (br s, 1H, OH); LRMS (APIMS) m/z 248 (M+NH$_4$)$^+$.

24c. 1-(2-(Hydroxymethyl)phenyl)-4-(methylsulfonyl) benzene

The product of Example 24b (910 mg, 3.956 mmol) was dissolved in MeOH (160 mL). To this solution of OXONE® (5.1 g, 8.3 mmol) in water (20 mL) was added. The reaction mixture was stirred at room temperature for 2 hours diluted with water and ammonium hydroxide was added until the solution was basic. The solvent was evaporated under reduced pressure. The resulting product was extracted with ethyl acetate (2×125 mL), washed with water (2×50 mL), brine (1×50 mL), dried over sodium sulfate, filtered and the filtrate was evaporated under reduced pressure to give the crude product that was recrystallized from hexane to yield the title compound as white crystals, (1.036 g in 89% yield), mp 123–124° C. $^1$H NMR (CDCl$_3$) δ8.02 (d, J=8.2 Hz, 2H), 7.65 (d, J=8.2 Hz, 2H), 7.62 (s, 1H), 7.52–7.41 (m, 2H), 7.31 (d, J=8.2 Hz, 1H), 4.60 (s, 2H), 3.15 (s, 3H), 2.1 (br s, 1H, OH); $^{13}$C NMR (CDCl$_3$) δ146.5, 139.4, 139.2, 137.8, 130.2 (2×C), 129.8, 129.0, 128.7, 128.1, 127.9, 127.2 (2×C), 62.7, 44.5; LRMS (APIMS) m/z 280 (M+NH$_4$)$^+$.

24d. 2-(4-(Methylsulfonyl)phenyl)benzaldehyde

The product of Example 24c (910 mg, 3.47 mmol) and alumina (2 g) in anhydrous CH$_2$Cl$_2$ (20 mL) were stirred at room temperature. To this mixture, pyridinium chlorochromate (2.3 g, 11.4 mmol) was added and the mixture stirred at room temperature for 30 minutes. The reaction mixture was diluted with CH$_2$Cl$_2$ and the alumina was removed by filtration. The filtrate was washed with water (2×50 mL), saturated aqueous sodium bicarbonate (2×50 mL), brine (1×25 mL), then dried over anhydrous sodium sulfate, filtered and the filtrate was evaporated under reduced pressure. Purification by column chromatography using dichloromethane as the eluant gave the title compound as a white solid (580 mg, 64% yield), mp 115–116° C. $^1$H NMR (CDCl$_3$) δ9.99 (s, 1H), 8.09 (d, J=8.0 Hz, 2H), 7.73 (t, J=7.3 Hz, 1H), 7.63 (d, J=8.0 Hz, 3H), 7.46 (d, J=7.4 Hz, 1H), 3.17 (s, 3H); $^{13}$C NMR (CDCl$_3$) δ191.1, 143.7, 143.3, 140.2, 133.8, 133.6, 130.8 (2×C), 130,6, 129.8, 128.5, 127.4 (2×C) 44.5; LRMS (APIMS) m/z 278 (M+NH$_4$)$^+$.

24e. 1-(2-(Cyclohexylidenemethyl)phenyl)-4-(methylsulfonyl)benzene

A suspension of cyclohexyltriphenylphosphonium bromide (892 mg, 2.1 mmol) in anhydrous THF (10 mL) was stirred at 0° C. and t-BuOK (2 mL of 1 M, 2.0 mmol) was added drop-wise to the stirred suspension under nitrogen atmosphere. The reaction mixture was stirred at 0° C. for 15 minutes. To this suspension was added a solution of the product of Example 24d (182 mg, 0.7 mmol) in THF (5 mL). The reaction mixture was stirred for 15 minutes at 0° C., then slowly allowed to warm to room temperature and stirred at room temperature for 15 minutes. The reaction was then quenched with saturated aqueous ammonium chloride and the the aqueous layer was extracted with ethyl acetate (2×50 mL). The combined organic extracts were washed with water (1×50 mL), brine (1×50 mL) dried over sodium sulfate, filtered and the filtrate concentrated under reduced pressure. Purification by olumn chromatography using 20% ethyl acetate in hexane as the eluant gave the title compound as a white powder (80 mg, 35% yield), mp 83° C. $^1$H NMR (CDCl$_3$) δ 8.0 (d, J=7.9 Hz, 2H), 7.63 (d, J=7.9 Hz, 2H), 7.33 (m, 4H), 6.01 (s, 1H), 3.15 (s, 3H), 2.21 (m, 4H), 1.60–1.46 (m, 6H); LMRS (APIMS) m/z 344 (M+NH$_4$)$^+$.

Example 25

3-Fluorophenyl 2-(4-(methylsulfonyl)phenyl)phenyl ketone 25a. (3-Fluorophenyl)(2-(4-methylthiophenyl)phenyl) methan-1-ol The Grignard reagent was prepared by refluxing 1-bromo-3-fluorobenzene (1.75 g, 10 mmol), magnesium metal (267 mg, 11 mmol) and a few crystals of iodine in anhydrous THF (40 mL) under nitrogen atmosphere until most of the magnesium metal was consumed. The reaction mixture was cooled to room temperature and to this solution, a solution of the product of Example 24a (1.14 g, 5 mmol) in anhydrous THF (10 mL) was added and the reaction mixture was stirred at room temperature overnight. The reaction was quenched with saturated aqueous ammonium chloride, acidified with 1 N HCl and the organic layer was separated. The aqueous layer was extracted with ethyl acetate. The combined organic layers were dried over anhydrous sodium sulfate, filtered and the filtrate concentrated under reduced pressure to give the crude product. Purification by flash column chromatography using 10% ethyl acetate in hexane as the eluant gave the title compound as a colorless thick oil (1.58 g, 98% yield). $^1$H NMR (CDCl$_3$) δ7.47 (d, J=7.1 Hz, 1H), 7.40–7.18 (m, 8H), 6.90 (m, 3H), 5.91 (d, J=3.6 Hz, 1H), 2.52 (s, 3H), 2.25 (br s, 1H, OH); $^{13}$C NMR (CDCl$_3$) δ164.4, 161.1, 146.4, 140.7, 140.6, 137.7, 137.3, 130.1, 129.7 (2×C), 129.6, 128.0, 127.7, 127.3, 126.3 (2×C), 122.1, 114.0 (d, J=21 Hz), 113.5 (d, J=22 Hz), 71.8, 15.8; LRMS (APIMS) m/z 342 (M+NH$_4$)$^+$.

25b. 1-(2-((3-Fluorophenyl)hydroxymethyl)phenyl)-4-(methylsulfonyl)benzene

The product of Example 25a (220 mg, 0.679 mmol) was dissolved in dichloromethane (20 mL). Saturated aqueous sodium bicarbonate (5 mL) was added followed by recrystallized m-chlorobenzoic acid (302 mg, 1.69 mmol, 98% yield) and reaction mixture was stirred at room temperature for 2 hours. The organic layer was separated. The aqueous layer was extracted with dichloromethane and the combined organic layers were washed with 10% sodium bicarbonate (3×25 mL), water (1×25 mL), brine (1×25 mL), dried over sodium sulfate, filtered and the filtrate was evaporated under reduced pressure to give the crude product. Trituration with 10% ethyl acetate in hexane gave the title compound as a white solid that was recrystallized from hexane (190 mg, 79% yield), mp 117–119° C. $^1$H NMR (CDCl$_3$) δ7.99 (d, J=8.2 Hz, 2H), 7.62 (d, J=7.6 Hz, 1H), 7.51 (d, J=8.2 Hz, 2H), 7.44 (m, 2H), 7.31–7.20 (m, 2H), 7.0–6.7 (m, 3H), 5.86 (s, 2H), 3.15 (s, 3H), 2.35 (br s, 1H, OH); LRMS (APIMS) m/z 374 (M+NH$_4$)$^+$.

81

25c. 3-Fluorophenyl 2-(4-(methylsulfonyl)phenyl)phenyl ketone

The suspension of the product of Example 25b (230 mg, 0.647 mmol) and alumina (1 g) in anhydrous $CH_2Cl_2$ (20 mL) were stirred at room temperature. To this mixture, pyridinium chlorochromate (330 mg, 1.617 mmol) was added and the mixture stirred at room temperature for 1 hour. The reaction mixture was diluted with $CH_2Cl_2$ and the alumina was removed by filtration. The filtrate was washed with water (2×50 mL), saturated aqueous sodium bicarbonate (2×50 mL), brine (1×25 mL), dried over anhydrous sodium sulfate, filtered and the filtrate was evaporated under reduced pressure. Purification by column chromatography using dichloromethane as the eluant gave a product (220 mg) that was recrystallized from hexane to give the title compound as a white crystalline solid (180 mg, 79% yield), mp 105–106° C. $^1$H NMR ($CDCl_3$) δ7.79 (d, J=8.1 Hz, 2H), 7.35–7.15 (m, 10H), 2.83 (s, 3H); $^{13}$C NMR ($CDCl_3$) δ196.4, 164.0, 160.7, 145.7, 138.2, 131.0, 130.2, 130.1, 130.0, 129.8 (2×C), 129.1, 128.2, 127.7 (2×C), 125.7 (d, J=12 Hz), 120.1 (d, J=22 Hz), 116.3 (d, J=22 Hz), 44.4; LRMS (APIMS) m/z 372 $(M+NH_4)^+$.

Example 26

1-(2-((3-Fluorophenyl)methyl)phenyl)-4-(methylsulfonyl)benzene

The product of the Example 25b (140 mg, 0.393 mmol) was dissolved in anhydrous dichloromethane (10 mL) and under nitrogen atmosphere was added trifluoroacetic acid (5 mL) at 0° C. The reaction mixture was stirred at 0° C. for 10 minutes and to the resulting dark orange solution was then added, in small portions sodium borohydride (290 mg, 7.86 mmol). The reaction mixture was stirred at 0° C. for 15 minutes and then at room temperature for 5 minutes. The solvent and trifluoroacetic acid were evaporated under reduced pressure and the residue was extracted with dichloromethane. The combined organic extracts were washed with water, brine, dried over sodium sulfate and filtered. The filtrate was evaporated under reduced pressure to give the crude which upon trituration with hexane yielded the title compound as a white solid, (110 mg, 83%), mp 97–98° C. $^1$H NMR ($CDCl_3$) δ7.97 (d, J=8.3 Hz, 2H), 7.45 (d, J=8.3 Hz, 2H), 7.45–7.15 (m, 5H), 6.98 (dt, J=8.4 and 2.2 Hz, 1H), 6.75 (d, J=7.6 Hz, 1H), 6.63 (d, J=10 Hz, 1H); $^{13}$C NMR ($CDCl_3$) δ164.4, 161.2, 147.2, 143.3 (d, J=7 Hz), 140.3, 139.2, 137.2, 130.7, 130.1 (2×C), 129.9, 129.7 (d, J=2.5 Hz), 128.6, 127.1 (2×C), 126.9, 124.3 (d, J=2.5 Hz), 115.4 (d, J=21 Hz), 112.9 (d, J=21 Hz), 44.5, 38.9; LRMS (APIMS) m/z 358 $(M+NH_4)^+$.

Example 27

Assay for Human COX-1 and COX-2 Enzyme Activity

The human COX-1 and COX-2 enzyme activities and the measurement of the prostaglandin products synthesized were performed using the COX Inhibitor Screening Assay (Cayman Chemical, Ann Arbor, Mich.), which also contained the Prostaglandin Screening EIA Kit, used for prostaglandin quantification). The test compounds were dissolved at 50 times the highest final reaction concentration in DMSO or any other suitable solvent as stock solutions. These stock solutions were then diluted in the same solvent. Eight glass test tubes (13×100 mm) were placed in a 25° C. water bath. To each test tube was added 950 µL of reaction buffer (0.1 M Tris-HCl, pH 8.0, containing 5 mM EDTA,

82 and 2 mM phenol), 10 µL of 100 M heme solution, and 10 µL (5 units) of either human COX-1 or COX-2 enzyme and the resulting mixture was incubated for 2 minutes. Twenty µL of the solvent was added to one tube (100% initial activity or solvent control) and 20 µL of each dilution of the test compound was added to one tube each. Each tube was vortexed immediately after the addition. The enzyme was incubated with the inhibitor for 20 minutes at 25° C. The enzymatic reaction was then initiated by the addition of 10 µL of freshly prepared 10 mM arachidonic acid (neutralized with KOH), vortexed and then incubated for 2 minutes (or, in some cases as indicated, 30 seconds) at 37° C. The reaction was terminated by the addition of 50 µL of 1 M HCl, vortexed and placed at room temperature. One hundred µL of a saturated stannous chloride solution (50 mg/mL of 0.1 M HCl) was added and the reaction mixture was allowed to stand at room temperature for at least 5 minutes.

The prostaglandins (PG) produced in the reactions were assayed, after a 2,000-fold dilution, using the Prostaglandin Screening EIA Kit (Cayman Chemical, Ann Arbor, Mich.). The assay contains an antibody with broad specificity for all the prostaglandin families (PGF, PGE, PGD, and thromboxane B-type) synthesized in the COX-1/COX-2 reactions. The synthesized prostaglandin competes with a PG-tagged acetylcholine esterase tracer for binding to the PG antibody. Binding of synthesized PG lowers the colorimetric development of the Ellman's Reagent (computed as $\%B/B_0$). The actual amount of synthesized PG was interpolated from a standard curve using known amounts of supplied prostaglandin E2 ($PGE_2$) ($PGE_2$ concentration vs. $\%B/B_0$). The data generated were the mean±standard deviation of triplicate wells in the EIA for a single reaction at a given inhibitor concentration. A plot of % of control (i.e., the solvent control without inhibitor) vs. test compound inhibitor concentration for both isoenzymes was used to determine the $IC_{50}$'s for COX-1 and COX-2 for that test compound, when $IC_{50}$'s were calculated. The % inhibition for COX-1 and COX-2 enzyme activity by the test compounds at the indicated concentrations are given in Table 1.

TABLE 1

| | % INHIBITION OF HUMAN COX-1 AND COX-2 ENZYME ACTIVITY | |
|---|---|---|
| Test Compound | COX-1 Inhibition (% at 100 µM) | COX-2 Inhibition (% at 10 µM) |
| Example 1d | 5 | 90 |
| Example 1e | 0 | 100 |
| Example 3d | 0 | 90 |
| Example 6c | 30 | 65 |
| Example 6d | 20 | 20 |
| Example 8b | 0 | 30 |
| Example 8c | 25 | 80 |
| Example 9c | 70 | 90 |
| Example 10a | 30 | 100 |
| Example 10b | 20 | 70 |
| Example 11b | 10 | 100 |
| Example 15c | 15 | 90 |

The results show that the compounds listed in Table 1 are COX-2 selective inhibitors.

Example 28

Assay for Human COX-1 and COX-2 Enzyme Activity in Human Whole Blood

The assay for COX-1 and COX-2 enzyme activity, in the human whole blood was performed as described in Brideau et al., *Inflamm Res.*, 45: 68–74 (1996)). Human blood (≈50 mL) from male or female donors who had not received any aspirin or NSAIDs for 14 days was collected at two local area blood donor centers and placed in polypropylene syringes containing sodium heparin (20 units per mL blood, final concentration). The blood was transported to the laboratory on ice packs and used within 1.5 hours of collection. Upon receipt in the laboratory, the blood was allowed to come to room temperature for 15 minutes prior to distribution in 1 mL aliquots per well of 24 well tissue culture plates. The plates were then placed on a gently rotating platform shaker in a 5% $CO_2$ incubator at 37° C. for 15 minutes. Test compounds were dissolved in DMSO, at 1000 fold the final desired concentration, and further diluted, as indicated, in DMSO. One µL of each dilution of the test compound was added per well, in duplicate wells; wells not receiving test compound (e.g., basal, background or control wells) received 1 µL DMSO.

To induce COX-2, lipopolysaccharide (LPS) from *E. coli* (LPS, serotype 026:B6 or serotype 0127:B8, Sigma Chemical Co., St. Louis, Mo., Catalogue No. L3755 or L3129, respectively) was added at 10 µg/mL (2 µL of 5 mg/mL LPS in DMSO) to appropriate wells 15 minutes after the addition of the test compound. (Basal or background wells not incubated with LPS received 2 µL of DMSO.) For the stimulation of COX-1, the calcium ionophore, A23187 (free acid from Sigma Chemical Co., St. Louis, Mo., Catalogue No. C7522) was added at 25 µM (1 µL of 25 mM stock in DMSO) to separate wells 4.5 hours after the addition of the test compound. (Again, basal, background or control wells not stimulated with A23187 received 1 µL of DMSO.) At 5 hours after the addition of the test compound, all incubations were terminated by placement on ice and the addition of 2 mM EGTA (100 µL of 20 mM EGTA, tetrasodium, in PBS (phosphate buffered saline) without $Ca^{++}$ and $Mg^{++}$, pH 7.2)). The resulting solutions, were transferred by polyethylene transfer pipettes to 15 mL polypropylene centrifuge tubes and centrifuged at 1200 g for 10 minutes at 4° C. One hundred µL of plasma was removed from each blood sample and added to 1 mL of methanol in new 15 mL polypropylene centrifuge tubes, vortexed, and stored overnight at −20° C. The next day, the samples were centrifuged at 2000 g for 10 minutes at 4° C. and the supernatants transferred to glass tubes and evaporated to dryness. The samples were assayed for thromboxane $B_2$ using EIA kits supplied by Cayman Chemical Co. (Ann Arbor, Mich., Catalogue No. 519031) in duplicate wells after reconstitution with EIA Buffer and appropriate dilution (2000 fold for COX-1 and 500 fold for Cox-2 samples).

The % inhibition for COX-1 and COX-2 enzyme activity in human whole blood by the test compounds, at the indicated concentrations, are given in Table 2.

TABLE 2

% INHIBITION OF COX-1 AND COX-2 ENZYME ACTIVITY IN HUMAN WHOLE BLOOD

| Test Compound | COX-1 Inhibition (% at 100 µM) | COX-2 Inhibition (% at 10 µM) |
|---|---|---|
| Example 1d | 50 | 90 |
| Example 1e | 40 | 90 |
| Example 2c | 70 (at 30 µM) | 85 |
| Example 3c | 65 | 50 |
| Example 3d | 75 | 60 |
| Example 4c | 70 | 60 |
| Example 4d | 70 | 90 |
| Example 5c | 55 | 90 |
| Example 5d | 70 | 95 |
| Example 6c | 20 | 10 |
| Example 7d | 5 | 35 |
| Example 7e | 20 | 10 |
| Example 9c | 35 | 30 |
| Example 10a | 70 | 90 |
| Example 11b | 40 | 95 |
| Example 11c | 40 | 80 |
| Example 12c | 90 | 90 |
| Example 12d | 20 | 20 |
| Example 13c | 90 | 75 |
| Example 14c | 90 | 75 |
| Example 15c | 75 | 85 |
| Example 16 | 50 | 100 |
| Example 17d | 25 | 20 |
| Example 17e | 35 | 25 |
| Example 17f | 10 | 25 |
| Example 17h | 65 | 55 |
| Example 18a | 90 | 65 |
| Example 18b | 50 | 25 |
| Example 18c | 90 | 40 |
| Example 18d | 60 | 40 |
| Example 19a | 45 | 15 |
| Example 19b | 65 | 35 |
| Example 20 | 70 | 40 |
| Example 21 | 50 | 30 |
| Example 22 | 90 | 55 |
| Example 23d | 65 | 30 |
| Example 24e | 55 | 90 |
| Example 25c | 40 | 40 |
| Example 26 | 25 | 10 |

The results show that the compounds listed in Table 2 are COX-2 selective inhibitors.

The disclosure of each patent, patent application and publication cited or described in the present specification is hereby incorporated by reference herein in its entirety.

Although the invention has been set forth in detail, one skilled in the art will appreciate that numerous changes and modifications can be made to the invention, and that such changes and modifications can be made without departing from the spirit and scope of the invention.

What is claimed is:

1. A compound of Formula (I), or a pharmaceutically acceptable salt thereof:

wherein the compound of Formula (I) is:

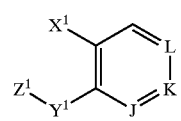

I wherein:

$X^1$ is:

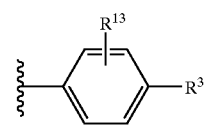

(a)

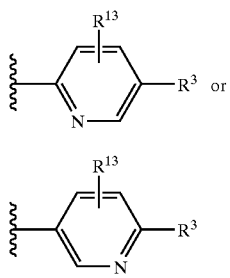

Y¹ is:
(a) —(CR¹R²)$_a$—;
(b) —(CR¹R²)$_b$—A¹—;
(c) —A¹—(CR¹R²)$_b$—;
(d) —CR¹R²—A¹—CR¹R²—; or
(e) —CR¹=;

Z¹ is:
(a) mono-, di- or tri-substituted phenyl or 2-naphthyl, wherein the substituents are each independently:
  (1) hydrogen;
  (2) halo;
  (3) lower alkyl;
  (4) haloalkyl;
  (5) alkylthio;
  (6) —NR⁴R⁵;
  (7) —C(O)-lower alkyl;
  (8) —(CH₂)$_a$—C(O)O—R⁶;
  (9) —OR¹¹; or
  (10) —(CR$_e$R$_f$)$_q$—U—V
(b) mono-, di- or tri-substituted cycloalkyl or heterocyclic ring, wherein the substituents are each independently:
  (1) hydrogen;
  (2) halo;
  (3) lower alkyl;
  (4) haloalkyl;
  (5) alkylthio;
  (6) —NR⁴R⁵;
  (7) —C(O)-lower alkyl;
  (8) —(CH₂)$_q$—C(O)O—R⁶;
  (9) —OR¹¹;
  (10) —(CR$_e$R$_f$)$_q$—U—V;
  (11) oxo; or
  (12) thial;
(c) alkyl;
and the bond between Y¹ and Z¹ may be a single bond or a double bond such that the valencies are satisfied;

A¹ is:
(a) oxygen;
(b) thio;
(c) sulfinyl;
(d) sulfonyl; or
(e) —N(R¹²)—;

—J=K—L= is:
(a) —CR⁷=N—CR⁸=;
(b) —CR⁸=N—CR⁷=;
(c) —N=N—CR⁷=;
(d) —N=N—CR⁸=;
(e) —CR⁷=N—N=;
(f) —CR⁸=N—N=;
(g) —N=CR⁷—N=; or
(h) —N=CR⁸—N=;

R¹ and R² are each independently:
(a) hydrogen;
(b) lower alkyl;
(c) substituted lower alkyl;
(d) lower alkoxy;
(e) lower haloalkyl; or
(f) halo; or R¹ and R² taken together are;
(a) oxo; or
(b) thial R³ is:
(a) —S(O)₂—CH₃;
(b) —S(O)₂—NH₂;
(c) —S(O)₂—N(H)—C(O)—CF₃;
(d) —S(O)(NH)—NH₂;
(e) —S(O)(NH)—CH₃;
(f) —S(O)(NH)—N(H)—C(O)—CF₃;
(g) —S(O)₂-haloalkyl; or
(h) —CH₂—U—V;

R⁴ is:
(a) hydrogen;
(b) substituted lower alkyl
(c) cycloalkyl
(d) cycloalkylalkyl;
(e) lower alkenyl;
(f) lower alkoxy;
(g) alkylcarbonyl;
(h) carboxylic ester;
(i) carboxamido;
(j) arylcarbonyl;
(k) alkylsulfonyl;
(l) arylsufonyl;
(m) alkylarylsulfonyl; or
(n) arylalkylsulfonyl;

R⁵ is:
(a) hydrogen; or
(b) lower alkyl; or

R⁴ and R⁵ taken together with the nitrogen to which they are attached form a heterocyclic ring;

R⁶ is:
(a) lower alkyl; or
(b) arylalkyl;

R⁷ is:
(a) hydrogen;
(b) halo;
(c) cyano;
(d) lower alkyl optionally substituted with:
  (1) halo;
  (2) alkoxy;
  (3) aryloxy;
  (4) cycloalkoxy;
  (5) ester;
  (6) carbamoyl;
  (7) —NR⁴R⁵;
  (8) phenyl optionally substituted with:
    (i) halo;
    (ii) hydroxy;
    (iii) lower alkyl; or
    (iv) alkoxy;
  (9) cyano;
  (10) —C(O)—H
  (11) alkylcarbonyl;
  (12) carboxylic ester;
  (13) carboxamido; or
  (14) heterocyclic ring;
(e) haloalkyl;
(f) lower alkenyl optionally substituted with:

(1) cyano;
(2) —C(O)—H
(3) alkycarbonyl;
(4) arylcarbonyl;
(5) —C(O)-cycloalkyl;
(6) —C(O)-heterocyclic ring;
(7) carboxylic ester;
(8) nitro; or
(9) —NR$^4$R$^5$;
(g) nitro;
(h) —NR$^4$R$^5$;
(i) —S(O)$_o$R$^9$;
(j) —S(O)$_o$NR$^5$R$^{10}$;
(k) —C(O)—H;
(l) alkylcarbonyl;
(m) arylcarbonyl;
(n) —C(O)-cycloalkyl;
(o) —C(O)-heterocyclic ring;
(p) carboxylic ester;
(q) carboxamido;
(r) alkoxy;
(s) aryloxy;
(t) cycloalkoxy;
(u) ester;
(v) carbamoyl; or
(w) —D R$^9$ is:
(a) lower alkyl;
(b) haloalkyl;
(c) phenyl; or
(d) benzyl;

R$^{10}$ is:
(a) hydrogen;
(b) lower alkyl;
(c) aryl;
(d) cycloalkyl;
(e) cycloalkylalkyl;
(f) lower alkenyl; or
(g) lower alkoxy;

R$^{11}$ is:
(a) lower alkyl;
(b) lower haloalkyl;
(c) alkoxyalkyl;
(d) alkylcarbonyl;
(e) arylalkylcarbonyl;
(f) carboxamido; or
(g) arylcarbonyl;

R$^{12}$ is:
(a) lower alkyl;
(b) hydrogen; or
(c) —C(O)H;

R$^{13}$ is:
(a) hydrogen;
(b) halogen;
(c) lower alkyl;
(d) lower alkoxy; or
(e) lower haloalkyl;

a is an integer equal to 1 or 3;
b is an integer equal to 2 or 3;
o is an integer from 0–2;
D is —W$_k$—E$_l$—(C(R$_e$)(R$_f$))$_p$—E$_c$—(C(R$_e$)(R$_f$))$_x$—W$_d$—(C(R$_e$)(R$_f$))$_y$—W$_i$—E$_j$—W$_g$—(C(R$_e$)(R$_f$))$_z$—U—V;
wherein c, d, g, i, j, k and l are each independently an integer from 0 to 3;
p, x, y and z are each independently an integer from 0 to 10;

W at each occurrence is independently:
(a) —C(O)—;
(b) —C(S)—;
(c) —T—;
(d) —(C(R$_e$)(R$_f$))$_h$—;
(e) alkyl;
(f) aryl;
(g) heterocyclic ring;
(h) arylheterocyclic ring, or
(i) —(CH$_2$CH$_2$O)$_q$—;

E at each occurrence is independently:
(a) —T—;
(b) alkyl;
(c) aryl;
(d) —(C(R$_e$)(R$_f$))$_h$—;
(e) heterocyclic ring;
(f) arylheterocyclic ring; or
(g) —(CH$_2$CH$_2$O)$_q$—;

h is an integer form 1 to 10;
q is an integer from 1 to 5;
R$_e$ and R$_f$ are each independently:
(a) hydrogen;
(b) alkyl;
(c) cycloalkoxy;
(d) halogen;
(e) hydroxy;
(f) hydroxyalkyl;
(g) alkoxyalkyl;
(h) arylheterocyclic ring;
(i) alkylaryl;
(j) cycloalkylalkyl;
(k) heterocyclicalkyl;
(l) alkoxy;
(m) haloalkoxy;
(n) amino;
(o) alkylamino;
(p) dialkylamino;
(q) arylamino;
(r) diarylamino;
(s) alkylarylamino;
(t) alkoxyhaloalkyl;
(u) sulfonic acid;
(v) alkylsulfonic acid;
(w) arylsulfonic acid;
(x) arylalkoxy;
(y) alkylthio;
(z) arylthio;
(aa) cyano;
(bb) aminoalkyl;
(cc) aminoaryl;
(dd) aryl;
(ee) arylalkyl;
(ff) alkylaryl;
(gg) carboxamido;
(hh) alkylcarboxamido;
(ii) arylcarboxarnido;
(jj) amidyl;
(kk) carboxyl;
(ll) carbamoyl;
(mm) alkylcarboxylic acid;
(nn) arylcarboxylic acid;
(oo) alkylcarbonyl;
(pp) arylcarbonyl;
(qq) ester;
(rr) carboxylic ester;
(ss) alkylcarboxylic ester;
(tt) arylcarboxylic ester;

(uu) sulfonamido;
(vv) alkylsulfonamido;
(ww) arylsulfonamido;
(xx) sulfonic ester;
(yy) urea;
(zz) nitro; or
(aaa) —(C($R_e$)($R_f$))$_k$—U—V; or $R_e$ and $R_f$ taken together with the carbon to which they are attached are:
(a) oxo;
(b) thial;
(c) aryl;
(d) heterocyclic ring;
(e) cycloalkyl group; or
(f) bridged cycloalkyl group;

U is:
(a) oxygen;
(b) sulfur; or
(c) —N($R_a$)$R_i$—;

V is:
(a) —NO; or
(b) —$NO_2$;

T at each occurrence is independently:
(a) a covalent bond,
(b) carbonyl,
(c) an oxygen,
(d) —S(O)$_o$—; or
(e) —N($R_a$)$R_i$—;

$R_a$ is:
(a) a lone pair of electron;
(b) hydrogen; or
(c) lower alkyl;

$R_i$ is:
(a) hydrogen;
(b) alkyl;
(c) aryl;
(d) alkylcarboxylic acid;
(e) aryl carboxylic acid;
(f) alkylcarboxylic ester;
(g) arylcarboxylic ester;
(h) alkylcarboxamido;
(i) arylcarboxamido;
(j) alkylaryl;
(k) alkylsulfinyl;
(l) alkylsulfonyl;
(m) arylsulfinyl;
(n) arylsulfonyl;
(o) sulfonamido;
(p) carboxamido;
(q) carboxylic ester;
(r) aminoalkyl;
(s) aminoaryl;
(t) —$CH_2$—C(U—V)($R_e$)($R_f$); or
(u) —($N_2O_2$—)$^-$·$M^+$, wherein $M^+$ is an organic or inorganic cation.

2. The compound of claim 1, wherein at least one substituent in the compound contains a "—U—V" moiety, wherein U and V are as defined herein.

3. A composition comprising the compound of claim 1 and a pharmaceutically acceptable carrier.

4. A composition comprising the compound of claim 2 and a pharmaceutically acceptable carrier.

5. A method for treating or reducing inflammation, pain or fever in a patient in need thereof comprising administering to the patient a therapeutically effective amount of the composition of claim 3.

6. A method for treating a disorder resulting from elevated levels of COX-2 in a patient in need thereof comprising administering to the patient a therapeutically effective amount of the composition of claim 3.

7. The method of claim 6, wherein the disorder resulting from elevated levels of COX-2 is angiogenesis, arthritis, asthma, bronchitis, menstrual cramps, premature labor, tendonitis, bursitis, a skin-related condition, neoplasia, inflammation in disease, ophthalmic disorder, pulmonary inflammation, central nervous system disorder, allergic rhinitis, respiratory distress syndrome, endotoxin shock syndrome, atherosclerosis, inflammation, microbial infection, cardiovascular disorder, urinary disorder, urological disorder, endothelial dysfunction, a disorder treated by the preservation of organs and tissues, a disorder treated by inhibition of activation, adhesion and infiltration of neutrophils at the site of inflammation, or a disorder treated by inhibition of platelet aggregation.

8. A method for treating a gastrointestinal disorder in a patient in need thereof comprising administering to the patient a therapeutically effective amount of the composition of claim 4.

9. The method of claim 8, wherein the gastrointestinal disorder is an inflammatory bowel disease, Crohn's disease, gastritis, irritable bowel syndrome, ulcerative colitis, a peptic ulcer, a stress ulcer, a bleeding ulcer, gastric hyperacidity, dyspepsia, gastroparesis, Zollinger-Ellison syndrome, gastroesophageal reflux disease, a bacterial infection, short-bowel (anastomosis) syndrome, a hypersecretory state associated with systemic mastocytosis or basophilic leukemia or hyperhistaminemia.

10. A method for facilitating wound healing in a patient in need thereof comprising administering to the patient a therapeutically effective amount of the composition of claim 4.

11. The method of claim 10, wherein the wound is an ulcer.

12. A method for treating or reversing renal toxicity in a patient in need thereof comprising administering to the patient a therapeutically effective amount of the composition of claim 4.

13. A method for improving the cardiovascular profile of a COX-2 selective inhibitor in a patient in need thereof comprising administering to the patient a therapeutically effective amount of the composition of claim 4.

14. The method of claim 13, further comprising administering to the patient a therapeutically effective amount of at least one of a 3-hydroxy-3-methylglutaryl coenzyme A, an antiplatelet agent, a thrombin inhibitor or a thromboxane inhibitor.

15. A method for improving the cardiovascular profile of a COX-2 selective inhibitor in a patient in need thereof comprising administering to the patient a therapeutically effective amount of at least one the compound of claim 2, or a pharmaceutically acceptable salt thereof, and at least one of a 3-hydroxy-3-methylglutaryl coenzyme A, an antiplatelet agent, a thrombin inhibitor or a thromboxane inhibitor.

16. The method for claim 15, wherein the compound of claim 2 or a pharmaceutically acceptable salt thereof, and the least one of a 3-hydroxy-3-methylglutaryl coenzyme A, an antiplatelet agent, a thrombin inhibitor or a thromboxane inhibitor are administered separately or are administered together in the form of a composition.

17. The method of claim 16, wherein the compound of claim 2 or a pharmaceutically acceptable salt thereof, and the least one of a 3-hydroxy-3-methylglutaryl coenzyme A, an antiplatelet agent, a thrombin inhibitor or a thromboxane inhibitor are administered orally, bucally, topically, by injection, by inhalation, or by transdermal application.

18. A composition comprising at least one compound of claim 1 or a pharmaceutically acceptable salt thereof, and at least one compound that donates, transfers or releases nitric oxide, or induces the production of endogenous nitric oxide or endothelium-derived relaxing factor, or is a substrate for nitric oxide synthase and, optionally, at least one therapeutic agent.

19. The composition of claim 18, further comprising a pharmaceutically acceptable carrier.

20. The composition of claim 18, wherein the compound that donates, transfers, or releases nitric oxide, or induces the production of endogenous nitric oxide or endothelium-derived relaxing factor or is a substrate for nitric oxide synthase is an S-nitrosothiol.

21. The composition of claim 20, wherein the S-nitrosothiol is S-nitroso-N-acetylcysteine, S-nitroso-captopril, S-nitroso-N-acetylpenicillamine, S-nitroso-homocysteine, S-nitroso-cysteine, S-nitroso-glutathione, or S-nitroso-cysteinyl-glycine.

22. The composition of claim 20, wherein the S-nitrosothiol is:

(i) $HS(C(R_e)(R_f))_m SNO$;
(ii) $ONS(C(R_e)(R_f))_m R_e$; or
(iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, a cycloalkylalkyl, a heterocyclicalkyl, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an alkoxy, an aryl, an arylalkyl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, an arylsulfonyloxy, a carbamoyl, a urea, a nitro, —T—Q—, or $(C(R_e)(R_f))_k$—T—Q, or $R_e$ and $R_f$ taken together are an oxo, a methanthial, a heterocyclic ring, a cycloalkyl group or a bridged cycloalkyl group; Q is —NO or —NO$_2$; and T is independently a covalent bond, a carbonyl, an oxygen, —S(O)$_o$— or —N(R$_a$)R$_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyloxy, an arylsulfinyl, an arylsulfonyloxy, an arylsulfonyl, a sulfonamido, a carboxamido, a carboxylic ester, an aminoalkyl, an aminoaryl, —CH$_2$—C(T—Q)(R$_e$)(R$_f$), or —(N$_2$O$_2$—)$^-$·M$^+$, wherein M$^+$ is an organic or inorganic cation; with the proviso that when $R_i$ is —CH$_2$—C(T—Q)(R$_e$)(R$_f$) or —(N$_2$O$_2$—)·M$^+$; then "—T—Q" can be a hydrogen, an alkyl group, an alkoxyalkyl group, an aminoalkyl group, a hydroxy group or an aryl group.

23. The composition of claim 18, wherein the compound that donates, transfers, or releases nitric oxide, or induces the production of endogenous nitric oxide or endothelium-derived relaxing factor, or is a substrate for nitric oxide synthase is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, citrulline, ornithine, glutamine, lysine, polypeptides comprising at least one of these amino acids or inhibitors of the enzyme arginase.

24. The composition of claim 18, wherein the compound that donates, transfers, or releases nitric oxide, or induces the production of endogenous nitric oxide or endothelium-derived relaxing factor, or is a NONOate.

25. The composition of claim 18, wherein the compound that donates, transfers, or releases nitric oxide, or induces the production of endogenous nitric oxide or endothelium-derived relaxing factor, or is a substrate for nitric oxide synthase is:

(i) a compound that comprises at least one ON—O—, ON—N—or ON—C—group;
(ii) a compound that comprises at least one O$_2$N—O—, O$_2$N—N—, O$_2$N—S—or —O$_2$N—C—group;
(iii) a N-oxo-N-nitrosoamine having the formula: R$^1$R$^2$N—N(O—M$^+$)—NO, wherein R$^1$ and R$^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and M$^+$ is an organic or inorganic cation.

26. The composition of claim 25, wherein the compound comprising at least one ON—O—, ON—N—or ON—C—group is an ON—O—polypeptide, an ON—N—polypeptide, an ON—C—polypeptide, an ON—O—amino acid, an ON—N—amino acid, an ON—C—amino acid, an ON—O—sugar, an ON—N—sugar, an ON—C—sugar, an ON—O—oligonucleotide, an ON—N—oligonucleotide, an ON—C—oligonucleotide, a straight or branched, saturated or unsaturated, substituted or unsubstituted, aliphatic or aromatic ON—O—hydrocarbon, a straight or branched, saturated or unsaturated, substituted or unsubstituted, aliphatic or aromatic ON—N—hydrocarbon, a straight or branched, saturated or unsaturated, substituted or unsubstituted, aliphatic or aromatic ON—C—hydrocarbon, an ON—O—heterocyclic compound, an ON—N—heterocyclic compound or a ON—C—heterocyclic compound.

27. The composition of claim 25, wherein compound comprising at least one O$_2$N—O—, O$_2$N—N—, O$_2$N—S—or O$_2$N—C—group is an O$_2$N—O—polypeptide, an O$_2$N—N—polypeptide, an O$_2$N—S—polypeptide, an O$_2$N—C—polypeptide, an O$_2$N—O—amino acid, O$_2$N—N—amino acid, O$_2$N—S—amino acid, an O$_2$N—C—amino acid, an O$_2$N—O—sugar, an O$_2$N—N—sugar, O$_2$N—S—sugar, an O$_2$N—C —sugar, an O$_2$N—O—oligonucleotide, an O$_2$N—N—oligonucleotide, an O$_2$N—S—oligonucleotide, an O$_2$N—C—oligonucleotide, a straight or branched, saturated or unsaturated, aliphatic or aromatic, substituted or unsubstituted O$_2$N—O—hydrocarbon, a straight or branched, saturated or unsaturated, aliphatic or aromatic, substituted or unsubstituted O$_2$N—N—hydrocarbon, a straight or branched, saturated or unsaturated, aliphatic or aromatic, substituted or unsubstituted O$_2$N—S—hydrocarbon, a straight or branched, saturated or unsaturated, aliphatic or aromatic, substituted or unsubstituted O$_2$N—C—hydrocarbon, an O$_2$N—O—heterocyclic compound, an O$_2$N—N—heterocyclic compound, an O$_2$N—S—heterocyclic compound or an O$_2$N—C—heterocyclic compound.

28. The composition of claim 18, wherein the therapeutic agent is a steroid, a nonsteroidal antiinflammatory compound, a 5-lipoxygenase inhibitor, a leukotriene $B_4$ receptor antagonist, a leukotriene $A_4$ hydrolase inhibitor, a 5-HT agonist, a 3-hydroxy-3-methylglutaryl coenzyme A inhibitor, a $H_2$ receptor antagonist, an antineoplastic agent, an antiplatelet agent, a thrombin inhibitor, a thromboxane inhibitor, a decongestant, a diuretic, a sedating or non-sedating anti-histamine, an inducible nitric oxide synthase inhibitor, an opioid, an analgesic, a *Helicobacter pylori* inhibitor, a proton pump inhibitor, an isoprostane inhibitor, or a mixture of two or more thereof.

29. The composition of claim 3, further comprising at least one therapeutic agent.

30. The composition of claim 29, wherein the therapeutic agent is a steroid, a nonsteroidal antiinflammatory compound, a 5-lipoxygenase inhibitor, a leukotriene $B_4$ receptor antagonist, a leukotriene $A_4$ hydrolase inhibitor, a 5-HT agonist, a 3-hydroxy-3-methylglutaryl coenzyme A inhibitor, a $H_2$ receptor antagonist, an antineoplastic agent, an antiplatelet agent, a thrombin inhibitor, a thromboxane inhibitor, a decongestant, a diuretic, a sedating or non-sedating anti-histamine, an inducible nitric oxide synthase inhibitor, an opioid, an analgesic, a *Helicobacter pylon* inhibitor, a proton pump inhibitor, an isoprostane inhibitor, or a mixture of two or more thereof.

31. A method for treating or reducing inflammation, pain or fever in a patient in need thereof comprising administering to the patient a therapeutically effective amount of the composition of claim 18 or 29.

32. A method for treating a disorder resulting from elevated levels of COX-2 in a patient in need thereof comprising administering to the patient a therapeutically effective amount of the composition of claim 18 or 29.

33. The method of claim 32, wherein the disorder resulting from elevated levels of COX-2 is angiogenesis, arthritis, asthma, bronchitis, menstrual cramps, premature labor, tendonitis, bursitis, a skin-related condition, neoplasia, inflammation in disease, ophthalmic disorder, pulmonary inflammation, central nervous system disorder, allergic rhinitis, respiratory distress syndrome, endotoxin shock syndrome, atherosclerosis, inflammation, microbial infection, cardiovascular disorder, urinary disorder, urological disorder, endothelial dysfunction, a disorder treated by the preservation of organs and tissues, a disorder treated by inhibition of activation, adhesion and infiltration of neutrophils at the site of inflammation, or a disorder treated by inhibition of platelet aggregation.

34. A method for treating a gastrointestinal disorder in a patient in need thereof comprising administering to the patient a therapeutically effective amount of the composition of claim 18 or 29.

35. The method of claim 34, wherein the gastrointestinal disorder is an inflammatory bowel disease, Crohn's disease, gastritis, irritable bowel syndrome, ulcerative colitis, a peptic ulcer, a stress ulcer, a bleeding ulcer, gastric hyperacidity, dyspepsia, gastroparesis, Zollinger-Ellison syndrome, gastroesophageal reflux disease, a bacterial infection, short-bowel (anastomosis) syndrome, a hypersecretory state associated with systemic mastocytosis or basophilic leukemia or hyperhistaminemia.

36. A method for facilitating wound healing in a patient in need thereof comprising administering to the patient a therapeutically effective amount of the composition of claim 18 or 29.

37. The method of claim 36, wherein the wound is an ulcer.

38. A method for treating or reversing renal toxicity in a patient in need thereof comprising administering to the patient a therapeutically effective amount of the composition of claim 18 or 29.

39. A method for improving the cardiovascular profile of a COX-2 selective inhibitor in a patient in need thereof comprising administering to the patient a therapeutically effective amount of the composition of claim 18.

40. The method of claim 39, further comprising administering to the patient a therapeutically effective amount of at least one of a 3-hydroxy-3-methylglutaryl coenzyme A, an antiplatelet agent, a thrombin inhibitor or a thromboxane inhibitor.

41. The composition of claim 18, wherein the least one compound of claim 1 or a pharmaceutically acceptable salt thereof and the least one compound that donates, transfers or releases nitric oxide, or induces the production of endogenous nitric oxide or endothelium-derived relaxing factor, or is a substrate for nitric oxide synthase are administered separately or are administered together in the form of a composition.

42. The composition of claim 18, wherein the least one compound of claim 1 or a pharmaceutically acceptable salt thereof, the least one compound that donates, transfers or releases nitric oxide, or induces the production of endogenous nitric oxide or endothelium-derived relaxing factor, or is a substrate for nitric oxide synthase and the at least one therapeutic agents are administered orally, bucally, topically, by injection, by inhalation, or by transdermal application.

43. A kit comprising at least one compound of claim 1 or a pharmaceutically acceptable salt thereof.

44. The kit of claim 43, further comprising at least one compound that donates, transfers or releases nitric oxide, or induces the production of endogenous nitric oxide or endothelium-derived relaxing factor, or is a substrate for nitric oxide synthase.

45. The kit of claim 43, further comprising at least one therapeutic agent.

46. A kit comprising at least one compound of claim 1 or a pharmaceutically acceptable salt thereof, and at least one compound that donates, transfers or releases nitric oxide, or induces the production of endogenous nitric oxide or endothelium-derived relaxing factor, or is a substrate for nitric oxide synthase.

47. The kit of claim 46, wherein the compound of claim 1 or a pharmaceutically acceptable salt thereof, and the at least one compound that donates, transfers or releases nitric oxide, induces the production of endogenous nitric oxide or endothelium-derived relaxing factor, or is a substrate for nitric oxide synthase are separate components in the kit or are in the form of a composition in the kit.

48. A kit comprising at least one compound of claim 1 or a pharmaceutically acceptable salt thereof, and at least one therapeutic agent.

49. The kit of claim 48, wherein the compound of claim 1 or a pharmaceutically acceptable salt thereof, and the at least one therapeutic agent are separate components in the kit or are in the form of a composition in the kit.

50. A compound selected from 4-(1-(3',5'-difluorophenyl)-1-hydroxymethyl)-1,2-dimethoxy-5-(methylsulfonylphenyl) benzene, 5-(1-(3',5'-difluorophenyl)methyl)-1,2-dimethoxy-4-(4-methylsulfonylphenyl) benzene, 5-(1-(3',5'-difluorophenyl)methyl)-1,2-dihydroxy-4-(4-methylsulfonylphenyl)benzene, 4-(1-(3',5'-difluorophenyl)-1-oxomethyl)-1,2-dimethoxy-5-(4-methylsulfonylphenyl)benzene, 4-(1-(3',5'-difluorophenyl)-1-oxomethyl)-1,2-hydroxy-5-(4-methylsulfonylphenyl)

benzene,1-(2-(cyclohexylidenemethyl)phenyl)-4-(methylsulfonyl)benzene, 1-(2-((3-fluorophenyl)hydroxymethyl)phenyl)-4-(methylsulfonyl) benzene,3-fluorophenyl 2-(4-(methylsulfonyl)phenyl)phenyl ketone, 1-(2-((3-fluorophenyl) methyl)phenyl)-4-(methylsulfonyl) benzene, or a pharmaceutically acceptable salt thereof.

51. A composition comprising at least one compound of claim 50 and a pharmaceutically acceptable carrier.

52. A kit comprising at least one compound of claim 50.

53. A composition comprising at least one compound of claim 50 and at least one compound that donates, transfers or releases nitric oxide, or induces the production of endogenous nitric oxide or endothelium-derived relaxing factor, or is a substrate for nitric oxide synthase, and, optionally, at least one therapeutic agent.

54. A composition comprising at least one compound of claim 50 and at least one therapeutic agent, and, optionally, at least one compound that donates, transfers or releases nitric oxide, or induces the production of endogenous nitric oxide or endothelium-derived relaxing factor, or is a substrate for nitric oxide synthase.

* * * * *